US007507756B2

(12) United States Patent
Jones et al.

(10) Patent No.: US 7,507,756 B2
(45) Date of Patent: *Mar. 24, 2009

(54) SCALABLE SYNTHESIS OF IMIDAZOLE DERIVATIVES

(75) Inventors: Todd K. Jones, Solana Beach, CA (US); Neelakandha Mani, San Diego, CA (US)

(73) Assignee: Janssen Pharmaceutica N.V., Beerse (BE)

( * ) Notice: Subject to any disclaimer, the term of this patent is extended or adjusted under 35 U.S.C. 154(b) by 471 days.

This patent is subject to a terminal disclaimer.

(21) Appl. No.: 11/123,631

(22) Filed: May 6, 2005

(65) Prior Publication Data

US 2005/0250948 A1 Nov. 10, 2005

Related U.S. Application Data

(60) Provisional application No. 60/569,405, filed on May 7, 2004.

(51) Int. Cl.
*A61K 31/415* (2006.01)
*C07D 233/00* (2006.01)
(52) U.S. Cl. .................................. 514/385; 548/300.1
(58) Field of Classification Search .............. 548/300.1; 514/385
See application file for complete search history.

(56) References Cited

U.S. PATENT DOCUMENTS

| 5,217,986 | A | 6/1993 | Pomponi et al. |
| 5,352,707 | A | 10/1994 | Pompni et al. |
| 5,869,479 | A | 2/1999 | Kreutner et al. |
| 6,207,678 | B1 | 3/2001 | Monaghan et al. |
| 6,380,396 | B1 | 4/2002 | Monaghan et al. |
| 7,265,135 | B2 * | 9/2007 | Bogenstaetter et al. ...... 514/326 |

FOREIGN PATENT DOCUMENTS

| EP | 0978512 A1 | 2/2000 |
| JP | 63-239273 | 10/1988 |
| WO | WO 99/42458 A1 | 8/1999 |
| WO | WO 02/076925 A2 | 10/2002 |
| WO | WO 02/079168 A1 | 10/2002 |

OTHER PUBLICATIONS

Arrang, J.-M. et al. Auto-inhibition of Brain Histamine Release Mediated by a Novel Class (H₃) of Histamine Receptor. *Nature* 1983, 302, 832-837.
Ash, A.S.F.; Schild, H.O. Receptors Mediating Some Actions of Histamine. *Br. J. Pharmac. Chemother.* 1966, 27, 427-439.
Barnes, J.C. et al. The Selective Histamine H3 Receptor Antagonist Thioperamide Improves Cognition and Enhances Hippocampal Acetylcholine Release In Vivo. *Soc. Neurosci. Abstr.* 1993, 19, 1813.
Black, J.W. et al. Definition and Antagonism of Histamine H₂-Receptors. *Nature* 1972, 236, 385-390.
Boga, C. et al. A New Synthesis of Chloroheterocycles via Metal-Halogen Exchange between Trichloroacetyl Derivatives and Heteroaromatic Lithium and Grignard Reagents. *J. Organomet. Chem.* 1999, 588, 155-159.
Boga, C. et al. Tetrahalogenomethanes: Simple Reagents for the Synthesis of Monohalogenated and Mixed Dihalogenated Aromatic Heterocycles via Metal-Halogen Exchange from Lithium Compounds. *J. Organomet. Chem.* 2000, 601, 233-236.
Ding, Y.-S. et al. Synthesis of High Specific Activity (+) and (−)-6-[$^{18}$F]-Fluoronorepinephrine via the Nucleophilic Aromatic Substitution Reaction. *J. Med. Chem.* 1991, 34, 767-771.
Eriksen, B.L. et al. Synthesis of 4- and 5-Substituted 1-Hydroxyimidazoles through Directed Lithiation and Metal-Halogen Exchange. *J. Org. Chem.* 2001, 66, 8344-8348.
Ganellin, C.R. et al. Synthesis of Potent Non-Imidazole Histamine $H_3$-Receptor Antagonists. *Arch. Pharm. Pharm. Med. Chem.* (Weinheim, Ger.) 1998, 331, 395-404.
Garbarg, M. et al. S-[2-(4-Imidazolyl)ethyl]isothiourea, a Highly Specific and Potent Histamine $H_3$ Receptor Agonist. *J. Pharmacol. Exp. Ther.* 1992, 263(1), 304-310.
Gewald, K. et al. 4-Amino-imidazole durch Thorpe-Cyclisierung. *Monatsh. Chem.* 1976, 107, 1413-1421.
Gilman, H. and F.W. Moore. Some Factors Affecting Halogen-Metal Interconversions. *J. Am. Chem. Soc.* 1940, 62, 1843-1846.
Gliatech, Inc. Press Release; Nov. 5, 1998.
Grimmett, M.R. Imidazoles. In *Comprehensive Heterocyclic Chemistry II, A Review of the Literature 1982-1995*; Katritzky, A.R. et al., Eds.; Elsevier: Tarrytown, NY, 1996; vol. 3, pp. 136-139.
Ichinose, M.; Barnes, P.J. Histamine $H_3$-Receptors Modulate Nonadrenergic Noncholinergic Neural Bronchoconstriction in Guinea-Pig In Vivo. *Eur. J. Pharmacol.* 1989, 174(1), 49-55.
Imamura, M. et al. Unmasking of Activated Histamine $H_3$-Receptors in Myocardial Ischemia: Their Role as Regulators of Exocytotic Norepinephrine Release. *J. Pharmacol. Exp. Ther.* 1994, 271(3), 1259-1266.
Imbach, J.L. et al. Recherches dans la Serie des Azoles. Synthese de Chloroimidazoles Non N-Substitutes. *J. Heterocycl. Chem.* 1967, 4, 451-452.
Jarosinski, M.A. et al. Preparation of Noncondensed 2-Substituted 1-Methyimidazoles via Ipso Substitution Reaction on 2-Sulfinyl or 2-Sulfonyl Derivatives of 4,5-Disubstituted 1-Methylimidazoles. *J. Org. Chem.* 1991, 56, 4058-4062.
Jones, R.G. Studies on Imidazoles. II. The Synthesis of 5-Imidazolecarboxylates from Glycine and Substituted Glycine Esters. *J. Am. Chem. Soc.* 1949, 71, 644-647.
Korte, A. et al. Characterization and Tissue Distribution of $H_3$ Histamine Receptors in Guinea Pigs by N alpha-Methylhistamine. *Biochem. Biophys. Res. Commun.* 1990, 168(3), 979-986.
Krause, M. et al. Medicinal Chemistry of Histamine $H_3$ Receptor Agonists. In *The Histamine $H_3$ Receptor—A Target for New Drugs*. Leurs, R.; Timmerman, H., Eds.; Elsevier: 1998; pp. 175-196.
Leurs, R. et al. The Medicinal Chemistry and Therapeutic Potentials of Ligands of the Histamine $H_3$ Receptor. *Prog. Drug Res.* 1995, 45, 107-165.

(Continued)

*Primary Examiner*—Rei-Tsang Shiao
*Assistant Examiner*—Susannah Chung

(57) ABSTRACT

Imidazole derivatives, compositions containing them, methods of preparing them, including regioselective scale-up synthetic methods, and methods of using them.

63 Claims, No Drawings

OTHER PUBLICATIONS

Lin, J.-S. et al. Involvement of Histaminergic Neurons in Arousal Mechanisms Demonstrated with $H_3$-Receptor Ligands in the Cat. *Brain Res.* 1990, 523, 325-330.

Linney, I.D. et al. Design, Synthesis, and Structure-Activity Relationships of Novel Non-Imidazole Histamine $H_3$ Receptor Antagonists. *J. Med. Chem.* 2000, 43(12), 2362-2370.

Lovenberg, T.W. et al. Cloning and Functional Expression of the Human Histamine $H_3$ Receptor. *Mol. Pharmacol.* 1999, 55(6), 1101-1107.

Lovenberg, T.W. et al. Cloning of Rat Histamine $H_3$ Receptor Reveals Distinct Species Pharmacological Profiles. *J. Pharmacol. Exp. Ther.* 2000, 293(3), 771-778.

Machidori, H. et al. Zucker Obese Rats: Defect in Brain Histamine Control of Feeding. *Brain Res.* 1992, 590, 180-186.

Mani, N.S. et al. A Scalable Synthesis of a Histamine $H_3$ Receptor Antagonist. *J. Org. Chem.* 2004, 69, 8115-8117.

McLeod, R.L. et al. Antimigraine and Sedative Activity of SCH 50971: A Novel Orally-Active Histamine $H_3$ Receptor Agonist. *Soc. Neurosci. Abstr.* 1996, 22, 2010.

Monti, J.M. et al. Effects of Selective Activation of Blockade of the Histamine $H_3$ Receptor on Sleep and Wakefulness. *Eur. J. Pharmacol.* 1991, 205(3), 283-287.

Morisset, S. et al. High Constitutive Activity of Native $H_3$ Receptors Regulates Histamine Neurons in Brain. *Nature* 2000, 408, 860-864.

Oda, T. et al. Molecular Cloning and Characterization of a Novel Type of Histamine Receptor Preferentially Expressed in Leukocytes. *J. Biol. Chem.* 2000, 275(47), 36781-36786.

Other News to Note. *Bioworld Today* 1999, 10(40), 3.

Panula, P. et al. Significant Changes in the Human Brain Histaminergic System in Alzheimer's Disease. *Soc. Neurosci. Abstr.* 1995, 21, 1977.

Phillips, J.G. and S.M. Ali. Medicinal Chemistry of Histamine $H_3$ Receptor Antagonists. In *The Histamine $H_3$ Receptor—A Target for New Drugs*. Leurs, R.; Timmerman, H., Eds.; Elsevier: 1998; pp. 197-222.

Piotrowski, D.W. A Concise Route to Novel 1-Aryl and 1-Pyridyl-2-Azabicyclo[2.1.1]hexanes. *Synlett* 1999, 7, 1091-1093.

Schlicker, E.; Marr, I. The Moderate Affinity of Clozapine at $H_3$ Receptors Is Not Shared by Its Two Major Metabolites and by Structurally Related and Unrelated Atypical Neuroleptics. *Naunyn-Schmiedeberg's Arch. Pharmacol.* 1996, 353, 290-294.

Shrivastava, S.K. et al. Dextrans—Potential Polymeric Drug Carriers for Flurbiprofen. *Pharmazie* 2003, 58(6), 389-391.

Stark, H. et al. Developments of Histamine $H_3$-Receptor Antagonists. *Drugs Future* 1996, 21(5), 507-520.

Suzuki, M. et al. Synthesis of 5-Carbon-Substituted 1-β-D-Ribofuranosylimidazole-4-carboxamides via Lithiation of a Primary Carboxamide. *Chem. Pharm. Bull.* 1987, 35(10), 4056-4063.

Tanaka, H. et al. A Lithiation Route to C-5 Substitution of an Imidazole Nucleoside. and its Application to the Synthesis of 3-Deazaguanosine. *Tetrahedron* 1986, 42, 1971-1980.

Taylor, S.D. et al. Recent Advances in Electrophilic Fluorination. *Tetrahedron* 1999, 55, 12431-12477.

Terasawa, K. et al. Cytoxic Activity of 5-Benzoylimidazole and Related Compounds against Human Oral Tumor Cell Lines. *Anticancer Res.* 2000, 21, 1081-1086.

Tozer, M.J.; Kalindjian, S.B. Histamine $H_3$ Receptor Antagonists. *Exp. Opin. Ther. Patents* 2000, 10(7), 1045-1055.

Walczynski, K. et al. Non-Imidazole Histamine $H_3$ Ligands. Part I. Synthesis of 2-(1-Piperazinyl)- and 2-(Hexahydro-1H-1,4-diazepin-1-yl)benzothiazole Derivatives as H3-Antagonists with H1 Blocking Activities. *Farmaco* 1999, 54, 684-694.

Walczynski, K. et al. Non-Imidazole Histamine $H_3$ Ligands, Part 2: New 2-Substituted Benzothiazoles as Histamine $H_3$ Antagonists. *Arch. Pharm. Pharm. Med. Chem.* (Weinheim, Ger.) 1999, 332, 389-398.

West, R.E. et al. Identification of Two $H_3$-Histamine Receptor Subtypes. *Mol. Pharmacol.* 1990, 38(5), 610-613.

West, R.E., Jr. et al. The Profiles of Human and Primate [$^3$H]N alpha-methylhistamine Binding Differ from That of Rodents. *Eur. J. Pharmacol.* 1999, 377, 233-239.

Yashioka, H. et al. New Synthetic Route to Imadazol[4,5-c]pyridines by the Thermal Electrocyclic Reaction of 1-Azahexatriene Systems. *Heterocycles* 1994, 41(1), 161-174.

Yokoyama, H. et al. Effect of Thioperamide, a Histamine $H_3$ Receptor Antagonist, on Electrically Induced Convulsions in Mice. *Eur. J. Pharmacol.* 1993, 234, 129-133.

\* cited by examiner

SCALABLE SYNTHESIS OF IMIDAZOLE DERIVATIVES

This application claims the benefit of U.S. provisional patent application Ser. No. 60/569,405, filed on May 7, 2004, which is incorporated herein by reference in its entirety.

FIELD OF THE INVENTION

The present invention relates to imidazole derivatives, their syntheses and their uses, and it also relates to regioselective scale-up synthetic methods for such derivatives.

BACKGROUND OF THE INVENTION

Histamine [2-(imidazol-4-yl)ethylamine] is a transmitter substance. Histamine exerts a physiological effect via multiple distinct G-protein coupled receptors. It plays a role in immediate hypersensitivity reactions and is released from mast cells following antigen IgE antibody interaction. The actions of released histamine on the vasculature and smooth muscle system account for the symptoms of the allergic response. These actions occur at the $H_1$ receptor (Ash, A. S. F., and Schild, H. O., Br. J. Pharmacol. 1966, 27, 427-439) and are blocked by the classical antihistamines (e.g., diphenhydramine). Histamine is also an important regulator of gastric acid secretion through its action on parietal cells. These effects of histamine are mediated via the $H_2$ receptor (Black, J. W., et al., Nature 1972, 236, 385-390) and are blocked by $H_2$ receptor antagonists (e.g., cimetidine). The third histamine receptor —$H_3$— was first described as a presynaptic autoreceptor in the central nervous system (CNS) (Arrang, J.-M., et al., Nature 1983, 302, 832-837) controlling the synthesis and release of histamine. Recent evidence has emerged showing that the $H_3$ receptors are also located presynaptically as heteroreceptors on serotonergic, noradrenergic, dopaminergic, cholinergic, and GABAergic (gamma-aminobutyric acid containing) neurons. These $H_3$ receptors have also recently been identified in peripheral tissues such as vascular smooth muscle. Consequently there are many potential therapeutic applications for histamine $H_3$ agonists, antagonists, and inverse agonists. (See: The Histamine $H_3$ Receptor-A Target for New Drugs; Leurs, R., Timmerman, H., Eds.; Elsevier, 1998; Morisset et al., Nature 2000, 408, 860-864.) A fourth histamine receptor —$H_4$— was recently described by Oda et al. (J. Biol. Chem. 2000, 275(47), 36781-36786).

The potential use of histamine $H_3$ agonists in sleep/wake and arousal/vigilance disorders is suggested based on animal studies (Lin, et al., Brain Res. 1990, 523, 325-330; Monti, et al., Eur. J. Pharmacol. 1991, 205(3), 283-287). Their use in the treatment of migraine has also been suggested (McLeod, et al., Soc. Neurosci. Abstr. 1996, 22, 2010) based on their ability to inhibit neurogenic inflammation. Other applications could be a protective role in myocardial ischemia and hypertension where blockade of norepinephrine release is beneficial (Imamura, et al., J. Pharmacol. Expt. Ther. 1994, 271(3), 1259-1266). It has been suggested that histamine $H_3$ agonists may be beneficial in asthma due to their ability to reduce non-adrenergic non-cholinergic (NANC) neurotransmission in airways and to reduce microvascular leakage (Ichinose, et al., Eur. J. Pharmacol. 1989, 174(1), 49-55).

Several indications for histamine $H_3$ antagonists and inverse agonists have similarly been proposed based on animal pharmacology experiments with known histamine $H_3$ antagonists (e.g. thioperamide). These include, dementia, Alzheimer's disease (Panula, et al., Soc. Neurosci. Abstr. 1995, 21,1977), epilepsy (Yokoyama, et al., Eur. J. Pharmacol. 1993, 234, 129-133) narcolepsy, eating disorders (Machidori, et al., Brain Res. 1992, 590,180), motion sickness, vertigo, attention deficit hyperactivity disorders (ADHD), learning and memory (Barnes, et al., Soc. Neurosci. Abstr. 1993, 19, 1813), schizophrenia (Schlicker, et al., Naunyn-Schmiedeberg's Arch. Pharmacol. 1996, 353, 290-294); (also see Stark, et al., Drugs Future 1996, 21(5), 507-520, and Leurs, et al., Prog. Drug Res. 1995, 45,107-165, and references cited therein). Histamine $H_3$ antagonists, alone or in combination with a histamine $H_1$ antagonist, are reported to be useful for the treatment of upper airway allergic response (U.S. Pat. Nos. 5,217,986, 5,352,707, and 5,869,479). Recently, a histamine $H_3$ antagonist (GT-2331) was identified and is being developed by Gliatech, Inc., (Gliatech, Inc., Press Release Nov. 5, 1998; Bioworld Today, Mar. 2, 1999) for the treatment of CNS disorders.

Background materials concerning histamine $H_3$ ligands have been reviewed (Leurs, R., Timmerman, H., 1998). Within this reference the medicinal chemistry of histamine $H_3$ agonists and antagonists is reviewed (see Krause, et al., and Phillips, et al., respectively). The importance of an imidazole moiety containing only a single substitution in the 4-position was noted together with the deleterious effects of additional substitution on activity. Particularly methylation of the imidazole ring at any of the remaining unsubstituted positions was reported to strongly decrease activity.

More recently several publications have described histamine $H_3$ ligands that do not contain an imidazole moiety. For example, Ganellin, et al., Arch. Pharm. (Weinheim, Ger.) 1998, 331, 395-404; Walczynski, et al., Arch. Pharm. (Weinheim, Ger.) 1999, 332, 389-398; Walczynski, et al., Farmaco 1999, 684-694; Linney, et al., J. Med. Chem. 2000, 43(12), 2362-2370; Tozer and Kalindjian, Exp. Opin. Ther. Patents 2000, 10(7), 1045-1055; U.S. Pat. No. 5,352,707; PCT Application WO99/42458, Aug. 26, 1999; and European Patent Application 0978512, Feb. 9, 2000.

Imidazole derivatives, such as acylimidazole derivatives, are reportedly useful in the preparation of drug carrier systems. For example, dextrans have been used as carriers for flurbiprofen (CAS Reg. 51543-38-5), a nonsteroidal anti-inflammatory prostaglandin synthesis inhibitor, more specifically, a non-selective inhibitor of the cyclooxygenase activity of prostaglandin H synthase (PGHS). To prepare a polymeric drug carrier for flurbiprofen, conjugates of this drug are reportedly synthesized by making their acylimidazole derivatives, which are condensed in situ with dextrans of a variety of molar masses. The conjugated entities reportedly show a remarkable reduction in ulcerogenicity with respect to the parent flurbiprofen. S. K. Shrivastava, et al., Pharmazie 2003, 58(6), 389-391. Embodiments of synthetic methods developed in the context of this invention are useful in the preparation of acylimidazole derivatives.

Other acylimidazole derivatives that comprise a quaternary ammonium moiety are reportedly antagonists of tachykinins, including NKA (neurokinin A), NKB (neurokinin B), and Substance P, acting at the human neurokinin-1 ($NK_1$), neurokinin-2 ($NK_2$), and neurokinin-3 ($NK_3$) receptors. Such compounds can reportedly be used for treating an inflammatory disease, a central nervous system (CNS) disorder, a gastrointestinal (GI) disorder, a urogenital tract disorder, a pulmonary disorder, an allergy, a hypersensitivity disorder, a proliferative disorder, a vasospastic disease, a fibrosing or collagen disease, reflux sympathetic dystrophy, an addiction disorder, a stress-related somatic disorder, a peripheral neuropathy, a neuropathological disorder, a disorder relaed to immune enhancement or suppression, a rheumatic disease, and an ophthalmic disease. See U.S. Pat. Nos. 6,207,678 B1 and 6,380,396 B1. Embodiments of synthetic methods developed in the context of this invention are useful in the preparation of acylimidazole derivatives that comprise a quaternary ammonium moiety.

Several publications have described the synthesis of functionalized imidazole compounds. Examples include U.S. Pat. No. 6,207,678 B1 (cols. 5-12, and preparations referred to in the Examples therein) and U.S. Pat. No. 6,380,396 B1 (cols. 5-12, and preparations referred to in the Examples therein) as well as a publication by Imbach, J. L., et al. (*J. Heterocycl. Chem.* 1967, 4, 451-454). 2-Chloroimidazoles can be useful intermediates in the preparation of functionalized imidazole derivatives and their preparation has been reported in the literature (Imbach, J. L., et al. 1967). Imidazole derivatives are important products because some of such products are pharmacologically active.

However, and as summarized below, conventional methodologies have synthetic disadvantages concerning one or more of these characteristics: Yield, scalability to multi-gram synthesis, regioselectivity, highly reactive by-product formation, impurity formation, number of synthetic steps, reaction conditions, and purifications. For example, some conventional methods rely on as many as eight synthetic steps, and/or are implemented under hazardous reaction conditions, and/or include reagents that are not desirable for large-scale work, and/or generate highly reactive by-products, and/or need chromatographic purifications.

For example, direct chlorination of N-alkylimidazole is not regioselective. Conventional methodologies to prepare the 2-chloro derivative rely on metal-halogen exchange between 2-imidazolyl lithium or a Grignard reagent, and a positive chlorine source. Two procedures that apply this strategy have been reported. In one of such procedures, (Boga, C., Del Vecchio, E., Forlani, L, Milanesi, L., and Todesco, P. E., *J. Organomet. Chem.* 1999, 588, 155-159), 1-methylimidazole is treated with n-BuLi to generate 2-imidazolyl lithium and then with trichloroacetyl chloride according to the following scheme:

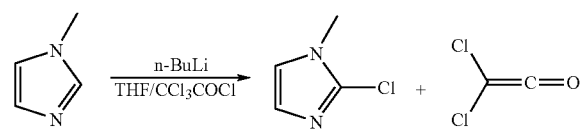

Reactions according to this methodology, however, produce a highly reactive dichloroketene as a by-product, which undergoes decomposition under the reaction conditions. This decomposition adversely affects product recovery, and the reaction is characterized by a yield that is too low to allow for its implementation in a scale-up process.

In another of such procedures (Boga, C., Del Vecchio, E., Forlani, L., and Todesco, P. E., *J. Organomet Chem.* 2000, 601, 233-236), carbon tetrachloride is used as the halogen source instead of trichloroacetyl chloride, according to the following scheme:

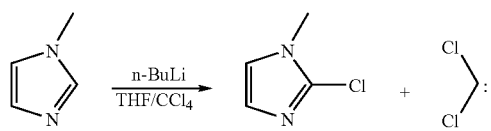

As evinced by the reaction scheme, this methodology also leads to the generation of highly reactive by-products during the reaction. The dichlorocarbene produced during the raction leads to the formation of polymeric impurities, which adversely affect the isolation of the product of interest in large-scale reactions, such as reactions for the production of more than, for example, 10 g of product.

Yields for the 2-chloro derivative of about 20%-40% have been reported for these conventional methodologies that employ reagents such as trichloroacetyl chloride or carbon tetrachloride. Yields of less than 10% for the same derivative are obtained when $Cl_2$ is used instead of trichloroacetyl chloride and carbon tetrachloride.

Highly reactive intermediates, such as dichloroketene and dichlorocarbene, are believed to participate in side reactions and undergo decomposition, making efficient conversion and product isolation unattainable in large-scale processes. Yet, large-scale processes are desirable for the synthesis of imidazole derivatives, including derivatives that are pharmacologically active, such as compounds that exhibit histamine $H_3$ receptor modulating effects, comprising histamine $H_3$ receptor antagonists.

In contrast with conventional methodologies, embodiments of the present invention provide synthetic methods that are characterized by at least one of the following features: High yields, with embodiments producing at least about 90% yield of the intermediate imidazole derivative of interest; regioselectivity; small number of synthetic steps, with embodiments having as few as two synthetic steps, such as regioselective substitution of the imidazole ring C-5 position with the use of a C-2 position blocking agent that is also a reactive leaving group in the subsequent substitution of such C-2 position; use of readily available and inexpensive reagents, such as perhaloalkanes and N—F electrophilic fluorinating agents as sources of halogen; stable by-product formation under synthetic reaction conditions; easy and reliable removal of by-products, such as removal of perhaloalkenes by distillation; purification by simple procedures, such as crystallization; and suitability for the production of multigram quantities of the products of interest.

A series of heterocyclic derivatives with the ability to modulate the activity of the histamine receptor, specifically the $H_3$ receptor, are described herein. Also described are methods for preparing these heterocyclic derivatives, and other imidazole derivatives, that are amenable to large-scale procedures. Synthetic methods described herein are useful in the preparation of such $H_3$ receptor modulators; embodiments of synthetic methods developed in the context of this invention are also useful, as indicated above, in the preparation of a variety of imidazole compounds in addition to such $H_3$ receptor modulators.

SUMMARY OF THE INVENTION

The present invention provides compounds of the formula (I), and methods of making the same:

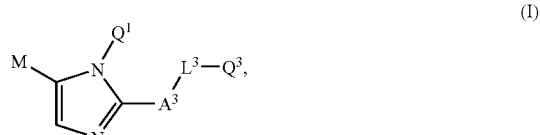

wherein:
Q$^1$ is selected from the group consisting of $C_{1-7}$alkyl and $C_{2-7}$alkenyl;

wherein $Q^1$ may be substituted with one or more substituents selected from the group consisting of halo, cyano, hydroxy, $OR^{11}$, $C_{1-5}$alkyl, $C_{1-5}$haloalkyl, $C_{2-5}$alkenyl, nitro, amino ($H_2N$—), $R^{11}HN$—, $R^{11}R^{12}N$—, amido ($H_2NC(O)$), $R^{11}HNC(O)$, $R^{11}R^{12}NC(O)$ and $R^{11}OC(O)$, and wherein $R^{11}$ and $R^{12}$ are independently $C_{1-6}$alkyl, $C_{1-6}$haloalkyl or $C_{2-6}$alkenyl;

M is a moiety of the formula —$CH_2R^M$, —$CHOHR^M$, —$C(=O)R^M$ or —$C(=N-OH)R^M$, wherein $R^M$ is selected from the group consisting of H, hydroxy, $C_{1-7}$alkyl, $R^{M1}HN$—, $R^{M1}R^{M2}N$—, cycloalkyl, aryl, biaryl and heterocyclyl, where when M is —$CHOHR^M$, then $R^M$ is not $R^{M1}HN$— or $R^{M1}R^{M2}N$—, wherein $R^M$ may be substituted with one or more substituents independently selected from the group consisting of halo, cyano, hydroxy, $OR^{M1}$, $C_{1-6}$alkyl, $C_{1-6}$haloalkyl, $C_{2-6}$alkenyl, nitro, amino ($H_2N$—), $R^{M1}HN$—, $R^{M1}R^{M2}N$—, amido ($H_2NC(O)$), $R^{M1}HNC(O)$ and $R^{M1}R^{M2}NC(O)$, and wherein $R^{M1}$ and $R^{M2}$ are either independently selected from H, $C_{1-6}$alkyl, $C_{1-6}$haloalkyl, and $C_{2-5}$alkenyl, or $R^{M1}$ and $R^{M2}$ are taken together to form $C_{4-7}$alkylene;

or M is hydrogen;

$A^3$ is NH, $NR^3$, sulfur, sulfoxide, sulfone or oxygen, wherein $R^3$ is $C_{1-6}$alkyl;

$L^3$ is $C_{1-7}$alkyl or $C_{2-7}$alkenyl;

wherein $L^3$ may be substituted with one or more substituents selected from the group consisting of halo, hydroxy, methoxy and amino ($H_2N$—);

or $L^3$ is absent; and $Q^3$ is selected from the group consisting of $C_{1-7}$alkyl, $C_{2-7}$alkenyl, $C_{3-7}$cycloalkyl, $C_{5-7}$cycloalkenyl, aryl, 4-7 membered heterocyclyl, ($C_{3-7}$cycloalkyl)-(4-7 membered heterocyclyl), (4-7 membered heterocyclyl)-($C_{3-7}$cycloalkyl), and bi-(4-7 membered heterocyclyl), and when $L^3$ is not absent, then $Q^3$ is additionally selected from the group consisting of $R^{31}HN$—, $R^{31}R^{32}N$—, azinoyl ($R^{31}HN^+(O^-)$ or $R^{31}R^{32}N^+(O^-)$), $C_{3-7}$cycloalkylamino, 4-7 membered heterocyclylamino, aryl $C_{1-6}$alkylamino, $C_{3-7}$ cycloalkylsulfanyl, 4-7 membered heterocyclylsulfanyl, and 4-7 membered heterocyclyloxy;

wherein $Q^3$ may be substituted with one or more substituents selected from the group consisting of halo, cyano, hydroxy, $OR^{31}$, $C_{1-5}$alkyl, $C_{1-5}$haloalkyl, $C_{2-5}$alkenyl, nitro, amino ($H_2N$—), $R^{31}HN$—, $R^{31}R^{32}N$—, amido ($H_2NC(O)$), $R^{31}HNC(O)$, $R^{31}R^{32}NC(O)$, $R^{31}OC(O)$, $C_{3-7}$cycloalkyl, monocyclic 4-7 membered heterocyclyl, and (monocyclic 4-7 membered heterocyclyl)-($C_{1-6}$alkyl), and wherein $R^{31}$ and $R^{32}$ are independently $C_{1-5}$alkyl, $C_{1-5}$haloalkyl or $C_{2-5}$alkenyl;

or a pharmaceutically acceptable ester, ether, N-oxide, amide, salt, hydrate, solvate or isotopically labeled form thereof.

In addition to the $Q^1$ assignments listed above and equivalents thereof, embodiments of the present invention also comprise assignments wherein $Q^1$ is -$Lnk_1$-$C(RR^1)(AR)$-$Lnk_2$-$N^+(QS^1)(QS^2)(QS^3)$, wherein $Lnk_1$ is a bond or $C_{2-4}$alkylene, optionally substituted with at least one of $C_{1-4}$alkyl, halo$C_{1-4}$alkyl, $C_{1-4}$alkoxy, halo$C_{1-4}$alkoxy, fluoro, chloro, bromo, iodo, and cyano;

$RR^1$ is H or $C_{1-6}$alkyl, optionally substituted with at least one of $C_{1-4}$alkyl, halo$C_{1-4}$alkyl, $C_{1-4}$alkoxy, halo$C_{1-4}$alkoxy, fluoro, chloro, bromo, iodo, and cyano;

AR is phenyl, naphthyl, benzyl, thienyl, benzo[b]thienyl, or indolyl, each of which is optionally substituted with 1 to 3 substituents, each of said substituents independently selected from $C_{1-4}$alkyl, halo$C_{1-4}$alkyl, $C_{1-4}$alkoxy, halo$C_{1-4}$alkoxy, fluoro, chloro, bromo, iodo, and cyano, or AR is 1,3-benzodioxolan-4 or 5-yl or 1,4-benzodioxan-5 or 6-yl;

$Lnk_2$ is a bond or $C_{2-4}$alkylene, optionally substituted with at least one of $C_{1-4}$alkyl, halo$C_{1-4}$alkyl, $C_{1-4}$alkoxy, halo$C_{1-4}$alkoxy, fluoro, chloro, bromo, iodo, and cyano; and each of $OS^1$, $QS^2$, and $QS^3$ is independently selected from H, $C_{1-6}$alkyl, optionally substituted with at least one of $C_{1-4}$alkyl, halo$C_{1-4}$alkyl, $C_{1-4}$alkoxy, halo$C_{1-4}$alkoxy, fluoro, chloro, bromo, iodo, and cyano, or any two of $QS^1$, $QS^2$, and $OS^3$ are taken together to form, together with the attachment quaternary nitrogen member, a heterocycle, while the third is selected from $C_{1-6}$alkyl, optionally substituted with at least one of $C_{1-4}$alkyl, $C_{1-4}$alkoxy, fluoro, chloro, bromo, iodo, and cyano, or the three $QS^1$, $QS^2$, and $QS^3$ are taken together to form, together with the attachment quaternary nitrogen member, optionally substituted quinuclidinium

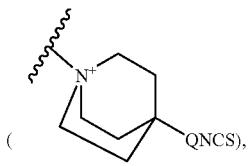

(QNCS), wherein QNCS is H or one of $C_{1-6}$alkyl, phenyl, naphthyl, benzyl, pyridyl, thienyl, $C_{3-7}$cycloalkyl, each of which being optionally substituted with at least one of $C_{1-4}$alkyl, halo $C_{1-4}$alkyl, $C_{1-4}$alkoxy, halo$C_{1-4}$alkoxy, fluoro, chloro, bromo, iodo, and cyano.

It is understood that whenever a substituent, such as $Q^1$, in any of the compounds given herein comprises a quaternary nitrogen moiety, the corresponding compound is given by a formula that comprises the positively charged moiety that is referred to explicitly and an acceptable anion, that is not necessarily referred to explicitly. This acceptable anion is preferably a pharmaceutically acceptable anion. Such pharmaceutically acceptable anion is chosen from the anionic forms provided herein in the context of describing pharmaceutically acceptable salts and equivalents thereof.

In addition to the assignments given above and equivalents thereof for the moiety -$A^3$-$L^3$-$Q^3$, embodiments of the present invention also comprise assignments where this moiety is —$C(O)$-$Lnk_3$-ACS, wherein $Lnk_3$ is a bond or $C_{2-4}$alkylene, optionally substituted with at least one of $C_{1-4}$alkyl, halo$C_{1-4}$alkyl, $C_{1-4}$alkoxy, halo$C_{1-4}$alkoxy, fluoro, chloro, bromo, iodo, and cyano; and ACS is one of H; $C_{1-6}$alkyl, optionally substituted with at least one of $C_{1-4}$alkyl, halo$C_{1-4}$alkyl, $C_{1-4}$alkoxy, halo$C_{1-4}$alkoxy, fluoro, chloro, bromo, iodo, and cyano; and ACS1, wherein ACS1 is selected from phenyl, $C_{3-7}$Cycloalkyl, and heteroaryl, each of said ACS1 being optionally benzo- or $C_{3-7}$cycloalkyl-fused, and optionally substituted, including any of the benzo- and $C_{3-7}$cycloalkyl-fused portions, by from 1 to 3 substituents, each independently selected from $C_{1-4}$alkyl, halo$C_{1-4}$alkyl, $C_{1-4}$alkoxy, halo$C_{1-4}$alkoxy, fluoro, chloro, bromo, iodo, cyano, phenoxy, $C_{2-4}$alkanoyl, $C_{1-4}$alkoxycarbonyl, $C_{3-7}$cycloalkyl, —S(O)$_m$(C$_{1-4}$alkyl), —NR$^{M1}$R$^{M2}$, —S(O)$_m$NR$^{M1}$R$^{M2}$, —N(R$^{M3}$)C$_{1-4}$alkanoyl, and —C(O)NR$^{M1}$R$^{M2}$, or ACS is 2,3-dihydrobenzo[b]furanyl or chromanyl, wherein R$^{M3}$ is one of H, and $C_{1-6}$alkyl, optionally substituted with at least one of $C_{1-4}$alkyl, halo$C_{1-4}$alkyl, $C_{1-4}$alkoxy, halo$C_{1-4}$alkoxy, fluoro, chloro, bromo, iodo, and cyano, where m=0, 1, or 2.

Similarly, isomeric forms of the compounds of formula (I), and of their pharmaceutically acceptable salts, esters, and amides, are encompassed within the present invention, and reference herein to one of such isomeric forms is meant to refer to at least one of such isomeric forms. One of ordinary skill in the art will recognize that compounds according to this invention may exist, for example in a single isomeric form whereas other compounds may exist in the form of a regioisomeric mixture.

The invention also features pharmaceutical compositions containing such compounds and methods of using such compositions in the treatment or prevention of disease states mediated by histamine $H_3$ receptor activity.

The invention also features a pharmaceutical composition comprising a compound of the invention and a pharmaceutically acceptable carrier; and methods of preparing or formulating such compositions. A composition of the invention may further include more than one compound of the invention, or a combination therapy (combination formulation or combination of differently formulated active agents).

Compounds according to this invention, alone or in combination with a histamine $H_1$ receptor antagonist or a histamine $H_2$ receptor antagonist, are useful for treating or preventing neurologic disorders including sleep/wake and arousal/vigilance disorders (e.g., insomnia and jet lag), attention deficit hyperactivity disorders (ADHD), learning and memory disorders, cognitive dysfunction, migraine, neurogenic inflammation, dementia, mild cognitive impairment (pre-dementia), Alzheimer's disease, epilepsy, narcolepsy with or without associated cataplexy, cataplexy, disorders of sleep/wake homeostasis, idiopathic somnolescense, excessive daytime sleepiness (EDS), circadian rhythm disorders, sleep/fatigue disorders, fatigue, drowsiness associated with sleep apnea, sleep impairment due to perimeopausal hormonal shifts, Parkinson's-related fatigue, multiple sclerosis (MS)-related fatigue, depression-related fatigue, chemotherapy-induced fatigue, eating disorders, obesity, motion sickness, vertigo, schizophrenia, substance abuse, bipolar disorders, manic disorders and depression, as well as other histamine $H_3$ receptor mediated disorders such as upper airway allergic response, asthma, itch, nasal congestion, and allergic rhinitis in a subject in need thereof. For example, the invention features methods for preventing, inhibiting the progression of, or treating upper airway allergic response, asthma, itch, nasal congestion and allergic rhinitis.

In yet another embodiment, compounds of this invention may be used in a combination therapy method including administering a jointly effective dose of an $H_3$ antagonist and administering a jointly effective dose of a histamine $H_1$ antagonist, such as loratidine (CLARITIN™), desloratidine (CLARINEX™), fexofenadine (ALLEGRA™) and cetirizine (ZYRTEC™), for the treatment of allergic rhinitis, nasal congestion, and allergic congestion.

In yet another embodiment, compounds of this invention may be used in a combination therapy method, including administering a jointly effective dose of an $H_3$ antagonist and administering a jointly effective dose of a neurotransmitter re-uptake blocker, such as a selective serotonin re-uptake inhibitor (SSRI), a serotonin-norepinephrine reuptake inhibitor, a noradrenergic reuptake inhibitor, or a non-selective serotonin, dopamine or norepinephrine re-uptake inhibitor, including fluoxetine (PROZAC™), sertraline (ZOLOFT™), paroxetine (PAXIL™) and amitryptyline, for the treatment of depression, mood disorders or schizophrenia. In an alternative embodiment, compounds of this invention may be used in a combination therapy method, including administering a jointly effective dose of an $H_3$ antagonist and administering a jointly effective dose of modafinil, for example, for the treatment of narcolepsy, excessive daytime sleepiness (EDS), Alzheimer's disease, depression, attention deficit disorders, MS-related fatigue, post-anesthesia grogginess, cognitive impairment, schizophrenia, spasticity associated with cerebral palsy, age-related memory decline, idiopathic somnolence, or jet-lag.

The present invention also provides process intermediates useful in preparing compounds of formula (I). A preferred embodiment of the present invention is an intermediate compound of the formula (II):

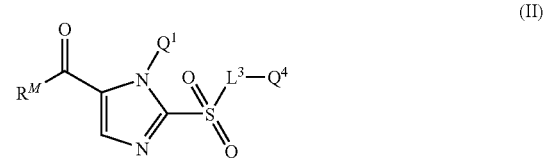

(II)

wherein:
Q$^1$ is selected from the group consisting of $C_{1-7}$alkyl and $C_{2-7}$alkenyl;
  wherein Q$^1$ may be substituted with one or more substituents selected from the group consisting of halo, cyano, hydroxy, OR$^{11}$, $C_{1-5}$alkyl, $C_{1-5}$haloalkyl, $C_{2-5}$alkenyl, nitro, amino (H$_2$N—), R$^{11}$HN—, R$^{11}$R$^{12}$N—, amido (H$_2$NC(O)), R$^{11}$HNC(O), R$^{11}$R$^{12}$NC(O) and R$^{11}$OC(O), and wherein R$^{11}$ and R$^{12}$ are independently $C_{1-6}$alkyl, $C_{1-6}$haloalkyl or $C_{2-6}$alkenyl;
R$^M$ is selected from the group consisting of H, hydroxy, methyl, R$^{M1}$HN—, R$^{M1}$R$^{M2}$N—, $C_{4-7}$cycloalkyl (e.g., cyclopentyl or cyclohexyl), aryl, biaryl (e.g., naphthyl or 4-biphenyl), and 4-7 membered heterocyclyl containing between 1 and 2 heteroatoms,
  wherein R$^M$ may be substituted with one or more substituents independently selected from the group consisting of halo, cyano, hydroxy, OR$^{M1}$, $C_{1-6}$alkyl, $C_{1-6}$haloalkyl, $C_{2-6}$alkenyl, nitro, amino (H$_2$N—), R$^{M1}$HN—, R$^{M1}$R$^{M2}$N—, amido (H$_2$NC(O)), R$^{M1}$HNC(O) and R$^{M1}$R$^{M2}$NC(O), and
  wherein R$^{M1}$ and R$^{M2}$ are independently $C_{1-6}$alkyl, $C_{1-6}$haloalkyl or $C_{2-5}$alkenyl;
L$^3$ is $C_{1-7}$alkyl, $C_{2-7}$alkenyl, or phenyl;
  wherein L$^3$ may be substituted with one or more substituents selected from the group consisting of halo, hydroxy, methoxy and amino (H$_2$N—); and
Q$^4$ is hydrogen;
or a derivative thereof that bears one or more protecting groups.

The present invention also features methods of making a compound of formula (I), a pharmaceutically acceptable salt, ester, ether, N-oxide, amide, hydrate, solvate or isotopically labeled form thereof, comprising: Reacting an imidazole compound of formula (A) with a base and at least one of a perhaloalkane (PHA) and an N—F electrophilic fluorinating agent (EFA), to form a 2-haloimidazole compound of formula (B), according to scheme 1.1:

Scheme I.1

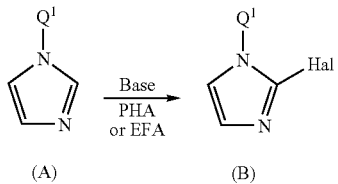

(A)                    (B)

wherein Hal is F or Cl, and $Q^1$ is defined as indicated herein.

The present invention also features methods of making a compound of formula (I), a pharmaceutically acceptable salt, ester, ether, N-oxide, amide, hydrate, solvate or isotopically labeled form thereof, by reacting an imidazole compound of formula (A) with a base and at least one of a perhaloalkane (PHA) and an N—F electrophilic fluorinating agent (EFA), to form a 2-haloimidazole compound of formula (B) according to Scheme 1.1, and further comprising: Reacting compound of formula (B) with a base and performing and addition with an electrophile (D) to form a C-5 position substituted imidazole compound of formula (C), according to Scheme 1.2:

Scheme I.2

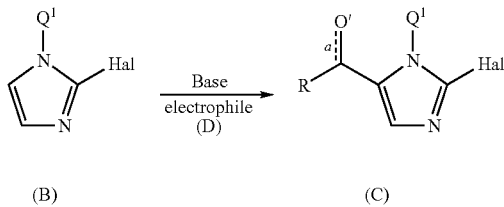

(B)                    (C)

wherein Hal is F or Cl, $Q^1$ and $R^M$ are defined as indicated herein, and wherein the set of (D), a, X, O' and R is one of the following assignment sets (i)-(iv):
  (i) electrophile (D) is O═C(X)R, a is a single bond, X is H, O' is OH, and R is $R^M$;
  (ii) electrophile (D) is O═C(X)R, a is a double bond, X is —N(OMe)Me or —N(Me)$_2$, O' is O, and R is $R^M$;
  (iii) electrophile (D) is CO$_2$, a is a double bond, and O' is O; R is hydroxy; and
  (iv) electrophile (D) is O═C(X)R, a is a double bond, O' is O, R is $R^M$, and X is fluoro, chloro, bromo or iodo.

The present invention also features methods of making a compound of formula (I), a pharmaceutically acceptable salt, ester, ether, N-oxide, amide, hydrate, solvate or isotopically labeled form thereof, comprising:
  Blocking the C-2 position by substituting said C-2 position with Hal to form a compound of formula (B), where Hal is fluoro or chloro;
  reacting said compound of formula (B) with a base and performing an addition with an electrophile (D) to form a C-5 position substituted imidazole compound of formula (C); and
  performing a nucleophilic substitution in said compound of formula (C) of said Hal in said C-2 position, wherein said Hal in said blocking the C-2 position is the same as said Hal that is displaced as a leaving group in said nucleophilic substitution, and said Hal is stable to metal exchange conditions.

The numbering of the imidazole positions as referenced to herein corresponds to the pattern given by the following conventional numbering:
Imidazole:

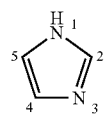

Terms such as "C-2 position", "C-4 position", and "C-5 position" concisely refer to the corresponding carbon members in an imidazole ring where the carbon and nitrogen ring members are numbered as in the conventional numbering given herein. These terms are used herein to describe not only the various positions in imidazole itself, but also when describing, in language other than systematic compound nomenclature, substitutions in the imidazole ring moiety that is part of imidazole derivatives. For example, "C-2 position" is the concise form used herein to refer to the carbon member at the C-2 position of the imidazole ring. Analogous considerations apply to the terms "C-4 position" and "C-5 position". As indicated above, substitutions in the imidazole ring are described by referring to the positions in the imidazole ring that are numbered as in the conventional numbering given herein. This is the case even when the standard name of the compound with the substituted ring would have a different number assigned to such position. For example, the imidazole derivative

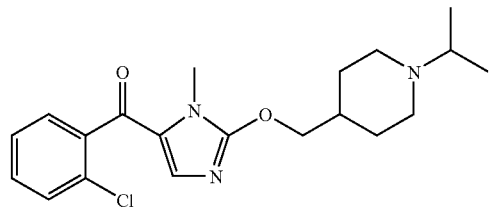

has the following standard name according to systematic nomenclature: (2-Chlorophenyl)-[2-(1-isopropyl-piperidin-4-ylmethoxy)-3-methyl-3H-imidazol-4-yl]-methanone. The substitutions in the imidazole ring moiety are referred to in this context as having, for example, a methyl in the N-1 position, even though the same position is referred to as position 3 in the standard name of the compound according to systematic nomenclature. Likewise, the halobenzoyl group is referred to as a substituent introduced in the C-5 position of the imidazole ring, even though such position is assigned the number 4 in the standard name of the same compound according to systematic nomenclature. This way of referring to the imidazole positions when describing substitutions in the context of reactivity is used herein because the numbering of the positions in imidazole itself is fixed as given above, whereas the numbering of the imidazole moiety positions when assigning standard names according to systematic nomenclature depends on the nature of the various groups attached to the imidazole moiety, as illustrated by the example given above.

Terms such as "imidazole compound" and "imidazole derivative" are used herein to refer to a compound whose structure comprises an imidazole ring, whether such ring is substituted or unsubstituted.

It is understood that the embodiments of the present invention include synthetic methods with imidazole and/or imidazole derivatives that have substituents in position 4 that are chemically compatible with the reactions described herein. No additional schemes are given explicitly herein because implementation of the methods of this invention with such compounds can be done in light of the disclosure provided herein and ordinary skill in the art. Furthermore, embodiments of the present invention include synthetic methods with imidazole and/or imidazole derivatives that have no substituents or that have substituents in the 1 and/or 5 positions that are different from those described herein and that are chemically compatible with the reactions described herein. No additional schemes are given explicitly herein because implementation of the methods of this invention with such compounds can be done in light of the disclosure provided herein and ordinary skill in the art. Analogously, no additional schemes are provided for steps that would lead to the additon or removal of substituents in any of positions 1, 4, and 5 that can be performed in light of the disclosure provided herein and the ordinary skill in the art.

The term perhaloalkane (PHA) refers to an alkane that has at least two carbon members and all such members are fully substituted with halogen members, such as fluoro and chloro. The limit to such alkane length and characteristics is determined by the suitability of the specific PHA as an effective electrophile for the synthesis of imidazole derivatives under the conditions as taught herein. The term perhalo$C_{2-6}$alkane refers to an alkane that has at least two carbon members, the total number of such carbon members ranges from two to six, and each carbon member is fully substituted with halogen members, such as fluoro and chloro. As long as PHA is an effective electrophile as indicated herein, the substituent halogen members are in some embodiments identical; in other embodiments, a plurality of different halogen members provides the substituents. When the substituents include at least one halogen member other than chloro, at least two substituents are chloro. PHA in some embodiments of this invention is a linear substituted alkane. In other embodiments, PHA is a branched substituted alkane. Examples of PHA include by way of illustration but not as limitation, the following: 1,2-Dichlorohexafluoropropane; perchloropropane; perchloropentane; 1,2-dichlorodecafluoropentane; perchloroethane (or hexachloroethane); and 1,1,1,2,4,4,4-heptachloro-3-fluoro-2-trichloromethyl-butane.

Whether stated explicitly or not in any part of the written description and claims, it is understood that each member and substituent assignment in the context of this invention is made independently of any other member and substituent assignment, unless stated otherwise. By way of a first example on substituent terminology, if substituent $S^1_{example}$ is one of $S_1$ and $S_2$, and substituent $S^2_{example}$ is one of $S_3$ and $S_4$, then these assignments refer to embodiments of this invention given according to the choices $S^1_{example}$ is $S_1$ and $S^2_{example}$ is $S_3$; $S^1_{example}$ is $S_1$ and $S^2_{example}$ is $S_4$; $S^1_{example}$ is $S_2$ and $S^2_{example}$ is $S_3$; $S^1_{example}$ is $S_2$ and $S^2_{example}$ is $S_4$; and equivalents of each one of such choices. The shorter terminology "$S^1_{example}$ is one of $S_1$ and $S_2$, and $S^2_{example}$ is one of $S_3$ and $S_4$," is accordingly used herein for the sake of brevity, but not by way of limitation. The foregoing first example on substituent terminology, which is stated in generic terms, is meant to illustrate the various substituent R assignments described herein. The foregoing convention given herein for substituents extends, when applicable, to other compound members, such as linking members, and indices.

Furthermore, when more than one assignment is given for any member or substituent, embodiments of this invention comprise the various groupings that can be made from the listed assignments, taken independently, and equivalents thereof. By way of a second example on substituent terminology, if it is herein described that substituent $S_{example}$ is one of $S_1$, $S_2$, and $S_3$, this listing refers to embodiments of this invention for which $S_{example}$ is $S_1$; $S_{example}$ is $S_2$; $S_{example}$ is $S_3$; $S_{example}$ is one of $S_1$ and $S_2$; $S_{example}$ is one of $S_1$ and $S_3$; $S_{example}$ is one of $S_2$ and $S_3$; $S_{example}$ is one of $S_1$, $S_2$ and $S_3$; and $S_{example}$ is any equivalent of each one of these choices. The shorter terminology "$S_{example}$ is one of $S_1$, $S_2$, and $S_3$," is accordingly used herein for the sake of brevity, but not by way of limitation. The foregoing second example on substituent terminology, which is stated in generic terms, is meant to illustrate the various substituent R assignments described herein. The foregoing convention given herein for substituents extends, when applicable, to linking membeother compound members, such as linking members, and indeces.

The nomenclature "$C_{i-j}$" with j>i, when applied herein to a class of substituents, is meant to refer to embodiments of this invention for which each and every one of the number of carbon members, from i to j and including i and j, is independently realized. By way of example, the term $C_{1-3}$ refers independently to embodiments that have one carbon member ($C_1$), embodiments that have two carbon members ($C_2$), and embodiments that have three carbon members ($C_3$).

When any variable referring to a substituent, compound member or index, occurs more than once, the full range of assignments is meant to apply to each occurrence, independently of the specific assignment(s) to any other occurrence of such variable.

According to the foregoing interpretive considerations on assignments and nomenclature, it is understood that explicit reference herein to a set implies, where chemically meaningful and unless indicated otherwise, independent reference to embodiments of such set, and reference to each and every one of the possible embodiments of subsets of the set referred to explicitly.

DETAILED DESCRIPTION OF THE INVENTION

The present invention is directed to compounds of formula (I) as herein defined, enantiomers, diastereomers, racemates, tautomers, hydrates, solvates thereof, pharmaceutically acceptable salts, amides and esters thereof, and methods of making such compounds.

The following terms are defined below, and by their usage throughout the disclosure.

As used herein, and unless specified otherwise, "halo" or "halogen" shall mean chloro, bromo, fluoro or iodo.

As used herein, and unless specified otherwise, the term "alkyl", whether used alone or as part of a substituent group, shall include unbranched and branched carbon chains, preferably of one to seven carbon atoms and more preferably of one to five carbon atoms, or one to three carbons, that are mono- or di-valent. For example, where an alkyl group has one carbon atom, the term "methyl" is used, which connotes the functional group (—$CH_3$), or (—$CH_2$—), as is chemically appropriate for a given substitution. Alkyl groups include but are not limited to methyl, ethyl, propyl, isopropyl, butyl, isobutyl, sec-butyl, tert-butyl, pentyl and the like.

As used herein, and unless specified otherwise, the term "haloalkyl" shall denote unbranched or branched, mono- or di-valent "alkyl" groups substituted with one or more "halo"

atoms, preferably one to five "halo" atoms, more preferably one to three "halo" atoms. "Haloalkyl" groups shall include partially and fully halogenated groups and groups with mixed halogens such as —CHCl—CH$_2$Cl, —CF$_3$, —CFCl$_2$, —CH(CH$_2$Br)—(CH$_2$)$_3$—CH$_2$I and —CCl$_2$—CH(CHCl$_2$)—CHCl—.

As used herein, and unless specified otherwise, the term "alkenyl", whether used alone or as part of a substituent group, shall include unbranched and branched carbon chains, preferably of two to seven carbon atoms and more preferably of two to five carbon atoms, that are mono- or di-valent. For example, alkenyl groups include vinyl, ethylidine (for example, ethan-1-ylidene and ethan-1-yl-2-ylidene), allyl, pent-3-enyl, pent[3]eno, 3-methylhex-4-enyl, and the like.

As used herein, and unless specified otherwise, unless otherwise noted, "alkoxy" shall denote the functional group (R—O—), where R is a mono-valent straight or branched chain "alkyl" group as described above. Examples include methoxy, ethoxy, n-propoxy, sec-butoxy, tert-butoxy, n-hexyloxy, and the like.

As used herein, and unless specified otherwise, unless otherwise noted, "cycloalkyl" shall denote a three- to eight-membered, saturated monocyclic carbocyclic ring structure. Suitable examples include cyclopropyl, cylcobutyl, cyclopentyl, cyclohexyl, cycloheptyl, cyclooctyl, and the like.

As used herein, unless otherwise noted, "cycloalkenyl" shall denote a three- to eight-membered, partially unsaturated, monocyclic, carbocyclic ring structure (preferably a five- to eight-membered, partially unsaturated, monocyclic, carbocyclic ring structure), wherein the ring structure contains at least one double bond. Suitable examples include cyclohexenyl, cyclopentenyl, cycloheptenyl, cyclooctenyl, cyclohexa-1,3-dienyl, and the like.

As used herein, unless otherwise noted, "aryl" shall refer to carbocyclic aromatic groups such as phenyl, naphthyl, (4-phenyl) phenyl and the like.

As used herein, unless otherwise noted, "arylalkyl" shall mean any "alkyl" group substituted with an aryl group such as phenyl, naphthyl, and the like, wherein the arylalkyl group is bound through the alkyl portion. Examples of an arylalkyl are benzyl, phenethyl, and napthylmethyl.

As used herein, unless otherwise noted, the terms "heterocycle", "heterocyclyl" and "heterocyclo" shall denote any three- to eight-membered (preferably four- to seven-membered, and more preferably four- to six-membered) monocyclic, seven- to eleven-membered (preferably eight- to ten-membered) bicyclic, or eleven- to fourteen-membered tricyclic ring structure containing at least one (e.g., between 1 and 2, or between 1 and 3) heteroatom selected from the group consisting of N, O and S, optionally containing one to four (e.g., between 1 and 2, or between 1 and 3) additional heteroatoms, wherein the ring structure is saturated, partially unsaturated, aromatic or partially aromatic. Attachment through any heteroatom or carbon atom of the heterocyclyl group that results in the creation of a stable structure is included within this term.

Exemplary monocyclic heterocyclyl groups can include azetidinyl, thietanyl, pyrrolidyl, pyrrolyl, imidazolinyl, imidazolyl, triazolyl (such as 1H-[1,2,4]triazolyl and 5-oxo-4,5-dihydro-1H-[1,2,4]triazol-3-yl), tetrazolyl, furyl, thienyl, oxazolyl, oxadiazolyl, thiazaolyl, thiadiazolyl, piperidyl, pyridyl, didehydropiperidyl, N-oxo-pyridyl, piperazyl, pyrimidyl, tetrahydropyranyl, morpholinyl, thiomorpholinyl, azepinyl, diazepanyl, and the like.

Exemplary bicyclic heterocyclyl groups can include thienofuryl, pyrrolopyridyl, furopyridyl, thienopyridyl, indolinyl, indolyl, indolizinyl, indazolyl, tetrahydroindazolyl, benzimidazolyl, purinyl, naphthyridinyl, quinolinyl, isoquinolinyl, quinuclidinyl, 3,4-dihydro-4-oxoquinazolinyl, and the like.

Exemplary tricyclic heterocylclyl groups can include carbozolyl, acridyl, phenazyl, phenoxazyl, phenothiazinyl, thianthrenyl, and the like.

As used herein, unless otherwise noted, "heterocyclylalkyl" shall mean any "alkyl" group substituted with a heterocyclyl group such as piperidyl or pyridyl, and the like, wherein the heterocylylalkyl group is bound to the rest of the molecule through the alkyl portion.

As used herein, unless otherwise noted, the terms "cycloalkyl-heterocyclyl", "heterocyclyl-cycloalkyl", "bi-heterocyclyl" and "biaryl" shall denote independently selected pairs of cyclic systems directly joined to each other by a single bond.

As used herein, unless otherwise noted, the terms "cycloalkylamino", "heterocyclylamino", and "arylalkylamino" shall denote a secondary amino group substituted with cycloalkyl, heterocyclyl, and arylalkyl groups, respectively, wherein the cycloalkylamino, heterocyclylamino, and arylalkylamino substituents are bound through the amino nitrogen. Suitable examples of such substituent groups include, but are not limited to, cyclohexylamino, piperidin-4-ylamino, benzylamino, and the like.

When a particular group is "substituted" (e.g., substituted alkyl, alkenyl, cycloalkyl, aryl, heterocyclyl, or heterocyclylalkyl), that group may have one or more valence allowed substituents, preferably from one to five substituents, more preferably from one to three substituents, most preferably from one to two substituents, independently selected from the list of substituents. Unless otherwise specified, the substituents are independently selected from halo, cyano, $C_{1-6}$alkyl, trifluoromethyl, hydroxy, hydroxyalkyl, alkoxy, amino, alkylamino, dialkylamino, nitro, aryl, arylalkyl, and the like.

It is intended that the definition of any substituent or variable at a particular location in a molecule be independent of its definitions elsewhere in that molecule. It is understood that substituents and substitution patterns on the compounds of this invention can be selected by one of ordinary skill in the art to provide compounds that are chemically stable and that can be readily synthesized by techniques known in the art as well as those methods set forth herein.

Under standard nomenclature used throughout this disclosure, the terminal portion of the designated side chain is described first, followed by the adjacent functionality toward the point of attachment. Thus, for example, a "phenyl(alkyl)amido(alkyl)" substituent refers to a group of the formula:

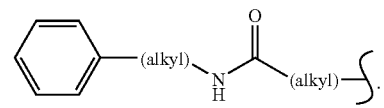

To provide a more concise description, some of the quantitative expressions given herein are not qualified with the term "about". It is understood that whether the term "about" is used explicitly or not, every quantity given herein is meant to refer to the actual given value, and it is also meant to refer to the approximation to such given value that would reasonably be inferred based on the ordinary skill in the art, including equivalents and approximations due to the experimental and/or measurement conditions for such given value. Whenever a yield is given as a percentage, such yield refers to a mass of the entity for which the yield is given with respect to the maximum mass of the same entity that could be obtained under the particular stoichiometric conditions. Concentrations that are given as percentages refer to mass ratios, unless indicated differently.

It is understood that substitutions and combinations of substitutions recited herein, whether stated explicitly or not, refer to substitutions that are consistent with the valency of the member being substituted. Terms such as "valence allowed site," "valence allowed member," and morphological variations thereof are used in this sense. For example, "valence allowed" when applied to a carbon member refers to the tetravalency of C; it refers to the trivalency of N when applied to a nitrogen member; and it refers to the bonding of a nitrogen member that is conventionally characterized with a positive electric charge or that is in a quaternary form. The present invention also encompasses compounds as described herein and equivalents thereof with at least one valence allowed nitrogen member, including but not limited to a quaternary nitrogen member and a nitrogen oxide, each of which may be prepared according to known methods (See, J. March, Advanced Organic Chemistry, 4th ed., 1991, pp. 411-412, 1200-1201; R. C. Larock, Comprehensive Organic Transformations, 1989, pp. 397-400, 421-425; and references cited therein).

The present invention provides compounds of the formula (I):

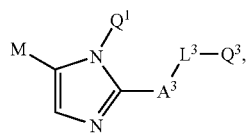

and the formula (II):

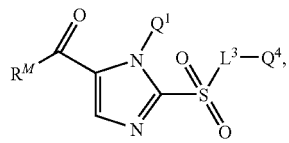

described in the Summary section above. The invention encompasses the described compounds or pharmaceutically acceptable esters, ethers, N-oxides, amides, salts, hydrates, solvates or isotopically labeled forms thereof.

A preferred embodiment of the present invention is a compound of formula (I) wherein $Q^1$ is unsubstituted or substituted $C_{1-7}$alkyl, more preferably unsubstituted or substituted $C_{1-5}$alkyl, and most preferably unsubstituted $C_{1-3}$alkyl. Preferred substituents are those having a basic amine.

A preferred embodiment of the present invention is a compound of formula (I) wherein $Q^1$ is methyl.

Another preferred embodiment of the present invention is a compound of formula (I) wherein M is a moiety of the formula $-CH_2R^M$, $-CHOHR^M$, $-C(=O)R^M$ or $-C(=N-OH)R^M$, and more preferably $-CHOHR^M$, $-C(=O)R^M$ or $-C(=N-OH)R^M$.

Another preferred embodiment of the present invention is a compound of formula (I) wherein $R^M$ is unsubstituted or substituted $C_{3-7}$cycloalkyl, aryl or 4-7 membered heterocyclyl.

Another preferred embodiment of the present invention is a compound of formula (I) wherein $R^M$ is aryl, and more preferably phenyl, unsubstituted or substituted with halo, cyano, hydroxy, methoxy, $C_{1-3}$alkyl, perhalomethyl, nitro or amino, and preferably substituted with F, Cl, Br, cyano, methoxy, $C_{1-3}$alkyl, hydroxy, $CF_3$ or nitro.

Another preferred embodiment of the present invention is a compound of formula (I) wherein $A^3$ is oxygen, sulfur or NH, and more preferably oxygen or sulfur, and most preferably oxygen.

Another preferred embodiment of the present invention is a compound of formula (I) wherein $L^3$ is unsubstituted or substituted $C_{1-5}$alkyl or $C_{2-5}$alkenyl.

Another preferred embodiment of the present invention is a compound of formula (I) wherein: $L^3$ is selected from (a) $C_{1-3}$alkyl, which may be unsubstituted or substituted, and independently may be unbranched or branched, and (b) $C_{4-5}$alkyl, which is branched or substituted, or both. Examples of preferred $L^3$ include methyl, ethyl, propyl, 1-methylethyl (isopropyl), 1-methylpropyl, 2-methylpropyl, 1-methylbutyl, 2-methylbutyl, 3-methylbutyl and 2-ethylpropyl.

Another preferred embodiment of the present invention is a compound of formula (I) wherein $L^3$ is absent.

Another preferred embodiment of the present invention is a compound of formula (I) wherein $Q^3$ is $R^{31}HN-$ or $R^{31}R^{32}N-$, or an unsubstituted or substituted nitrogen-containing 5-6 membered heterocyclyl, ($C_{3-6}$cycloalkyl)-(5-6 membered heterocyclyl), (5-6 membered heterocyclyl)-($C_{3-6}$ cycloalkyl) or bi-heterocyclyl, and more preferably $R^{31}R^{32}N-$ or an unsubstituted or substituted nitrogen-containing 5-6 membered heterocyclyl.

Another preferred embodiment of the present invention is a compound of formula (I) wherein: $Q^1$ is methyl; M is a moiety of the formula $-CH_2R^M$, $-CHOHR^M$, $-C(=O)R^M$ or $-C(=N-OH)R^M$; $R^M$ is phenyl or pyridyl, where $R^M$ is unsubstituted or substituted with F, Cl, Br, cyano, methoxy, $C_{1-3}$alkyl, $CF_3$ or nitro; $A^3$ is oxygen or sulfur; $L^3$ is selected from (a) $C_{1-3}$alkyl, which may be unsubstituted or substituted, and independently may be unbranched or branched, and (b) $C_{4-5}$alkyl, which is branched or substituted, or both; and $Q^3$ is $R^{31}R^{32}N-$.

Another preferred embodiment of the present invention is a compound of formula (I) wherein: $Q^1$ is methyl; M is a moiety of the formula $-CH_2R^M$, $-CHOHR^M$ or $-C(=O)R^M$; $R^M$ is phenyl unsubstituted or substituted with F, Cl, Br, cyano, methoxy, $C_{1-3}$alkyl, $CF_3$ or nitro; $A^3$ is oxygen or sulfur; $L^3$ is unsubstituted or substituted $C_{1-5}$alkyl or $C_{2-5}$alkenyl, or $L^3$ is absent; and $Q^3$ is an unsubstituted or substituted nitrogen-containing 5-6 membered heterocyclyl (e.g., piperidino, piperazino, or N-substituted 4-piperidinyl).

Another preferred embodiment of the present invention is a compound of formula (I) wherein:

Q is $C_{1-3}$alkyl;
wherein $Q^1$ may be substituted with one substituent selected from the group consisting of amino, $R^{11}HN-$, $R^{11}R^{12}N-$, amido, $R^{11}HNC(O)$, $R^{11}R^{12}NC(O)$ and $R^{11}OC(O)$, and
wherein $R^{11}$ and $R^{12}$ are independently $C_{1-5}$alkyl, $C_{1-5}$haloalkyl or $C_{2-5}$alkenyl;

M is a moiety of the formula $-CH_2R^M$, $-CHOHR^M$, or $-C(=O)R^M$,
wherein $R^M$ is selected from the group consisting of $C_{1-3}$alkyl, $R^{M1}HN-$, $R^{M1}R^{M2}N-$, $C_{5-7}$cycloalkyl, aryl, biaryl and 4-7 membered heterocyclyl containing between 1 and 2 heteroatoms, where when M is —CHOHR$^M$, then R$^M$ is not R$^{M1}$HN— or R$^{M1}$R$^{M2}$N—, wherein R$^M$ may be substituted with one or more substituents independently selected from the group consisting of halo, cyano, hydroxy, OR$^{M1}$, C$_{1-5}$alkyl, nitro, and amino; and A$^3$ is sulfur or oxygen;

L$^3$ is C$_{1-7}$alkyl or C$_{2-7}$alkenyl;

wherein L$^3$ may be substituted with one or more substituents selected from the group consisting of halo, hydroxy, methoxy and amino (H$_2$N—);

or L$^3$ is absent; and

Q$^3$ is selected from the group consisting of C$_{1-7}$alkyl, C$_{2-7}$alkenyl, C$_{3-7}$cycloalkyl, C$_{5-7}$cycloalkenyl, aryl, 4-7 membered heterocyclyl, (C$_{3-7}$cycloalkyl)-(4-7 membered heterocyclyl), (4-7 membered heterocyclyl)-(C$_{3-7}$cycloalkyl), bi-(4-7 membered heterocyclyl), and when L$^3$ is not absent, then Q$^3$ is additionally selected from the group consisting of R$^{31}$HN—, R$^{31}$R$^{32}$N—, azinoyl, C$_{3-7}$cycloalkylamino, 4-7 membered heterocyclylamino, aryl C$_{1-6}$alkylamino, C$_{3-7}$cycloalkylsulfanyl, 4-7 membered heterocyclylsulfanyl, and 4-7 membered heterocyclyloxy;

wherein Q$^3$ may be substituted with one or more substituents selected from the group consisting of halo, cyano, hydroxy, OR$^{31}$, C$_{1-5}$alkyl, C$_{1-5}$haloalkyl, C$_{2-5}$alkenyl, nitro, amino, R$^{31}$HN—, R$^{31}$R$^{32}$N—, amido, R$^{31}$HNC(O), R$^{31}$R$^{32}$NC(O), R$^{31}$OC(O), C$_{3-7}$cycloalkyl, monocyclic 4-7 membered heterocyclyl, and (monocyclic 4-7 membered heterocyclyl)-alkyl, and wherein R$^{31}$ and R$^{32}$ are independently C$_{1-5}$alkyl, C$_{1-5}$haloalkyl or C$_{2-5}$alkenyl;

or a pharmaceutically acceptable ester, ether, N-oxide, amide, salt, hydrate, solvate or isotopically labeled form thereof.

Preferred compounds of the present invention are as described in Examples I through V and XI through XXIV.

More preferred compounds of the present invention are:

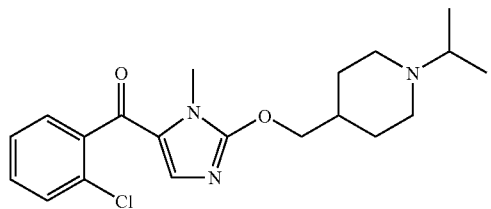

(2-Chlorophenyl)-[2-(1-isopropyl-piperidin-4-yl-methoxy)-3-methyl-3H-imidazol-4-yl]-methanone;

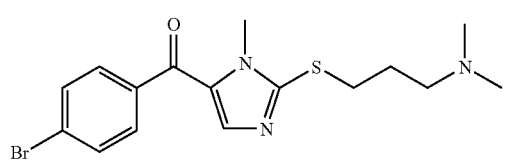

(4-Bromophenyl)-[2-(3-dimethylamino-propylsulfanyl)-3-methyl-3H-imidazol-4-yl]-methanone;

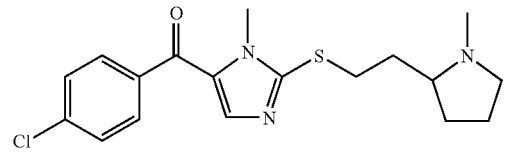

(4-Chlorophenyl)-{3-methyl-2-[2-(1-methylpyrrolidin-2-yl)-ethylsulfanyl]-3H-imidazol-4-yl}-methanone;

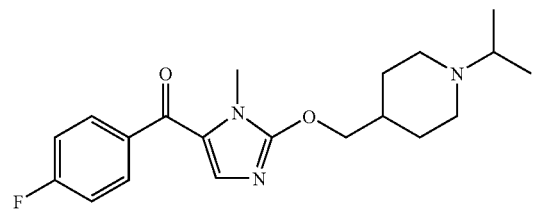

(4-Fluorophenyl)-[2-(1-isopropyl-piperidin-4-yl-methoxy)-3-methyl-3H-imidazol-4-yl]-methanone;

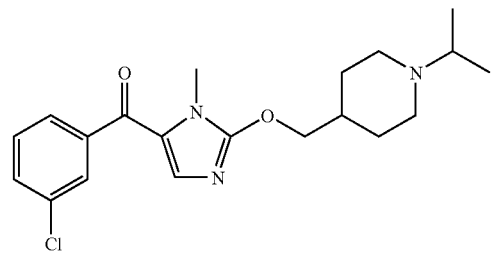

(3-Chlorophenyl)-[2-(1-isopropyl-piperidin-4-yl-methoxy)-3-methyl-3H-imidazol-4-yl]-methanone;

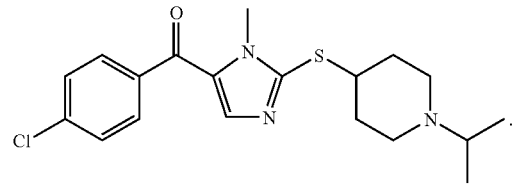

(4-Chlorophenyl)-[2-(1-isopropyl-piperidin-4-ylsulfanyl)-3-methyl-3H-imidazol-4-yl]-methanone;

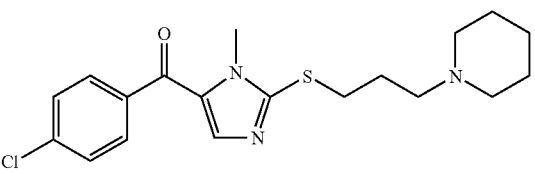

(4-Chlorophenyl)-[3-methyl-2-(3-piperidin-1-yl-propyl-sulfanyl)-3H-imidazol-4-yl]-methanone;

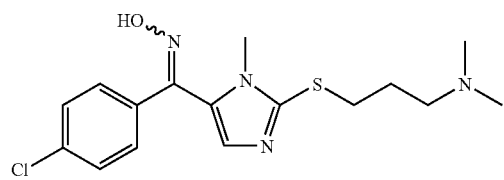

(4-Chlorophenyl)-[2-(3-dimethylamino-propylsulfanyl)-3-methyl-3H-imidazol-4-yl]-methanone oxime;

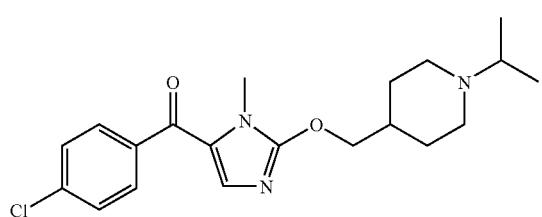

(4-Chlorophenyl)-[2-(1-isopropyl-piperidin-4-yl-methoxy)-3-methyl-3H-imidazol-4-yl]-methanone;

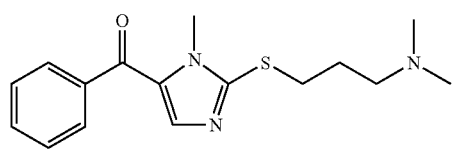

[2-(3-Dimethylamino-propylsulfanyl)-3-methyl-3H-imidazol-4-yl]-phenyl-methanone;

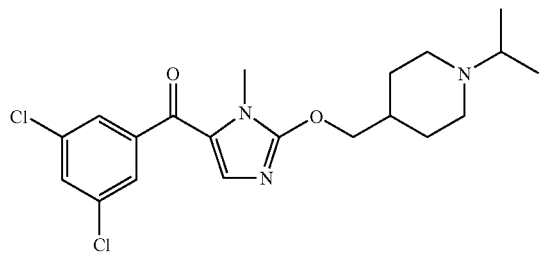

(3,5-Dichlorophenyl)-[2-(1-isopropyl-piperidin-4-yl-methoxy)-3-methyl-3H-imidazol-4-yl]-methanone;

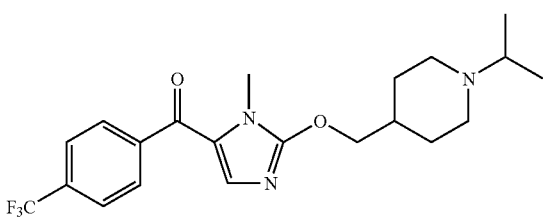

[2-(1-isopropyl-piperidin-4-ylmethoxy)-3-methyl-3H-imidazol-4-yl]-(4-trifluoromethyl-phenyl)-methanone;

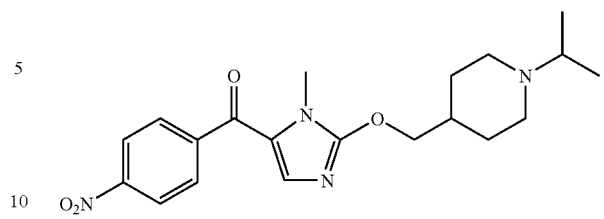

[2-(1-Isopropyl-piperidin-4-ylmethoxy)-3-methyl-3H-imidazol-4-yl]-(4-nitro-phenyl)-methanone;

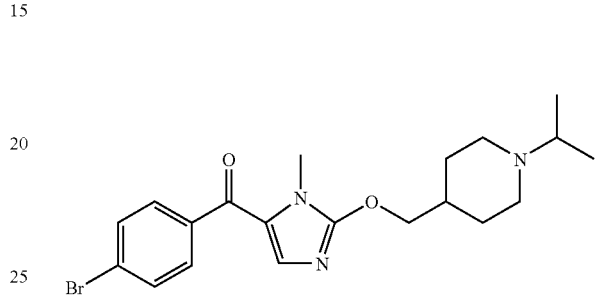

(4-Bromophenyl)-[2-(1-isopropyl-piperidin-4-yl-methoxy)-3-methyl-3H-imidazol-4-yl]-methanone;

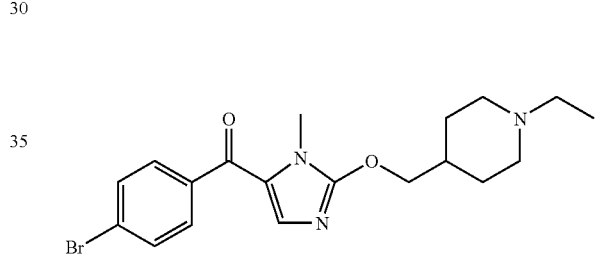

(4-Bromophenyl)-[2-(1-ethyl-piperidin-4-ylmethoxy)-3-methyl-3H-imidazol-4-yl]-methanone;

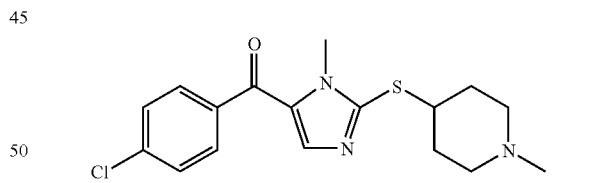

(4-Chlorophenyl)-[3-methyl-2-(1-methyl-piperidin-4-yl-sulfanyl)-3H-imidazol-4-yl]-methanone;

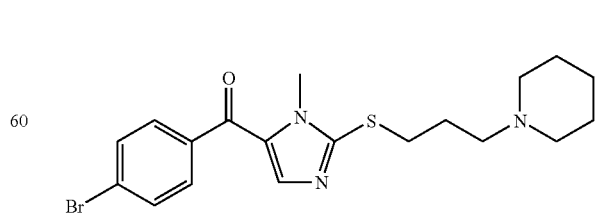

(4-Bromophenyl)-[3-methyl-2-(3-piperidin-1-yl-propyl-sulfanyl)-3H-imidazol-4-yl methanone;

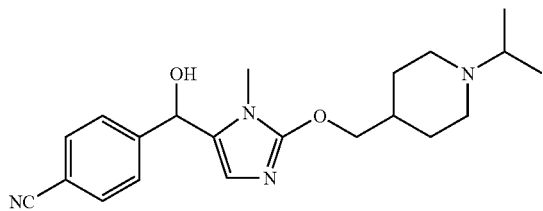

4-{Hydroxy-[2-(1-isopropyl-piperidin-4-ylmethoxy)-3-methyl-3H-imidazol-4-yl]-methyl}-benzonitrile; and

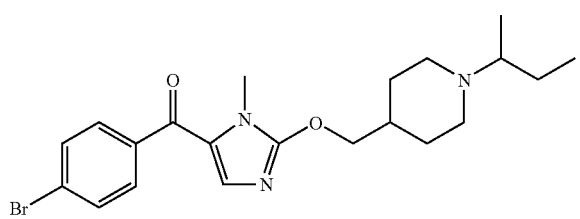

(4-Bromophenyl)-[2-(1-sec-butyl-piperidin-4-yl-methoxy)-3-methyl-3H-imidazol-4-yl]-methanone.

Additional embodiments of this invention provide methods of making a compound of formula (I), a pharmaceutically acceptable salt, ester, ether, N-oxide, amide, hydrate, solvate or isotopically labeled form thereof, according to Scheme I.1, wherein at least one of the following is satisfied:

said at least one of a PHA and an EFA is a perhaloalkane;
said at least one of a PHA and an EFA is a perhalo$C_{2-6}$ alkane;
said at least one of a PHA and an EFA is a perhalo$C_{2-4}$ alkane;
said at least one of a PHA and an EFA is a perchloro$C_{2-6}$ alkane;
said at least one of a PHA and an EFA is a perchloro$C_{2-4}$ alkane;
said at least one of a PHA and an EFA is hexachloroethane;
said at least one of a PHA and an EFA is at least one of 1-chloromethyl-4-fluoro-1,4-diazoniabicyclo[2.2.2]octane bis-(tetrafluoroborate); N-fluorobenzenesulfonamide; N-fluoropyridinium triflate; N-fluoroquiniclidinium triflate and mixtures thereof;
said base is an organolithium compound;
said base is one of LDA, LiHMDS, t-BuLi, sec-BuLi, n-BuLi, and mixtures thereof;
said base is n-BuLi;
$Q^1$ is selected from the group consisting of $C_{1-7}$alkyl, $C_{1-7}$haloalkyl and $C_{2-7}$alkenyl;
wherein $Q^1$ may be substituted with one or more substituents selected from the group consisting of halo, cyano, hydroxy, $OR^{11}$, $C_{1-5}$alkyl, $C_{1-5}$haloalkyl, $C_{2-5}$alkenyl, nitro, amino ($H_2N-$), $R^{11}HN-$, $R^{11}R^{12}N-$, amido ($H_2NC(O)$), $R^{11}HNC(O)$, $R^{11}R^{12}NC(O)$ and $R^{11}OC$(O), and wherein $R^{11}$ and $R^{12}$ are independently $C_{1-6}$alkyl, $C_{1-6}$haloalkyl or $C_{2-6}$alkenyl;
$Q^1$ is $-Lnk_1-C(RR^1)(AR)-Lnk_2-N^+(QS^1)(QS^2)(QS^3)$, wherein $Lnk_1$ is a bond or $C_{2-4}$alkylene, optionally substituted with at least one of $C_{1-4}$alkyl, halo$C_{1-4}$alkyl, $C_{1-4}$alkoxy, halo$C_{1-4}$alkoxy, fluoro, chloro, bromo, iodo, and cyano;

$RR^1$ is H or $C_{1-6}$alkyl, optionally substituted with at least one of $C_{1-4}$alkyl, halo$C_{1-4}$alkyl, $C_{1-4}$alkoxy, halo$C_{1-4}$alkoxy, fluoro, chloro, bromo, iodo, and cyano;
AR is phenyl, naphthyl, benzyl, thienyl, benzo[b]thienyl, or indolyl, each of which is optionally substituted with 1 to 3 substituents, each of said substituents independently selected from $C_{1-4}$alkyl, halo$C_{1-4}$alkyl, $C_{1-4}$alkoxy, halo$C_{1-4}$alkoxy, fluoro, chloro, bromo, iodo, and cyano, or AR is 1,3-benzodioxolan-4 or 5-yl or 1,4-benzodioxan-5 or 6-yl;
$Lnk_2$ is a bond or $C_{2-4}$alkylene, optionally substituted with at least one of $C_{1-4}$alkyl, halo$C_{1-4}$alkyl, $C_{1-4}$alkoxy, halo$C_{1-4}$alkoxy, fluoro, chloro, bromo, iodo, and cyano; and
each of $QS^1$, $QS^2$, and $QS^3$ is independently selected from H, $C_{1-6}$alkyl, optionally substituted with at least one of $C_{1-4}$alkyl, halo$C_{1-4}$alkyl, $C_{1-4}$alkoxy, halo$C_{1-4}$alkoxy, fluoro, chloro, bromo, iodo, and cyano, or any two of $QS^1$, $QS^2$, and $OS^3$ are taken together to form, together with the attachment quaternary nitrogen member, a heterocycle, while the third is selected from $C_{1-6}$alkyl, optionally substituted with at least one of $C_{1-4}$alkyl, $C_{1-4}$alkoxy, fluoro, chloro, bromo, iodo, and cyano, or the three $QS^1$, $QS^2$, and $QS^3$ are taken together to form, together with the attachment quaternary nitrogen member, optionally substituted quinuclidinium

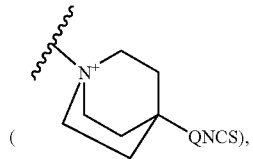

(QNCS), wherein QNCS is H or one of $C_{1-6}$alkyl, phenyl, naphthyl, benzyl, pyridyl, thienyl, $C_{3-7}$cycloalkyl, each of which being optionally substituted with at least one of $C_{1-4}$alkyl, halo$C_{1-4}$alkyl, $C_{1-4}$alkoxy, halo$C_{1-4}$alkoxy, fluoro, chloro, bromo, iodo, and cyano;
$Q^1$ is methyl;
Hal is chloro;
said reacting compound of formula (A) with a base is performed at a temperature from about 0° C. to about −100° C.;
said reacting compound of formula (A) with a base is performed at a temperature from about −20° C. to about −90° C.;
said reacting compound of formula (A) with a base is performed at a temperature of about −78° C.

Additional embodiments of this invention provide methods of making a compound of formula (I) a pharmaceutically acceptable salt, ester, ether, N-oxide, amide, hydrate, solvate or isotopically labeled form thereof, according to Scheme 1.2, wherein at least one of the following is satisfied:

the compound of formula (I) is the compound of formula (11)

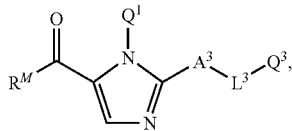

(11)

wherein $R^M$, $Q^1$, $A^3$, $L^3$, and $Q^3$ are as defined for formula (I);
$Q^1$ is selected from the group consisting of $C_{1-7}$alkyl and $C_{2-7}$alkenyl; wherein $Q^1$ may be substituted with one or more substituents selected from the group consisting of halo, cyano, hydroxy, $OR^{11}$, $C_{1-5}$alkyl, $C_{1-5}$haloalkyl, $C_{2-5}$alkenyl, nitro, amino ($H_2N$—), $R^{11}HN$—, $R^{11}R^{12}N$—, amido ($H_2NC(O)$), $R^{11}HNC(O)$, $R^{11}R$ $NC(O)$ and $R^{11}OC(O)$, and wherein $R^{11}$ and $R^{12}$ are independently $C_{1-6}$alkyl, $C_{1-6}$haloalkyl or $C_{2-6}$alkenyl;
$Q^1$ is -Lnk$_1$-C(RR$^1$)(AR)-Lnk$_2$-N$^+$(QS$^1$)(QS$^2$)(QS$^3$), wherein Lnk$_1$ is a bond or $C_{2-4}$alkylene, optionally substituted with at least one of $C_{1-4}$alkyl, halo$C_{1-4}$alkyl, $C_{1-4}$alkoxy, halo$C_{1-4}$alkoxy, fluoro, chloro, bromo, iodo, and cyano;
RR$^1$ is H or $C_{1-6}$alkyl, optionally substituted with at least one of $C_{1-4}$alkyl, halo$C_{1-4}$alkyl, $C_{1-4}$alkoxy, halo$C_{1-4}$ alkoxy, fluoro, chloro, bromo, iodo, and cyano;
AR is phenyl, naphthyl, benzyl, thienyl, benzo[b]thienyl, or indolyl, each of which is optionally substituted with 1 to 3 substituents, each of said substituents independently selected from $C_{1-4}$alkyl, halo$C_{1-4}$alkyl, $C_{1-4}$alkoxy, halo$C_{1-4}$alkoxy, fluoro, chloro, bromo, iodo, and cyano, or AR is 1,3-benzodioxolan-4 or 5-yl or 1,4-benzodioxan-5 or 6-yl;
Lnk$_2$ is a bond or $C_{2-4}$alkylene, optionally substituted with at least one of $C_{1-4}$alkyl, halo$C_{1-4}$alkyl, $C_{1-4}$alkoxy, halo$C_{1-4}$alkoxy, fluoro, chloro, bromo, iodo, and cyano; and
each of QS$^1$, QS$^2$, and QS$^3$ is independently selected from H, $C_{1-6}$alkyl, optionally substituted with at least one of $C_{1-4}$alkyl, halo$C_{1-4}$alkyl, $C_{1-4}$alkoxy, halo$C_{1-4}$alkoxy, fluoro, chloro, bromo, iodo, and cyano, or any two of QS$^1$, QS$^2$, and QS$^3$ are taken together to form, together with the attachment quaternary nitrogen member, a heterocycle, while the third is selected from $C_{1-6}$alkyl, optionally substituted with at least one of $C_{1-4}$alkyl, $C_{1-4}$alkoxy, fluoro, chloro, bromo, iodo, and cyano, or
the three QS$^1$, QS$^2$, and QS$^3$ are taken together to form, together with the attachment quaternary nitrogen member, optionally substituted quinuclidinium

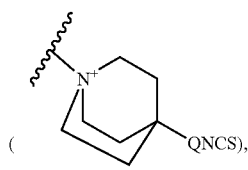

(QNCS), wherein QNCS is H or one of $C_{1-6}$alkyl, phenyl, naphthyl, benzyl, pyridyl, thienyl, $C_{3-7}$cycloalkyl, each of which being optionally substituted with at least one of $C_{1-4}$alkyl, halo$C_{1-4}$ alkyl, $C_{1-4}$alkoxy, halo$C_{1-4}$alkoxy, fluoro, chloro, bromo, iodo, and cyano; $Q^1$ is methyl;

Hal in Scheme I.2 is chosen as the same as Hal in Scheme I.1;
Hal is chloro;
a is a double bond;
O' is O;
a is a single bond;
a is a single bond and O' is OH;
said base is an organolithium compound;
said base is one of LDA, LiHMDS, t-BuLi, sec-BuLi, n-BuLi, and mixtures thereof;
said base is n-BuLi;
said electrophile (D) is one of:
(D) is O═C(X)R, with a being a single bond, X being H, O' being OH, and R being $R^M$;
(D) is O═C(X)R, with a being a double bond, X being —N(OMe)Me or —N(Me)$_2$, O' being O, and R being $R^M$;
(D) is $CO_2$, with a being a double bond, and O' being O, R being hydroxy; and
(D) is O═C(X)R, with a being a double bond, O' being O, R being $R^M$, X being fluoro, chloro, bromo or iodo;
and $R^M$ is defined as indicated herein;
said reacting compound of formula (B) with a base is performed at a temperature from about 0° C. to about −100° C.;
said reacting compound of formula (B) with a base is performed at a temperature from about −20° C. to about −90° C.;
said reacting compound of formula (B) with a base is performed at a temperature of about −78° C.;
said base in Scheme 1.2 is the same base as in Scheme I.1;
R is one of phenyl or halophenyl;
R is benzyl substituted with one of cyano, nitro, and trifluoromethyl;
R is phenyl substituted with at least two halo groups;
a is a double bond and O' is N—OH;
further comprising at least one of the following features for a nucleophilic substitution on compound (C):
reacting compound (41) with a deprotonated nucleophile, wherein O' is O, a is a double bond, R is $R^M$, and said nucleophile is H-A$^3$-L$^3$-Q$^3$;
reacting compound (41) with a deprotonated oxygen or sulfur nucleophile, wherein O' is O, a is a double bond, R is $R^M$, and said nucleophile is H-A$^3$-L$^3$O$^3$, with A$^3$ being O or S;
reacting compound (41) with a deprotonated oxygen or sulfur nucleophile, wherein O' is O, a is a double bond, R is $R^M$, and said nucleophile is H-A$^3$-L$^3$-Q$^3$, with A$^3$-L$^3$-Q$^3$ being one of 1-isopropyl-piperidin-4-ylmethoxy, 3-dimethylamino-propylsulfanyl, 2-(1-methylpyrrolidin-2-yl)-ethylsulfanyl, 1-isopropyl-piperidin-4-ylsulfanyl, 3-piperidin-1-yl-propylsulfanyl, 3-dimethylamino-propylsulfanyl, 1-ethyl-piperidin-4-ylmethoxy, 1-methyl-piperidin-4-ylsulfanyl, and 1-sec-butyl-piperidin-4-ylmethoxy;
treating compound (41) with a nucleophilic primary amine H$_2$N-L$^3$-Q$^3$ in the presence of a base, wherein O' is O, a is a double bond, and R is $R^M$;
treating compound (41) with a nucleophilic secondary amine HR$^3$N-L$^3$O$^3$ in the presence of a base, wherein O' is O, a is a double bond, and R is $R^M$;
performing hydroxy protection, where O' is OH and a is a single bond, to form a hydroxy-protected compound, reacting said hydroxy-protected compound with a deprotonated nucleophile, wherein R is $R^M$, and said nucleophile is H-A$^3$-L$^3$-Q$^3$, and optionally performing hydroxy deprotection;

performing hydroxy protection, where O' is OH and a is a single bond to form a hydroxy-protected compound, reacting said hydroxy-protected compound with a deprotonated oxygen or sulfur nucleophile, wherein R is $R^M$, and said nucleophile is H-$A^3$-$L^3O^3$, with $A^3$ being O or S, and optionally performing hydroxy deprotection;

treating compound (41) with a nucleophilic primary amine $H_2N$-$L^3$-$Q^3$ in the presence of a base, wherein O' is OH, a is a single bond, and R is $R^M$, and optionally further comprising at least one of hydroxy protection, and hydroxy protection with subsequent hydroxy deprotection;

treating compound (41) with a nucleophilic secondary amine $HR^3N$-$L^3$-$Q^3$ in the presence of a base, wherein O' is OH, a is a single bond, and R is $R^M$, and optionally further comprising at least one of hydroxy protection, and hydroxy protection with subsequent hydroxy deprotection;

treating compound (41) with a deprotonated sulfur nucleophile reagent H-$A^3$-$L^3$-$Q^4$, wherein $A^3$ is S, $Q^4$ is hydrogen, O' is O, and a is a double bond, to form compound (5b), and optionally further comprising treating compound (5b) with an oxidizing agent resulting in an intermediate compound (10), and optionally further comprising treating intermediate compound (10) with a nucleophile reagent H-$A^3$-$L^3$-$Q^3$, wherein $L^3$ of the reagent H-$A^3$-$L^3$-$Q^3$ is independent of $L^3$ of formula (5b) and formula (10), in the presence of a base yielding said compound of formula (11).

Additional embodiments of this invention provide methods of making a compound of formula (I) a pharmaceutically acceptable salt, ester, ether, N-oxide, amide, hydrate, solvate or isotopically labeled form thereof, with a group Hal that is stable to metal exchange conditions as described herein, wherein at least one of the following is satisfied:

said blocking the C-2 position is performed according to at least any one of the features that refer to Scheme I.1 in the additional embodiments of methods of making a compound of formula (I) given herein;

said reacting said compound of formula (B) with a base and said performing an addition are performed according to at least any one of the features that refer to Scheme I.2 in the additional embodiments of methods of making a compound of formula (I) given herein; and said performing a nucleophilic substitution is performed according to at least any one of the features that refer to said nucleophilic substitution on compound (C).

Where the compounds according to this invention have at least one chiral center, they may accordingly exist as enantiomers. Where the compounds possess two or more chiral centers, they may additionally exist as diastereomers. Where the compounds according to this invention have at least one double bond, they may accordingly exist as geometric isomers, for example, E- and Z-isomers. It is to be understood that all such isomers and mixtures thereof are encompassed within the scope of the present invention. It is also understood that certain compounds of the present invention may possess structural arrangements that permit the structure to exist as tautomers, and as such, these tautomers are intended to be included in the present invention. Furthermore, some of the crystalline forms for the compounds may exist as polymorphs and as such are intended to be included in the present invention. In addition, certain compounds referred to herein can exist in solvated as well as unsolvated forms. It is understood that this invention encompasses all such solvated and unsolvated forms that possess the activity that characterizes the compounds of this invention.

Compounds according to the present invention that have been modified to be detectable by some analytic technique are also within the scope of this invention. An example of such compounds is an isotopically labeled compound, such as $^{11}C$, $^{13}N$, $^{15}O$ or $^{18}F$ isotopically labeled compound, which may be used as a probe in detection and/or imaging techniques, such as positron emission tomography (PET) and single-photon emission computed tomography (SPECT). Of particular interest are $^{18}F$-labeled compounds, which may be prepared from nitro-substituted, electron-deficient phenyl precursors by nucleophilic aromatic substitution using [$^{18}F$]fluoride ion. Nucleophilic fluorinations may be performed under anhydrous conditions in an inert atmosphere in a non-hydrolytic solvent, usually in the presence of a phase transfer agent, for example, Kryptofix 2.2.2® or tetra-N-butylammonium hydrogen carbonate (Ding, Y.-S., et al. *J. Med. Chem.*, 1991, 34, 767-771). Another example of such compounds is an isotopically labeled compound, such as a deuterium and/or tritium labeled compound that may be used in reaction kinetic studies. In the present invention, an appropriately labeled compound provides a useful molecular probe and diagnostic tool for studying central nervous system (CNS) disorders.

The present invention also provides prodrugs of the compounds of this invention. As used herein, "prodrugs" refer to compounds that are readily convertible in vivo into a compound of formula (I). Thus, in the methods of treatment of the present invention, the term "administering" shall encompass any one of the administration of at least one of the compounds according to this invention and the administration of at least one compound that converts to one or more compound according to this invention in vivo after administration to the subject. Conventional procedures for the selection and preparation of suitable prodrug derivatives are described, for example, in "Design of Prodrugs", ed. H. Bundgaard, Elsevier, 1985.

Reference to a compound herein stands for a reference to any one of: (a) the actually recited form of such compound, and (b) any of the forms of such compound in the medium in which the compound is being considered when named. For example, reference herein to a compound such as R—COOH, encompasses reference to any one of, for example, R—COOH$_{(s)}$, R—COOH$_{(sol)}$, and R—COO$^-_{(sol)}$. In this example, R—COOH$_{(s)}$ refers to the solid compound, as it could be for example in a tablet or some other solid pharmaceutical composition or preparation; R—COOH$_{(sol)}$ refers to the undissociated form of the compound in a solvent, such as water; and R—COO$^-_{(sol)}$ refers to the dissociated form of the compound in a solvent, such as the dissociated form of the compound in an aqueous environment, whether such dissociated form derives from R—COOH, from a salt thereof, or from any other entity that yields R—COO$^-$ upon dissociation in the medium being considered. In another example, an expression such as "exposing an entity to compound of formula R—COOH" refers to the exposure of such entity to the form, or forms, of the compound R—COOH that exists, or exist, in the medium in which such exposure takes place. In this regard, if such entity is for example in an aqueous environment, it is understood that the compound R—COOH is in such same medium, and therefore the entity is being exposed to species such as R—COOH$_{(aq)}$ and/or R—COO$^-_{(aq)}$, where the subscript "(aq)" stands for "aqueous" according to its conventional meaning in chemistry and biochemistry. A carboxylic acid functional group has been chosen in these nomenclature examples; this choice is not intended, however, as a limitation but it is merely an illustration. It is understood that analogous examples can be provided in terms of other functional groups, including but not limited to hydroxyl, basic nitrogen members, such as those in amines, and any other group that interacts or transforms according to known manners in the medium that contains the compound. Such interactions and transformations include, but are not limited to, dissociation, association, tautomerism, solvolysis, including hydrolysis, solvation, including hydration, protonation, and deprotonation. No further examples in this regard are provided, herein because these interactions and transformations in a given medium are known by any one of ordinary skill in the art.

Table of Acronyms and Abbreviations

| Term | Acronym/Abbreviation |
|---|---|
| acetic anhydride | $Ac_2O$ |
| acetic acid | AcOH |
| Tert-butyloxycarbonyl | t-BOC |
| n-butyl lithium | n-BuLi |
| tert-butyl lithium | t-BuLi |
| n- or 1-butanol | BuOH |
| meta- or 3-chloroperoxybenzoic acid | mCPBA |
| 1,2-dimethoxyethane | DME |
| N,N-dimethylformamide | DMF |
| Dimethylsulfoxide | DMSO |
| Triethylamine | $Et_3N$ |
| diethyl ether | $Et_2O$ |
| Ethanol | EtOH |
| Potassium tert-butoxide | KOt-Bu |
| Lithium diisopropylamide | LDA |
| Lithium bis(trimethylsilyl)amide | LHMDS |
| Lithium tetramethylpiperidide | LTMP |
| Methylamine | $MeNH_2$ |
| Methanol | MeOH |
| Sodium triacetoxyborohydride | $NaBH(OAc)_3$ |
| sodium ethoxide | NaOEt |
| Sodium methoxide | NaOMe |
| Pyridinium chlorochromate | PCC |
| Pyridinium dichromate | PDC |
| tetrakis(triphenylphosphine)palladium(0) | $(Ph_3P)_4Pd$ |
| Diphenyldisulfide | PhSSPh |
| room temperature | rt |
| Trifluoroacetic acid | TFA |
| Tetrahydrofuran | THF |

Compounds according to the present invention may be made according to processes within the skill of the art and/or according to processes of this invention, such as those described in the schemes and examples that follow and by matrix or combinatorial methods. To obtain the various compounds herein, starting materials may be employed that carry the ultimately desired substituents though the reaction scheme with or without protection as appropriate. Starting materials may be obtained from commercial sources or synthesized by methods known to one skilled in the art. Alternatively, it may be necessary to employ, in the place of the ultimately desired substituent, a suitable group, which may be carried through the reaction scheme and replaced as appropriate with the desired substituent. Those of ordinary skill in the art will be able to modify and adapt the guidance provided herein to make compounds according to the present invention.

Embodiments of processes illustrated herein include, when chemically meaningful, one or more steps such as hydrolysis, halogenation, protection, and deprotection. These steps can be implemented in light of the teachings provided herein and the ordinary skill in the art.

During any of the processes for preparation of the compounds of the present invention, it may be necessary and/or desirable to protect sensitive or reactive groups on any of the molecules concerned. In addition, compounds of this invention may be modified by using protecting groups; such compounds, precursors, or prodrugs are also within the scope of the invention. This modification may be achieved by means of conventional protecting groups, such as those described in "Protective Groups in Organic Chemistry", ed. J. F. W. McOmie, Plenum Press, 1973; and T. W. Greene & P. G. M. Wuts, "Protective Groups in Organic Synthesis", $3^{rd}$ ed., John Wiley & Sons, 1999. The protecting groups may be removed at a convenient subsequent stage using methods known from the art.

Hydroxyl Protecting Groups

Protection for the hydroxyl group includes methyl ethers, substituted methyl ethers, substituted ethyl ethers, substituted benzyl ethers, and silyl ethers.

Substituted Methyl Ethers. Examples of substituted methyl ethers include methyoxymethyl, methylthiomethyl, t-butylthiomethyl, (phenyldimethylsilyl)methoxymethyl, benzyloxymethyl, p-methoxybenzyloxymethyl, (4-methoxyphenoxy)methyl, guaiacolmethyl, t-butoxymethyl, 4-pentenyloxymethyl, siloxymethyl, 2-methoxyethoxymethyl, 2,2,2-trichloroethoxymethyl, bis(2-chloroethoxy)methyl, 2-(trimethylsilyl)ethoxymethyl, tetrahydropyranyl, 3-bromotetrahydropyranyl, tetrahydrothiopyranyl, 1-methoxycyclohexyl, 4-methoxytetrahydropyranyl, 4-methoxytetrahydrothiopyranyl, 4-methoxytetrahydrothiopyranyl S,S-dioxido, 1-[(2-chloro-4-methyl)phenyl]-4-methoxypiperidin-4-yl, 1,4-dioxan-2-yl, tetrahydrofuranyl, tetrahydrothiofuranyl and 2,3,3a,4,5,6,7,7a-octahydro-7,8,8-trimethyl-4,7-methanobenzofuran-2-yl.

Substituted Ethyl Ethers. Examples of substituted ethyl ethers include 1-ethoxyethyl, 1-(2-chloroethoxy)ethyl, 1-methyl-1-methoxyethyl, 1-methyl-1-benzyloxyethyl, 1-methyl-1-benzyloxy-2-fluoroethyl, 2,2,2-trichloroethyl, 2-trimethylsilylethyl, 2-(phenylselenyl)ethyl, t-butyl, allyl, p-chlorophenyl, p-methoxyphenyl, 2,4-dinitrophenyl, and benzyl.

Substituted Benzyl Ethers. Examples of substituted benzyl ethers include p-methoxybenzyl, 3,4-dimethoxybenzyl, onitrobenzyl, p-nitrobenzyl, p-halobenzyl, 2,6-dichlorobenzyl, p-cyanobenzyl, p-phenylbenzyl, 2- and 4-picolyl, 3-methyl-2-picolyl N-oxido, diphenylmethyl, p, p'-dinitrobenzhydryl, 5-dibenzosuberyl, triphenylmethyl, x-naphthyldiphenylmethyl, p-methoxyphenyidiphenylmethyl, di(p-methoxyphenyl)phenylmethyl, tri(p-methoxyphenyl)methyl, 4-(4'-bromophenacyloxy)phenyldiphenylmethyl, 4,4',4"-tris(4,5-dichlorophthalimidophenyl)methyl, 4,4',4"-tris(levulinoyloxyphenyl)methyl, 4,4',4"-tris(benzoyloxyphenyl)methyl, 3-(Imidazol-1-ylmethyl)bis(4', 4"-dimethoxyphenyl)methyl, 1,1-bis(4-methoxyphenyl)-1'-pyrenylmethyl, 9-anthryl, 9-(9-phenyl)xanthenyl, 9-(9-phenyl-10-oxo)anthryl, 1,3-benzodithiolan-2-yl, and benzisothiazolyl S,S-dioxido.

Silyl Ethers. Examples of silyl ethers include trimethylsilyl, triethylsilyl, triisopropylsilyl, dimethylisopropylsilyl, diethylisopropylsilyl, dimethylthexylsilyl, t-butyldimethylsilyl, t-butyldiphenylsilyl, tribenzylsilyl, tri-p-xylylsilyl, triphenylsilyl, diphenylmethylsilyl, and t-butylmethoxyphenylsilyl.

Esters. In addition to ethers, a hydroxyl group may be protected as an ester. Examples of esters include formate, benzoylformate, acetate, chloroacetate, dichloroacetate, trichloroacetate, trifluoroacetate, methoxyacetate, triphenylmethoxyacetate, phenoxyacetate, p-chlorophenoxyacetate, p-P-phenylacetate, 3-phenylpropionate, 4-oxopentanoate(levulinate), 4,4-(ethylenedithio)pentanoate, pivaloate, adamantoate, crotonate, 4-methoxycrotonate, benzoate, p-phenylbenzoate, 2,4,6-trimethylbenzoate(mesitoate).

Carbonates. Examples of carbonates include methyl, 9-fluorenylmethyl, ethyl, 2,2,2-trichloroethyl, 2-(trimethylsilyl)ethyl, 2-(phenylsulfonyl)ethyl, 2-(triphenylphosphonio) ethyl, isobutyl, vinyl, allyl, p-nitrophenyl, benzyl, p-methoxybenzyl, 3,4-dimethoxybenzyl, onitrobenzyl, prnitrobenzyl, S-benzyl thiocarbonate, 4-ethoxy-1-naphthyl, and methyl dithiocarbonate.

Assisted Cleavage. Examples of assisted cleavage include 2-iodobenzoate, 4-azidobutyrate, 4-nitro-4-methylpentanoate, o-(dibromomethyl)benzoate, 2-formylbenzenesulfonate, 2-(methylthiomethoxy)ethyl carbonate, 4-(methylthiomethoxy)butyrate, and 2-(methylthiomethoxymethyl) benzoate.

Miscellaneous Esters. Examples of miscellaneous esters include 2,6-dichloro-4-methylphenoxyacetate, 2,6-dichloro-4-(1,1,3,3-tetramethylbutyl)phenoxyacetate, 2,4-bis(1,1-dimethylpropyl)phenoxyacetate, chlorodiphenylacetate, isobutyrate, monosuccinoate, (E)-2-methyl-2-butenoate (tigloate), o-(methoxycarbonyl)benzoate, p-P-benzoate, α-naphthoate, nitrate, alkyl N,N,N',N'-tetramethylphosphorodiamidate, N-phenylcarbamate, borate, dimethylphosphinothioyl, and 2,4-dinitrophenylsulfenate.

Sulfonates. Examples of sulfonates include sulfate, methanesulfonate(mesylate), benzylsulfonate, and tosylate.

Protection for 1,2- and 1,3-Diols

Cyclic Acetals and Ketals. Examples of cyclic acetals and ketals include methylene, ethylidene, 1-t-butylethylidene, 1-phenylethylidene, (4-methoxyphenyl)ethylidene, 2,2,2-trichloroethylidene, acetonide (isopropylidene), cyclopentylidene, cyclohexylidene, cycloheptylidene, benzylidene, p-methoxybenzylidene, 2,4-dimethoxybenzylidene, 3,4-dimethoxybenzylidene, and 2-nitrobenzylidene.

Cyclic Ortho Esters. Examples of cyclic ortho esters include methoxymethylene, ethoxymethylene, dimethoxymethylene, 1-methoxyethylidene, 1-ethoxyethylidine, 1,2-dimethoxyethylidene, α-methoxybenzylidene, 1-(N,N-dimethylamino)ethylidene derivative, α-(N,N-dimethylamino)benzylidene derivative, and 2-oxacyclopentylidene.

Silyl Derivatives. Examples of silyl derivatives include di-t-butylsilylene group, and 1,3-(1,1,3,3-tetraisopropyidisiloxanylidene) derivative.

Amino Protecting Groups

Protection for the amino (or alkylamino) group includes carbamates, amides, and special —NH protective groups. Examples of carbamates include methyl and ethyl carbamates, substituted ethyl carbamates, assisted cleavage carbamates, photolytic cleavage carbamates, urea-type derivatives, and miscellaneous carbamates.

Carbamates. Examples of methyl and ethyl carbamates include methyl and ethyl, 9-fluorenylmethyl, 9-(2-sulfo)fluorenylmethyl, 9-(2,7-dibromo)fluorenylmethyl, 2,7-di-t-butyl-[9-(10,10-dioxo-10,10,10-tetrahydrothioxanthyl)] methyl, and 4-methoxyphenacyl.

Substituted Ethyl. Examples of substituted ethyl carbamates include 2,2,2-trichloroethyl, 2-trimethylsilylethyl, 2-phenylethyl, 1-(1-adamantyl)-1-methylethyl, 1,1-dimethyl-2-haloethyl, 1,1-dimethyl-2,2-dibromoethyl, 1,1-dimethyl-2,2,2-trichloroethyl, 1-methyl-1-(4-biphenylyl)ethyl, 1-(3,5-di-t-butylphenyl)-1-methylethyl, 2-(2'- and 4'-pyridyl)ethyl, 2-(N,N-dicyclohexylcarboxamido)ethyl, t-butyl, 1-adamantyl, vinyl, allyl, 1-isopropylallyl, cinnamyl, 4-nitrocinnamyl, 8-quinolyl, N-hydroxypiperidinyl, alkyldithio, benzyl, p-methoxybenzyl, R-nitrobenzyl, p-bromobenzyl, p-chlorobenzyl, 2,4-dichlorobenzyl, 4-methylsulfinylbenzyl, 9-anthrylmethyl and diphenylmethyl.

Assisted Cleavage. Examples of assisted cleavage include 2-methylthioethyl, 2-methylsulfonylethyl, 2-(ptoluenesulfonyl)ethyl, [2-(1,3-dithianyl)]methyl, 4-methylthiophenyl, 2,4-dimethylthiophenyl, 2-phosphonioethyl, 2-triphenylphosphonioisopropyl, 1,1-dimethyl-2-cyanoethyl, m-chloro-p-acyloxybenzyl, p-(dihydroxyboryl)benzyl, 5-benzisoxazolylmethyl, and 2-(trifluoromethyl)-6-chromonylmethyl.

Photolytic Cleavage. Examples of photolytic cleavage include m-nitrophenyl, 3,5-dimethoxybenzyl, onitrobenzyl, 3,4-dimethoxy-6-nitrobenzyl, and phenyl(o-nitrophenyl)methyl.

Urea-Type Derivatives. Examples of urea-type derivatives include phenothiazinyl-(10)-carbonyl derivative, N'-p-toluenesulfonylaminocarbonyl, and N'-phenylaminothiocarbonyl.

Miscellaneous Carbamates. Examples of miscellaneous carbamates include t-amyl, S-benzyl thiocarbamate, p-cyanobenzyl, cyclobutyl, cyclohexyl, cyclopentyl, cyclopropylmethyl, p-decyloxybenzyl, diisopropylmethyl, 2,2-dimethoxycarbonylvinyl, o-(N, N-dimethylcarboxamido) benzyl, 1,1-dimethyl-3-(N,N-dimethylcarboxamido)propyl, 1,1-dimethylpropynyl, di(2-pyridyl)methyl, 2-furanylmethyl, 2-iodoethyl, isobornyl, isobutyl, isonicotinyl, p-(p'-methoxyphenylazo)benzyl, 1-methylcyclobutyl, 1-methylcyclohexyl, 1-methyl-1-cyclopropylmethyl, 1-methyl-1-(3, 5-dimethoxyphenyl)ethyl, 1-methyl-1-(p-phenylazophenyl) ethyl, 1-methyl-1-phenylethyl, 1-methyl-1-(4-pyridyl)ethyl, phenyl, p-(phenylazo)benzyl, 2,4,6-tri-t-butylphenyl, 4-(trimethylammonium)benzyl, and 2,4,6-trimethylbenzyl.

Examples of Amides Include:

Amides. N-formyl, N-acetyl, N-chloroacetyl, N-trichloroacetyl, N-trifluoroacetyl, N-phenylacetyl, N-3-phenylpropionyl, N-picolinoyl, N-3-pyridylcarboxamide, N-benzoylphenylalanyl derivative, N-benzoyl, N-p-phenylbenzoyl.

Assisted Cleavage. N-onitrophenylacetyl, N-onitrophenoxyacetyl, N-acetoacetyl, (N'-dithiobenzyloxycarbonylamino)acetyl, N-3-(p-hydroxyphenyl)propionyl, N-3-(onitrophenyl)propionyl, N-2-methyl-2-(o-nitrophenoxy) propionyl, N-2-methyl-2-(ophenylazophenoxy)propionyl, N-4-chlorobutyryl, N-3-methyl-3-nitrobutyryl, N-o-nitrocinnamoyl, N-acetylmethionine derivative, N-o-nitrobenzoyl, N-o-(benzoyloxymethyl)benzoyl, and 4,5-diphenyl-3-oxazolin-2-one.

Cyclic Imide Derivatives. N-phthalimide, N-dithiasuccinoyl, N-2,3-diphenylmaleoyl, N-2,5-dimethylpyrrolyl, N-1, 1,4,4-tetramethyldisilylazacyclopentane adduct, 5-substituted 1,3-dimethyl- 1,3,5-triazacyclohexan-2-one, 5-substituted 1,3-dibenzyl-1,3,5-triazacyclohexan-2-one, and 1-substituted 3,5-dinitro-4-pyridonyl.

Special—NH Protective Groups

Examples of special NH protective groups include:

N-Alkyl and N-Aryl Amines. N-methyl, N-allyl, N-[2-(trimethylsilyl)ethoxy]methyl, N-3-acetoxypropyl, N-(1-isopropyl-4-nitro-2-oxo-3-pyrrolin-3-yl), quaternary ammonium salts, N-benzyl, N-4-methoxybenzyl, N-di(4-methoxyphenyl)methyl, N-5-dibenzosuberyl, N-triphenylmethyl, N-(4-methoxyphenyl)diphenylmethyl, N-9-phenylfluorenyl, N-2,7-dichloro-9-fluorenylmethylene, N-ferrocenylmethyl, and N-2-picolylamine N'-oxide.

Imine Derivatives. N-1,1-dimethylthiomethylene, N-benzylidene, N-p-methoxybenzylidene, N-diphenylmethylene, N-[(2-pyridyl)mesityl]methylene, and N—(N',N'-dimethylaminomethylene).

Examples of acyl groups that can be used to protect an amino, or alkylamino, group include an alkanoyl group, such as acetyl, an alkoxycarbonyl group, such as methoxycarbonyl, ethoxycarbonyl, and t-butoxycarbonyl, an arylmethoxycarbonyl group, such as benzyloxycarbonyl, and an aroyl group, such as benzoyl. As known in the conventional practice of these protection reactions, deprotection conditions vary with the protecting group. Groups such as an alkanoyl, alkoxycarbonyl, or aroyl may be removed, for example, by hydrolysis with a suitable base, such as an alkali metal hydroxide. Other groups, such as a t-butoxycarbonyl group, may be removed by, for example, treatment with an acid, such as hydrochloric, sulfuric, phosphoric, or trifluoroacetic. Arylmethoxycarbonyl groups, such as benzyloxycarbonyl, may be removed by, for example, hydrogenation in the presence of a catalyst, such as palladium-on-carbon, or by treatment with a Lewis acid, such as boron tris(trifluoroacetate). A phthaloyl group protecting a primary amino group may be removed by, for example, treatment with an alkylamine, such as dimethylaminopropylamine, or with hydrazine.

Protection for the Carbonyl Group

Acyclic Acetals and Ketals. Examples of acyclic acetals and ketals include dimethyl, bis(2,2,2-trichloroethyl), dibenzyl, bis(2-nitrobenzyl) and diacetyl.

Cyclic Acetals and Ketals. Examples of cyclic acetals and ketals include 1,3-dioxanes, 5-methylene-1,3-dioxane, 5,5-dibromo-1,3-dioxane, 5-(2-pyridyl)-1,3-dioxane, 1,3-dioxolanes, 4-bromomethyl-1,3-dioxolane, 4-(3-butenyl)-1,3-dioxolane, 4-phenyl-1,3-dioxolane, 4-(2-nitrophenyl)-1,3-dioxolane, 4,5-dimethoxymethyl-1,3-dioxolane, O,O'-phenylenedioxy and 1,5-dihydro-3H-2,4-benzodioxepin.

Acyclic Dithio Acetals and Ketals. Examples of acyclic dithio acetals and ketals include S,S'-dimethyl, S,S'-diethyl, S,S'-dipropyl, S,S'-dibutyl, S,S'-dipentyl, S,S'-diphenyl, S,S'-dibenzyl and S,S'-diacetyl.

Cyclic Dithio Acetals and Ketals. Examples of cyclic dithio acetals and ketals include 1,3-dithiane, 1,3-dithiolane and 1,5-dihydro-3H-2,4-benzodithiepin.

Acyclic Monothio Acetals and Ketals. Examples of acyclic monothio acetals and ketals include O-trimethylsilyl-S-alkyl, O-methyl-S-alkyl or —S-phenyl and O-methyl-S-2-(methylthio)ethyl.

Cyclic Monothio Acetals and Ketals. Examples of cyclic monothio acetals and ketals include 1,3-oxathiolanes.

Miscellaneous Derivatives

O-Substituted Cyanohydrins. Examples of O-substituted cyanohydrins include O-acetyl, O-trimethylsilyl, O-1-ethoxyethyl and O-tetrahydropyranyl.

Substituted Hydrazones. Examples of substituted hydrazones include N,N-dimethyl and 2,4-dinitrophenyl.

Oxime Derivatives. Examples of oxime derivatives include O-methyl, O-benzyl and O-phenylthiomethyl.

Imines

Substituted Methylene Derivatives, Cyclic Derivatives. Examples of substituted methylene and cyclic derivatives include oxazolidines, 1-methyl-2-(1'-hydroxyalkyl)imidazoles, N,N'-dimethylimidazolidines, 2,3-dihydro-1,3-benzothiazoles, diethylamine adducts, and methylaluminum bis (2,6-di-t-butyl-4-methylphenoxide)(MAD)complex.

Monoprotection of Dicarbonyl Compounds

Selective Protection of α-and β-Diketones. Examples of selective protection of α-and β-diketones include enamines, enol acetates, enol ethers, methyl, ethyl, i-butyl, piperidinyl, morpholinyl, 4-methyl-1,3-dioxolanyl, pyrrolidinyl, benzyl, S-butyl, and trimethylsilyl.

Cyclic Ketals, Monothio and Dithio Ketals. Examples of cyclic ketals, monothio and dithio ketals include bismethylenedioxy derivatives and tetramethylbismethylenedioxy derivatives.

Protection for the Carboxyl Group

Esters

Substituted Methyl Esters. Examples of substituted methyl esters include 9-fluorenylmethyl, methoxymethyl, methylthiomethyl, tetrahydropyranyl, tetrahydrofuranyl, methoxyethoxymethyl, 2-(trimethylsilyl)ethoxymethyl, benzyloxymethyl, phenacyl, p-bromophenacyl, α-methylphenacyl, p-methoxyphenacyl, carboxamidomethyl, and N-phthalimidomethyl.

2-Substituted Ethyl Esters. Examples of 2-substituted ethyl esters include 2,2,2-trichloroethyl, 2-haloethyl, co-chloroalkyl, 2-(trimethylsilyl)ethyl, 2-methylthioethyl, 1,3-dithianyl-2-methyl, 2-(p-nitrophenylsulfenyl)ethyl, 2-(p-toluenesulfonyl)ethyl, 2-(2'-pyridyl)ethyl, 2-(diphenylphosphino)ethyl, 1-methyl-1-phenylethyl, t-butyl, cyclopentyl, cyclohexyl, allyl, 3-buten-1-yl, 4-(trimethylsilyl)-2-buten-1-yl, cinnamyl, α-methylcinnamyl, phenyl, p-(methylmercapto)phenyl and benzyl.

Substituted Benzyl Esters. Examples of substituted benzyl esters include triphenylmethyl, diphenylmethyl, bis(onitrophenyl)methyl, 9-anthrylmethyl, 2-(9,10-dioxo)anthrylmethyl, 5-dibenzosuberyl, 1-pyrenylmethyl, 2-(trifluoromethyl)-6-chromylmethyl, 2,4,6-trimethylbenzyl, Pbromobenzyl, o-nitrobenzyl, p-nitrobenzyl, p-methoxybenzyl, 2,6-dimethoxybenzyl, 4-(methylsulfinyl)benzyl, 4-sulfobenzyl, piperonyl, 4-picolyl and p-P-benzyl.

Silyl Esters. Examples of silyl esters include trimethylsilyl, triethylsilyl, t-butydimethylsilyl, i-propyidimethylsilyl, phenyldimethylsilyl and di-t-butylmethylsilyl.

Activated Esters. Examples of activated esters include thiols.

Miscellaneous Derivatives. Examples of miscellaneous derivatives include oxazoles, 2-alkyl-1,3-oxazolines, 4-alkyl-5-oxo-1,3-oxazolidines, 5-alkyl-4-oxo-1,3-dioxolanes, ortho esters, phenyl group and pentaaminocobalt(III) complex.

Stannyl Esters. Examples of stannyl esters include triethylstannyl and tri-n-butylstannyl.

Amides and Hydrazides

Amides. Examples of amides include N,N-dimethyl, pyrrolidinyl, piperidinyl, 5,6-dihydrophenanthridinyl, onitroanilides, N-7-nitroindolyl, N-8-Nitro-1,2,3,4-tetrahydroquinolyl, and p-P-benzenesulfonamides.

Hydrazides. Examples of hydrazides include N-phenyl and N,N'-diisopropyl.

Schemes

This disclosure includes the following Schemes:

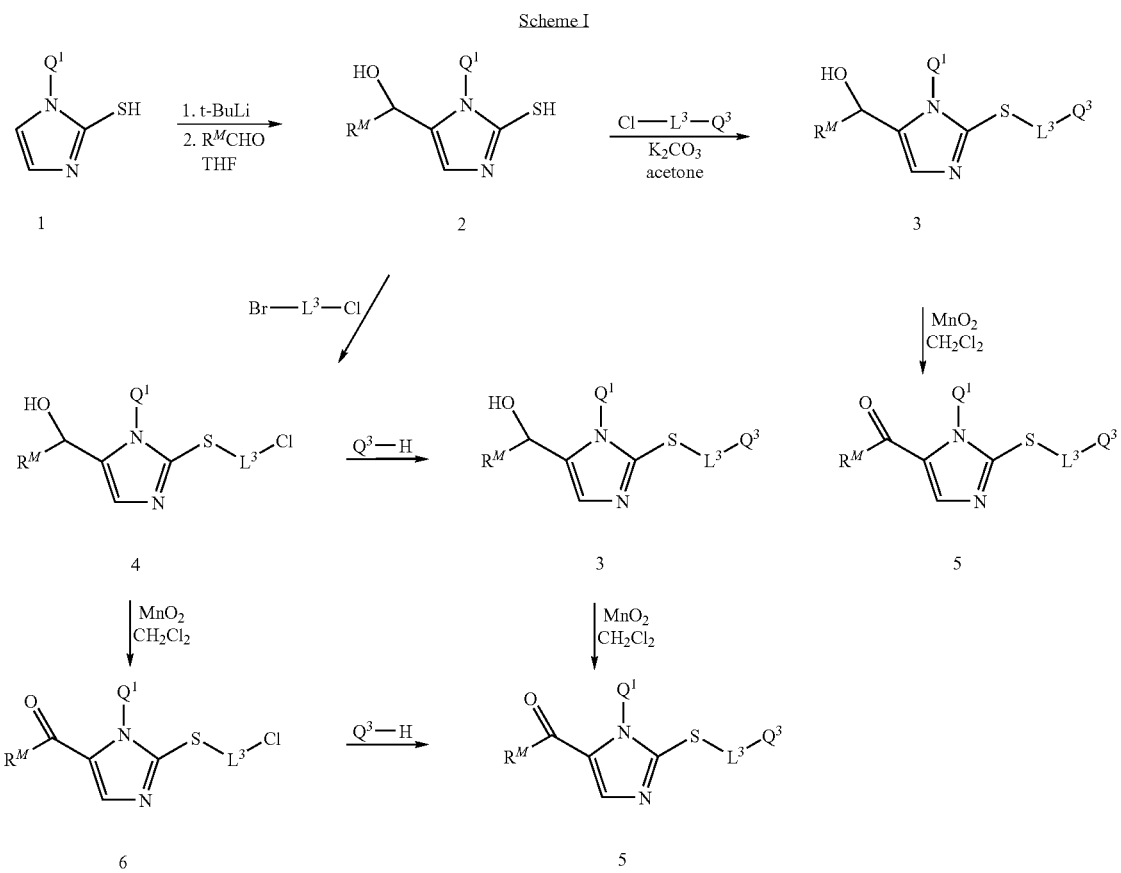

Scheme I

Following Scheme I above, compounds of formula (I) of the present invention where M is —C(=O)$R^M$, $A^3$ is sulfur, and $Q^1$, $R^M$, $L^3$ and $Q^3$ are optionally varied, are prepared.

In Scheme I, optionally substituted compound 1 is treated first with a base, preferably an organometallic base (e.g. n-BuLi, LTMP, LDA, LHMDS or, more preferably, t-BuLi), at a low-temperature gradient (preferably from −78° C. to 0° C.) in a solvent such as $Et_2O$, benzene, DME or, preferably, THF, and is then treated with aldehyde $R^M$CHO at low temperature (preferably −78° C.) to yield compound 2. Compound 2 is then treated with halide X-$L^3$-$Q^3$, where X is preferably chlorine, in the presence of a base (e.g. NaH, KOH or, preferably, $K_2CO_3$ in acetone) to provide compound 3. Compound 3 is treated with an oxidizing agent (e.g. $KMnO_4$, PCC, PDC, "Swern" oxidation reagents such as $(COCl)_2$/ $DMSO/Et_3N$, or, preferably, $MnO_2$ in $CH_2Cl_2$) to yield the desired compound 5 of the present invention. Alternatively, compound 2 may be treated with Br-$L^3$-Cl in the presence of a base (e.g. NaH, KOH or, preferably, $K_2CO_3$ in acetone) to provide compound 4. Compound 4 may be treated with an oxidizing agent, preferably $MnO_2$ in $CH_2Cl_2$, to yield compound 6, which is then treated with primary or secondary amine $Q^3$-H in the presence of a base (e.g. $K_2CO_3$/acetone) to yield the desired compound 5 of the present invention. Alternatively, compound 4 may be treated with primary or secondary amine $Q^3$-H in the presence of a base (e.g. $K_2CO_3$/acetone) to provide compound 3, which is then treated with an oxidizing agent, preferably $MnO_2$ in $CH_2Cl_2$, to again yield the desired compound 5 of the present invention.

Scheme II

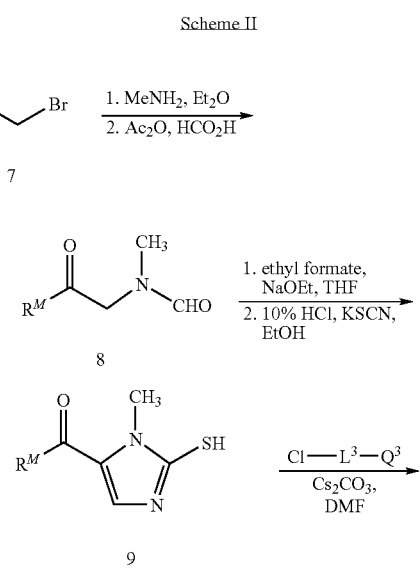

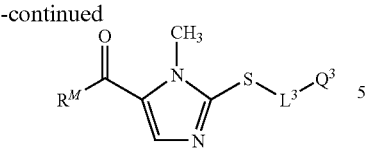

5a

Following Scheme II above, compounds of formula (I) of the present invention, where $Q^1$ is methyl, M is —C(═O)$R^M$, $A^3$ is sulfur, and $R^M$, $L^3$, and $Q^3$ are optionally varied, are prepared.

In Scheme II, alpha-bromoketone 7 is treated with methylamine in $Et_2O$, followed by a solution of formyl acetic anhydride (preformed from the reaction of acetic anhydride and formic acid) to afford compound 8. Compound 8 is treated with ethyl formate and an alkoxide (e.g. sodium methoxide, sodium tert-butoxide or, preferably, sodium ethoxide) in a solvent such as benzene or, preferably, THF, then cooled and treated with hydrochloric acid (10%) and potassium thiocyanate to give compound 9. (See R. G. Jones, *J. Am. Chem. Soc.* 1949, 71, 644.) Compound 9 is then treated with halide X-$L^3$-$Q^3$, where X is preferably chlorine, in the presence of a base (e.g. NaH, KOH or, preferably, $Cs_2CO_3$) to provide the desired compound 5a of the present invention.

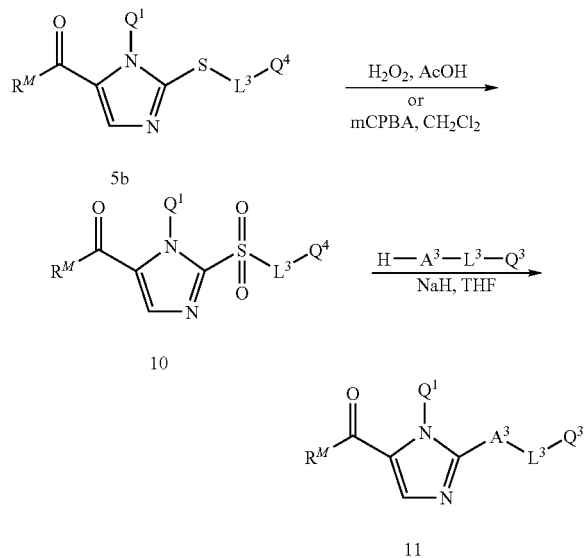

$Q^4$ = H
$A^3$ = NH, $NR^3$, O, S

Following Scheme III above, compounds of formula (I) of the present invention, where M is —C(═O)$R^M$, $A^3$ is NH, $NR^3$, oxygen or sulfur, and $Q^1$, $R^M$, $L^3$ and $Q^3$ are optionally varied are prepared. The starting material (5b) is prepared using Scheme I or Scheme XIV. The $L^3$ of the reagent H-$A^3$-$L^3$-$Q^3$ is independent of $L^3$ of formula 5b and formula 10 (both in Scheme III).

In Scheme III, compound 5b (in which $Q^4$ is hydrogen) is treated with an oxidizing agent, preferably hydrogen peroxide in acetic acid or 3-chloroperoxybenzoic acid in $CH_2Cl_2$ or $Et_2O$, to provide compound 10. Desired compound 11 of the present invention is obtained upon treatment of compound 10 with H-$A^3$-$L^3$-$Q^3$ in the presence of a base (e.g., KH or, preferably, NaH) in a solvent such as DMF, benzene, DME or, preferably, THF.

Scheme VII

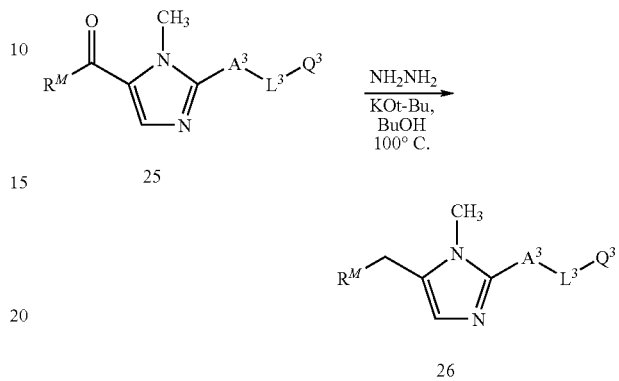

Following Scheme VII above, compounds of formula (I) of the present invention, where M is $CH_2R^M$, $Q^1$ is methyl, $A^3$ is sulfur or oxygen, and $R^M$, $L^3$ and $Q^3$ are optionally varied, are prepared. The starting material (25) can be prepared using Schemes I, III, IX, X, or XIV.

Desired compound 26 of the present invention is obtained upon reduction of compound 25 under "Wolff-Kishner" conditions, that is, treatment with hydrazine in the presence of a base (e.g. KOH, NaOH or, preferably, KOt-Bu) in a solvent such as ethylene glycol or, preferably, butanol at elevated temperature (e.g. 100° C.).

Scheme VIII

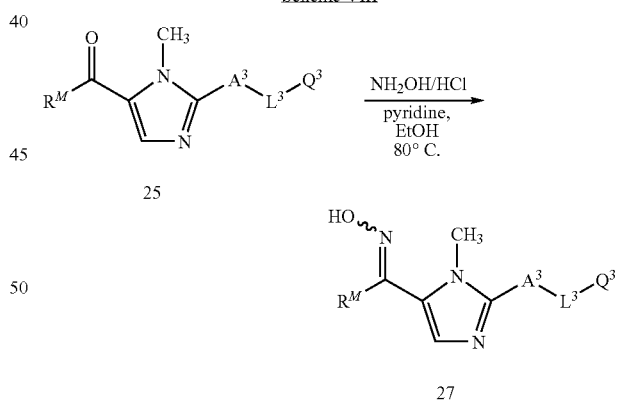

Following Scheme VIII above, compounds of formula (I) of the present invention, where M is —C(═N—OH)$R^M$, $Q^1$ is methyl, $A^3$ is sulfur or oxygen, and $L^3$, $Q^3$ and $R^M$ are optionally varied, are prepared. The starting material (25) can be prepared using Schemes I, III, IX, X, or XIV.

Compound 25 is treated with hydroxylamine hydrochloride in the presence of NaOAc or, preferably, pyridine in an alcoholic solvent (e.g. methanol or, preferably, ethanol) at elevated temperature (e.g. 80° C.) to afford the desired oxime compound 27 of the present invention.

Scheme IX

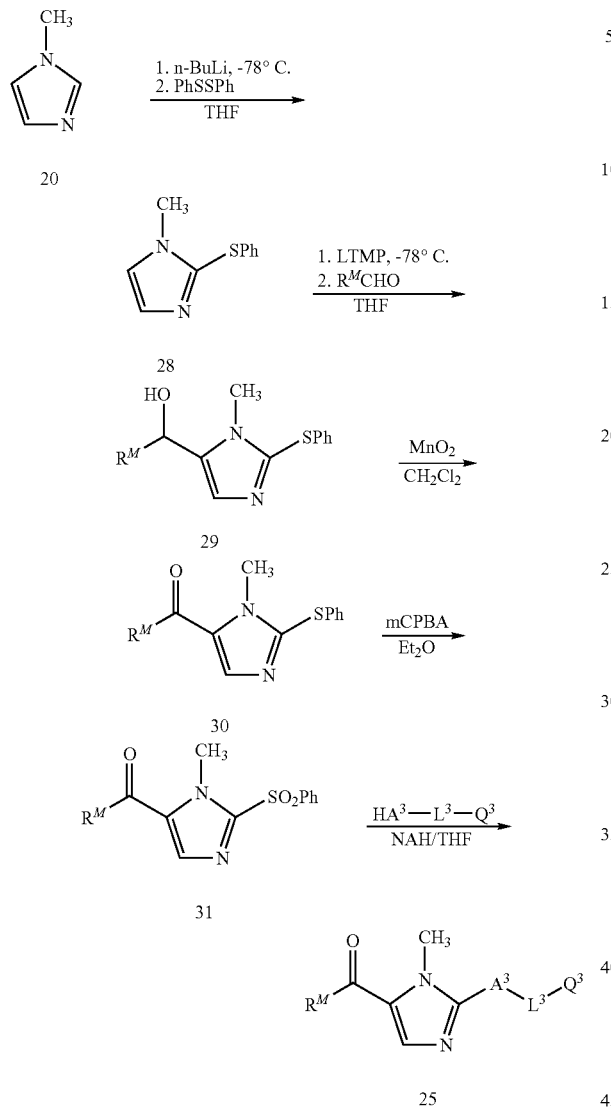

Scheme X

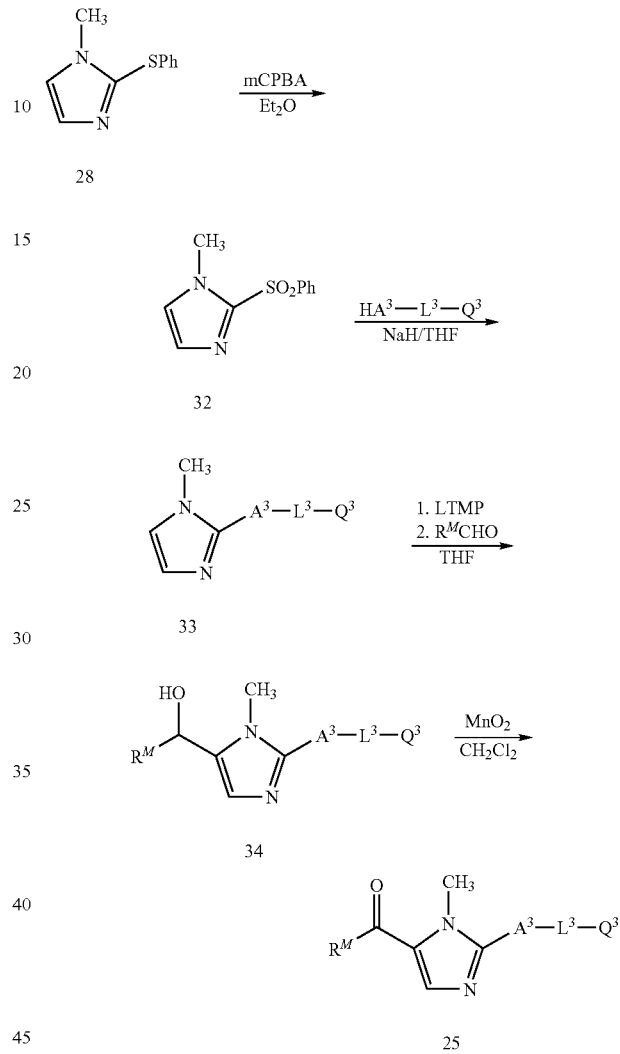

Following Scheme IX above, compounds of formula (I) of the present invention, where M is —C(=O)$R^M$, $Q^1$ is methyl, and $A^3$, $L^3$, $Q^3$ and $R^M$ are optionally varied, are prepared.

Compound 20 is treated with an organolithium base (e.g. LDA, t-BuLi or, preferably, n-BuLi) at low temperature (preferably –78° C.) in a solvent such as DME, $Et_2O$ or, preferably, THF, followed by treatment with an organo-disulfide, preferably diphenyldisulfide, to afford compound 28. Compound 29 is obtained by treating compound 28 with a base (e.g. LHMDS, LDA or, preferably, LTMP) at low temperature (preferably –78° C.) in a solvent such as THF, followed by aldehyde RMCHO. Compound 29 is treated with an oxidizing agent (e.g. $KMnO_4$, PCC, PDC, "Swern" oxidation reagents such as $(COCl)_2$/DMSO/$Et_3N$ or, preferably, $MnO_2$ in $CH_2Cl_2$) to yield compound 30, which is treated with an oxidizing agent (e.g.hydrogen peroxide in acetic acid, 3-chloroperoxybenzoic acid in $CH_2Cl_2$, or, preferably, 3-chloroperoxybenzoic acid in $Et_2O$) to provide compound 31. Desired compound 25 of the present invention is obtained upon treatment of compound 31 with H-$A^3$-$L^3$-$Q^3$ in the presence of a base (e.g. KH or, preferably, NaH) in a solvent such as DMF, benzene, DME or, preferably, THF.

Following Scheme X above, compounds of formula (I) of the present invention, where M is —C(=O)$R^M$, $Q^1$ is methyl, and $A^3$, $L^3$, $Q^3$, and $R^M$ are optionally varied, are prepared. The starting material is compound 28 from Scheme IX.

Compound 28 is treated with an oxidizing agent (e.g. hydrogen peroxide in acetic acid or, preferably, 3-chloroperoxybenzoic acid in $Et_2O$) to provide compound 32. Compound 33 is obtained upon treatment of compound 32 with H-$A^3$-$L^3$-$Q^3$ in the presence of a base (e.g. KH or, preferably, NaH) in a solvent such as DMF, benzene, DME or, preferably, THF. Compound 34 is obtained by treating compound 33 with a base (e.g. LHMDS, LDA or, preferably, LTMP) at low temperature (preferably –78° C.) in a solvent such as THF, followed by aldehyde RMCHO. Compound 34 is treated with an oxidizing agent (e.g. $KMnO_4$, PCC, PDC, "Swern" oxidation reagents such as $(COCl)_2$/DMSO/$Et_3N$ or, preferably, $MnO_2$ in $CH_2Cl_2$) to yield the desired compound 25 of the present invention.

Scheme XI

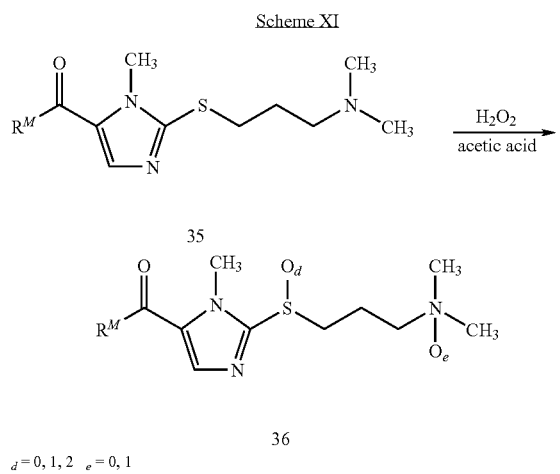

d = 0, 1, 2  e = 0, 1

Following Scheme XI above, compounds of formula (I) of the present invention, where M is —C(=O)R$^M$, Q$^1$ is methyl, A$^3$ is sulfur, sulfoxide or sulfone, L$^3$ is n-propyl, Q$^3$ is dimethylamino or dimethylazinoyl and R$^M$ is optionally varied, are prepared. In general, the starting material (35), is prepared using Scheme X to provide appropriately substituted 25 (i.e. compound 35). Where R$^M$ is hydrogen, compound 35 is obtained directly from 33 in Scheme X by treatment of the latter with 1) LTMP and 2) DMF. Starting materials may also be prepared using Schemes I, III, or XIV.

Compound 35 is treated with hydrogen peroxide in acetic acid to provide desired compounds 36 of the present invention as a mixture of desired oxidation states. The product mixture is separated by chromatography (e.g. flash chromatography on silica gel).

Scheme XII

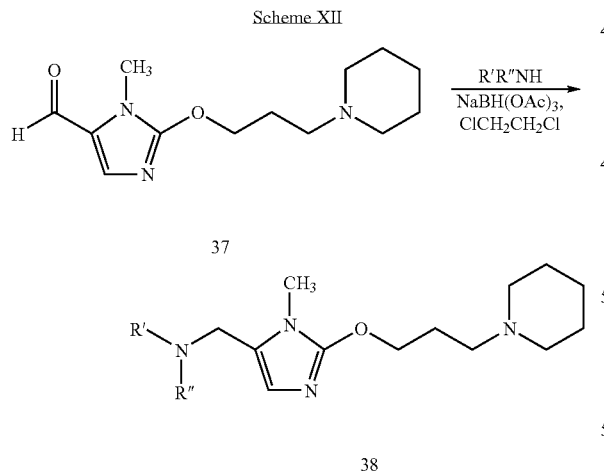

Following Scheme XII above, compounds of formula (I) of the present invention, where M is CH$_2$R$^M$, R$^M$ is optionally substituted —NR'R" (where R' and R" are independently C$_{1-7}$ alkyl or, taken together with the nitrogen to which they are attached, form a four- to seven-membered nitrogen heterocycle), Q$^1$ is methyl, A$^3$ is oxygen, L$^3$ is n-propyl and Q$^3$ is N-piperidyl, are prepared. The starting material, compound 37, is prepared using Scheme X to provide appropriately substituted 33 (i.e. A$^3$ is oxygen, L$^3$ is n-propyl and Q$^3$ is N-piperidyl). Compound 37 is then obtained directly from 33 in Scheme X by treatment of the latter with 1) LTMP and 2) DMF.

Desired compound 38 of the present invention is obtained by treating compound 37 with an amine in the presence of a reducing agent such as NaBH$_3$CN or, preferably, NaBH(OAc)$_3$ in a solvent such as methanol, ethanol, CF$_3$CH$_2$OH or, preferably, 1,2-dichloroethane.

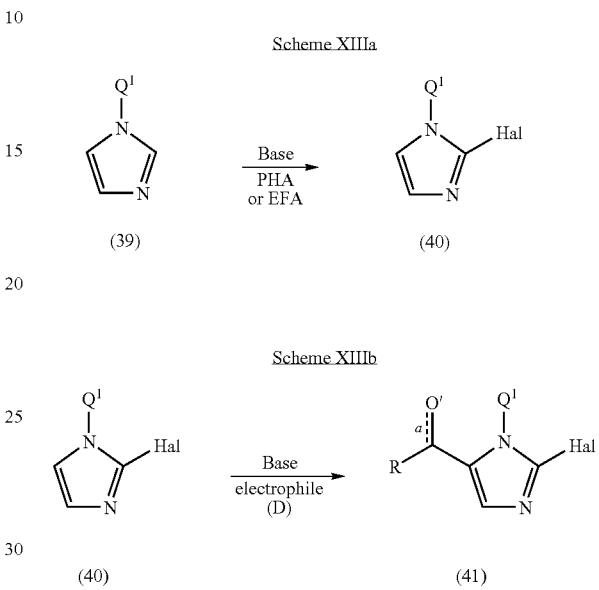

Features and characteristics of Scheme I.1 and entitites (A) and (B) therein comprise at least the features and characteristics of Scheme XIIIa and entities (39) and (40) described herein. Following Scheme XIIIa above, imidazole 39 is treated with a suitable base, preferably an organolithium compound. Embodiments of this invention use any of the following bases and chemically compatible mixtures thereof: LDA, LiHMDS (or LHMDS), t-BuLi, sec-BuLi, n-BuLi. A preferred base is n-BuLi. The treatment with a base is performed at a temperature such that the desired organolithium species is formed and is stable at such temperature. Embodiments of this invention include performing this treatment with a base at a temperature in the range from about 0° C. to about –100° C. The temperature range is from about –20° C. to about –90° C. in other embodiments. A preferred temperature for such treatment is about –78° C. The treatment with a base is performed in a solvent such that it is not detrimental to the stability of the organolithium species being formed. Examples of solvents that are used in embodiments of this invention are DME, Et$_2$O, THF, and chemically compatible mixtures thereof. A preferred solvent is THF. Preparation of imidazole derivative (39) from generally available products is within the ordinary skill in the art.

Reaction of the resulting organolithium species with PHA, an N—F electrophilic fluorinating agent (EFA), or a chemically compatible mixture thereof, yields 2-haloimidazole 40, wherein Hal is fluoro or chloro. Such reaction in some embodiments of this invention is performed with a perchloroalkane to produce 2-chloroimidazole. A perchloroC$_{2-6}$alkane is used in some embodiments of this invention. A preferred PHA is hexachloroethane. The PHA is preferably added in a solvent that is chemically compatible with the solvent that is used in the base treatment. Some embodiments of this invention use the same solvent for the base treatment and for the introduction of PHA. Some embodiments of this invention use introduction of PHA without solvent as an undiluted solid. Other embodiments of this invention use a PHA that falls within the definition of this term given herein.

In the case of a chloro substitution, a perchloro$C_{2-6}$alkane is used as an electrophile. For fluoro substitution, an N—F electrophilic fluorinating agent (EFA) may be used. Examples of EFAs are: 1-chloromethyl-4-fluoro-1,4-diazoniabicyclo[2.2.2]octane bis-(tetrafluoroborate), also known as Selectfluor®; N-fluorobenzenesulfonamide, also known as NSFI; N-fluoropyridinium triflate; N-fluoroquiniclidinium triflate. For more examples of electrophilic fluorinating agents, see Taylor, S. D.; Kotoris, C. C.; Hum, G., *Tetrahedron* 1999, 55, 12431-12477.

Features and characteristics of Scheme 1.2 and entities (B), (C), and (D) therein comprise at lest the features and characteristics if Scheme XIIIb and entities (40), (41) and D described herein. As indicated in Scheme XIIIb, compound 40 is then treated with a suitable base, such as an organolithium compound. Examples of such base are LDA, LiHMDS, t-BuLi, sec-BuLi, n-BuLi, and chemically compatible mixtures thereof. A preferred base is n-BuLi. The choice of base in Scheme XIIIa is in some embodiments of this invention the same as the choice of base in Scheme XIIIb. In other embodiments, the choice of base in Scheme XIIIa is different from that in Scheme XIIIb. Embodiments of this invention include performing this treatment with a base at a temperature in the range from about 0° C. to about −100° C., The temperature range is from about −20° C. to about −90° C. in other embodiments. A preferred temperature for such treatment is about −78° C., The treatment with a base is performed in a solvent such that the organolithium species generated during the reaction is stable. Examples of solvents that are used in embodiments of this invention are DME, Et$_2$O, THF, and chemically compatible mixtures thereof. A preferred solvent is THF.

Treatment with a suitable electrophile (D) affords compound 41. Suitable electrophiles (D) include those wherein:

electrophile (D) is O═C(X)R, a is a single bond, X is H, O' is OH, and R is $R^M$;

electrophile (D) is O═C(X)R, a is a double bond, X is —N(OMe)Me, O' is O, and R is $R^M$;

electrophile (D) is CO$_2$, a is a double bond, and O' is O; R is hydroxy; or electrophile (D) is O═C(X)R, a is a double bond, X is fluoro, chloro, bromo or iodo, O' is O, R is $R^M$.

In the foregoing electrophile (D) descriptions, $R^M$ is defined as indicated herein.

Some embodiments of this invention block the C-2 position with a blocking group during metallation of the C-5 position to regioselectively introduce a substituent in such C-5 position. Furthermore, some embodiments of this invention use as such blocking group a group that can be an effective reactive leaving group in a nucleophilic substitution that introduces a substituent in the C-2 position. It was furthermore found in the context of this invention that such blocking group can be embodied by a group that does not undergo halogen-metal exchange to a significant extent (exchange being less than about 5%) under the conditions taught herein. These conditions include the metallation of the C-5 position to regioselectively introduce a desired substituent in such C-5 position. This characteristic of such group is herein referred to as being stable to metal exchange conditions.

Scheme XIV

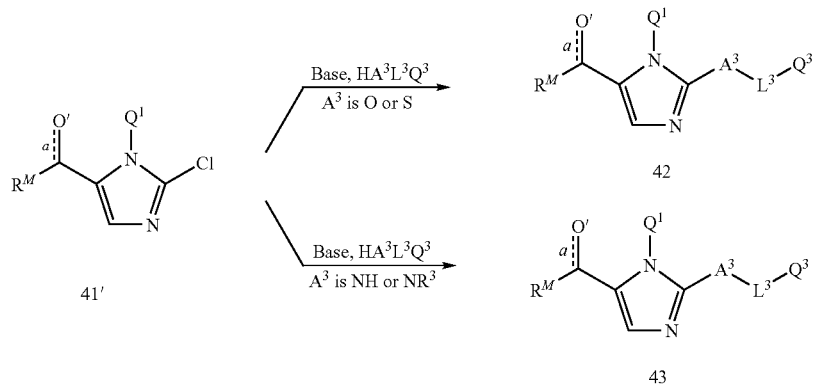

Following Scheme XIV above, compound 41' (where O' is ═O, and a is a double bond) can be converted into compounds of formula (I) where M is —C(═O)$R^M$ and $A^3$ is O or S. An appropriate oxygen or sulfur nucleophile is deprotonated with a suitable base, preferably NaH or n-BuLi, in a solvent such as THF at reduced temperature (preferably 0° C. for NaH and −78° C. for n-BuLi), and treated with compound 41' at elevated temperature, preferably 60° C., to provide compound 42. Alternatively, compound 41' can be transformed into compounds of formula (I) where $A^3$ is NH or NR$^3$. In this instance, compound 41' can be treated with a nucleophilic primary or secondary amine and a suitable base, preferably a trialkylamine base such as diisopropylethylamine, in a solvent such as THF, at elevated temperature (preferably 60° C.) to provide analogs 43.

Scheme XIVa

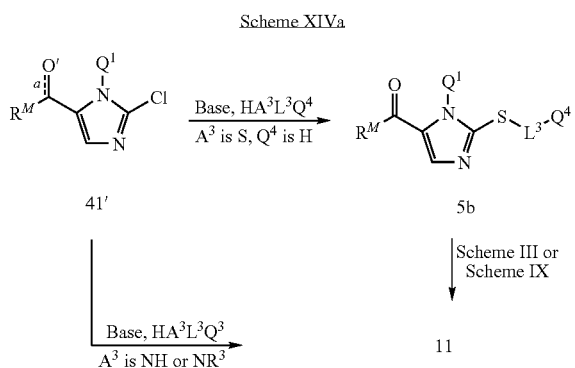

Following Scheme XIVa above, compound 41' (where a is a double bond) is reacted with $HA^3L^3Q^4$ (where $A^3$ is S and $Q^4$ is H) in the presence of base to give thioether 5b. Compound 5b may be converted to compound 11 according to methods described in Schemes III and IX, by first an oxidation step to provide a compound of formula 10, and then by a displacement step in the presence of base. Alternatively, compound 41' (where a is a double bond) is reacted with $HA^3L^3Q^3$ (where $A^3$ is S, O, NH, or $NR^3$) in the presence of base to give compound 11 directly as described for Scheme XIV.

priate oxygen or sulfur nucleophile is deprotonated with a suitable base, preferably NaH or n-BuLi, in a solvent such as THF at reduced temperature (preferably 0° C. for NaH and −78° C. for n-BuLi), and treated with compound 44 at elevated temperature, preferably 60° C., to provide compound 45. The protecting group can be removed during the workup of this step, or in a separate step using standard conditions, to form compound 46.

Alternatively, compound 41' can be transformed into compounds of formula (I) where M is —$CHOHR^M$ and $A^3$ is NH or $NR^3$. In this instance, compound 41' can be treated, with or without protection of the hydroxyl group, with a nucleophilic primary or secondary amine and a suitable base, preferably a trialkylamine base such as diisopropylethylamine, in a solvent such as THF, at elevated temperature (preferably 60° C.) to provide analogs 46.

The products derived from Schemes XIII, XIV, and XV can subsequently be transformed into other preferred embodiments as described in previous Schemes, including: a) compounds of formula (I) where $A^3$ is sulfoxide or sulfone as shown in Scheme XI; b) compounds of formula (I) where M is —$CH_2R^M$ as shown in Scheme VII and Scheme XII; and c) compounds of formula (I) where M is —C(=N—OH)$R^M$ as shown in Scheme VIII.

In compounds where substituents $R^M$, $L^3$, and $Q^3$ are incompatible with the described reaction conditions, suitable protecting groups are employed. If a particular group is not

Scheme XV

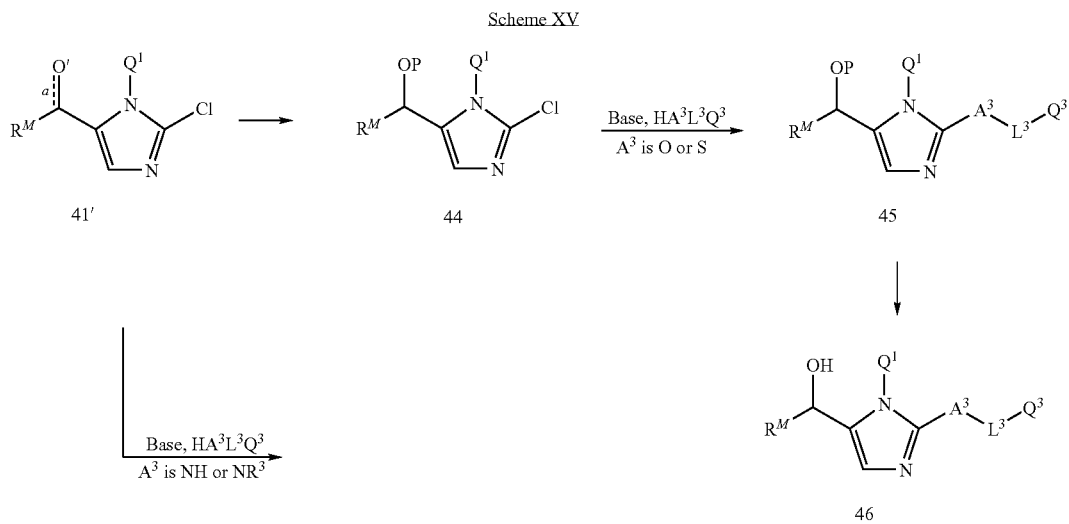

Following Scheme XV above, compound 41' (where O' is —OH, and a is a single bond) can be converted into compounds of formula (I) where M is —$CHOHR^M$ and $A^3$ is O or S. The free hydroxyl group in compound 41' can be protected (represented by "OP" of compound 44 in Scheme XV) with a suitable protecting group, such as a tetrahydropyranyl or t-butyldimethylsilyl group, using conventional methods known to one skilled in the art, to form compound 44. As will be perceived by one of ordinary skill in the art, this protection, and the optional subsequent deprotection, also applies(y) to other OH groups, if present, in addition to the one in the O' position, in need of such protection. These protection/deprotection steps applied to whichever OH group(s) is(are) in need thereof, are herein referred to collectively as "hydroxy protection" and "hydroxy deprotection", respectively. An approamenable to protection, it may be introduced using synthetic steps performed after the ones shown in Scheme XIII, XIV, and XV. Appropriate synthetic steps for the introduction of such groups that are not described explicitly herein are known to one of ordinary skill in the art.

Where the processes for the preparation of the compounds according to the invention give rise to mixtures of stereoisomers, these isomers may be separated by conventional techniques such as resolution, for example by formation of diastereomeric salts, kinetic resolution including variants thereof, such as dynamic resolution, preferential crystallization, biotransformation, enzymatic transformation, and preparative chromatography. The compounds may be prepared in racemic form, or individual enantiomers may be prepared either by enantiospecific synthesis or by resolution. The compounds may, for example, be resolved into their component enantiomers by standard techniques, such as the formation of diastereomeric pairs by salt formation with an optically active acid, such as (−)-di-p-toluoyl-D-tartaric acid and/or (+)-di-p-toluoyl-L-tartaric acid followed by fractional crystallization and regeneration of the free base. The compounds may also be resolved by formation of diastereomeric esters or amides, followed by chromatographic separation and removal of the chiral auxiliary. Alternatively, the compounds may be separated using a chiral HPLC column. Regioisomeric mixtures may also be separated into their constituent regioisomers by conventional techniques.

For therapeutic use, salts of the compounds of the present invention are those that are pharmaceutically acceptable. However, salts of acids and bases that are non-pharmaceutically acceptable may also find use, for example, in the preparation or purification of a pharmaceutically acceptable compound. All salts, whether pharmaceutically acceptable or not are included within the ambit of the present invention.

Pharmaceutically acceptable salts, esters, and amides of compounds according to the present invention refer to those salts, amides and ester forms of the compounds of the present invention that would be apparent to the pharmaceutical chemist, i.e., those that are non-toxic and that would favorably affect the pharmacological properties of said compounds of the present invention. Those compounds having favorable pharmacological properties would be apparent to the pharmaceutical chemist, i.e., those that are non-toxic and that possess such pharmacological properties to provide sufficient palatability, absorption, distribution, metabolism and excretion. Other factors, more practical in nature, that are also important in the selection are cost of raw materials, ease of crystallization, yield, stability, hygroscopicity, and flowability of the resulting bulk drug.

Examples of acids that may be used in the preparation of pharmaceutically acceptable salts include the following: acetic acid, 2,2-dichloroacetic acid, acylated amino acids, adipic acid, alginic acid, ascorbic acid, L-aspartic acid, benzenesulfonic acid, benzoic acid, 4-acetamidobenzoic acid, (+)-camphoric acid, camphorsulfonic acid, (+)-(1S)-camphor-10-sulfonic acid, capric acid, caproic acid, caprylic acid, cinnamic acid, citric acid, cyclamic acid, cyclohexanesulfamic acid, dodecylsulfuric acid, ethane-1,2-disulfonic acid, ethanesulfonic acid, 2-hydroxy-ethanesulfonic acid, formic acid, fumaric acid, galactaric acid, gentisic acid, glucoheptonic acid, D-gluconic acid, D-glucuronic acid, L-glutamic acid, x-oxo-glutaric acid, glycolic acid, hippuric acid, hydrobromic acid, hydrochloric acid, hydroiodic acid, (+)-L-lactic acid, (±)-DL-lactic acid, lactobionic acid, maleic acid, (−)-L-malic acid, malonic acid, (±)-DL-mandelic acid, methanesulfonic acid, naphthalene-2-sulfonic acid, naphthalene-1,5-disulfonic acid, 1-hydroxy-2-naphthoic acid, nicotinic acid, nitric acid, oleic acid, orotic acid, oxalic acid, palmitic acid, pamoic acid, perchloric acid, phosphoric acid, L-pyroglutamic acid, saccharic acid, salicylic acid, 4-aminosalicylic acid, sebacic acid, stearic acid, succinic acid, sulfuric acid, tannic acid, (+)-L-tartaric acid, thiocyanic acid, ptoluenesulfonic acid and undecylenic acid.

Compounds of the present invention containing acidic protons may be converted into their therapeutically active non-toxic metal or amine addition salt forms by treatment with appropriate organic and inorganic bases. Appropriate base salt forms comprise, for example, the ammonium salts; the alkali and earth alkaline metal salts (e.g. lithium, sodium, potassium, magnesium, calcium salts, which may be prepared by treatment with, for example, magnesium hydroxide, calcium hydroxide, potassium hydroxide, zinc hydroxide, or sodium hydroxide); and amine salts made with organic bases (e.g. primary, secondary and tertiary aliphatic and aromatic amines such as L-arginine, benethamine, benzathine, choline, deanol, diethanolamine, diethylamine, dimethylamine, dipropylamine, diisopropylamine, 2-(diethylamino)-ethanol, ethanolamine, ethylamine, ethylenediamine, isopropylamine, N-methyl-glucamine, hydrabamine, 1H-imidazole, L-lysine, morpholine, 4-(2-hydroxyethyl)-morpholine, methylamine, piperidine, piperazine, propylamine, pyrrolidine, 1-(2-hydroxyethyl)-pyrrolidine, pyridine, quinuclidine, quinoline, isoquinoline, secondary amines, triethanolamine, trimethylamine, triethylamine, N-methyl-D-glucamine, 2-amino-2-(hydroxymethyl)-1,3-propanediol, and tromethamine). See, e.g., S. M. Berge, etal., "Pharmaceutical Salts", J. Pharm. Sci., 1977, 66:1-19, which is incorporated herein by reference.

"Salt" also comprises the hydrates and solvent addition forms that compounds of the present invention are able to form. Examples of such forms are hydrates, alcoholates, and generally solvates.

Examples of suitable esters include $C_{1-7}$alkyl, $C_{5-7}$cycloalkyl, phenyl, substituted phenyl, and phenyl$C_{1-6}$alkyl-esters. Preferred esters include methyl esters. Furthermore, examples of suitable esters include such esters where one or more carboxyl substituents is replaced with p-methoxybenzyloxy-carbonyl, 2,4,6-trimethylbenzyloxycarbonyl, 9-anthryloxycarbonyl, $CH_3SCH_2COO$—, tetrahydrofur-2-yloxycarbonyl, tetrahydropyran-2-yloxy-carbonyl, fur-2-yloxycarbonyl, benzoylmethoxycarbonyl, p-nitrobenzyloxycarbonyl, 4-pyridylmethoxycarbonyl, 2,2,2-trichloroethoxycarbonyl, 2,2,2-tribromoethoxycarbonyl, t-butyloxycarbonyl, t-amyloxycarbonyl, diphenylmethoxycarbonyl, triphenylmethoxycarbonyl, adamantyloxycarbonyl, 2-benzyloxyphenyloxycarbonyl, 4-methylthiophenyloxycarbonyl, or tetrahydropyran-2-yloxycarbonyl.

Whether referred to herein explicitly or not, each of the terms "pharmaceutically acceptable salts," "pharmaceutically acceptable esters," and "pharmaceutically acceptable amides" include those salts, esters and amides, respectively that do not change the intrinsic properties of the active ingredient. See, for example, Remington, The Science and Practice of Pharmacy, 704 ($20^{th}$ ed., 2000).

"Patient" or "subject" includes mammals such as human beings and animals (e.g., dogs, cats, horses, rats, rabbits, mice, non-human primates) in need of observation, experiment, treatment or prevention in connection with the relevant disease or condition. Preferably, the patient is a human being.

As used herein, the term "composition" is intended to encompass a product comprising the specified ingredients in the specified amounts, as well as any product that results, directly or indirectly, from combinations of the specified ingredients in the specified amounts.

The term "therapeutically effective amount" as used herein, means that amount of active compound or pharmaceutical agent, alone or in combination with another agent according to the particular aspect of the invention, that elicits the biological or medicinal response in a tissue system, animal or human that is being sought by a researcher, veterinarian, medical doctor or other clinician, where the medical response includes, but is not limited to, alleviation of the symptoms of the disease or disorder being treated. For example, a method of treatment relating to a disclosed compound and another compound specified in the claim can include (a) an independently therapeutically effective amount of the disclosed compound and an independently therapeutically effective amount of the specified compound; (b) an independently sub-therapeutically effective amount of a disclosed compound and an independently sub-therapeutically effective amount of the specified compound; or (c) an independently therapeutically effective amount of one compound and an independently sub-therapeutically effective amount of the other compound. The invention features any of the above combinations such that the co-administration steps, the co-administration amounts, or both the steps and the amounts together provide the desired pharmaceutical effect. Advantages of such co-administration can include improvement in the side-effect profiles of one or more of the co-administered agents.

The compounds according to this invention are modulators of the histamine $H_3$ receptor, and as such, the compounds are useful in the treatment of histamine $H_3$-mediated disease states. The present invention provides for pharmaceutical compositions for the treatment of disorders and conditions modulated by a histamine receptor, more particularly the $H_3$ receptor, comprising a pharmaceutically acceptable carrier and one or more compounds according to this invention. The invention also provides a process for making a pharmaceutical composition comprising formulating a pharmaceutically acceptable carrier and one or more of the compounds according to this invention. The present invention also provides pharmaceutical compositions (and methods of making same) comprising one or more compounds of this invention in association with a pharmaceutically acceptable carrier and one or more additional pharmaceutical agents such as $H_1$ receptor antagonists, $H_2$ receptor antagonists, SSRIs (such as PROZAC™), selective norepinephrine uptake inhibitors, or modafinil.

The present invention also provides for methods for treating various disorders associated with histamine activity, more particularly histamine $H_3$ antagonist activity, comprising administering to a subject in need of such treatment a therapeutically effective amount of one or more compounds according to this invention. The present invention also provides for methods for treating various disorders associated with histamine activity, more particularly, histamine $H_3$ antagonist activity, comprising administering to a subject in need of such treatment a therapeutically effective amount of a pharmaceutical composition according to this invention. The present invention also provides methods for the treatment of disorders and conditions modulated by a histamine receptor, more particularly the $H_3$ receptor, comprising administering to a subject in need of such treatment a therapeutically effective amount of one or more compounds of this invention in combination with one or more additional pharmaceutical agents such as $H_1$ receptor antagonists, $H_2$ receptor antagonists, SSRIs (such as PROZAC™), selective norepinephrine uptake inhibitors, or modafinil. Also included in the present invention are methods of co-administration, comprising administering at least one disclosed compound and administering at least one agent selected from a histamine $H_1$ receptor modulating compound, a histamine $H_2$ receptor modulating compound, an SSRI (such as PROZAC™), a selective norepinephrine uptake inhibiting compound, and modafinil; and combination compositions thereof. Co-administration includes essentially simultaneous administration of either a co-formulated combination or separate formulations, and administration of separate formulations at different times.

Compounds of this invention, alone or in combination (with, for example, a histamine $H_1$ receptor antagonist), are useful in pharmaceutical compositions and in methods for treating or preventing histamine $H_3$ receptor mediated disorders such as neurologic disorders including sleep/wake and arousal/vigilance disorders (e.g. insomnia and jet lag), attention deficit hyperactivity disorders (ADHD), learning and memory disorders, cognitive dysfunction, migraine, neurogenic inflammation, dementia, mild cognitive impairment (pre-dementia), Alzheimer's disease, epilepsy, narcolepsy with or without associated cataplexy, cataplexy, disorders of sleep/wake homeostasis, idiopathic somnolence, excessive daytime sleepiness (EDS), circadian rhythm disorders, sleep/fatigue disorders, fatigue, drowsiness associated with sleep apnea, sleep impairment due to perimenopausal hormonal shifts, Parkinson's-related fatigue, MS-related fatigue, depression-related fatigue, chemotherapy-induced fatigue, eating disorders, obesity, motion sickness, vertigo, schizophrenia, substance abuse, bipolar disorders, manic disorders and depression, as well as other histamine $H_3$ receptor mediated disorders such as upper airway allergic response, asthma, itch, nasal congestion and allergic rhinitis in a subject in need thereof. Excessive daytime sleepiness (EDS) may occur with or without associated sleep apnea, shift work, fibromyalgia, MS, and the like.

The present invention provides a series of heterocyclic derivatives with the ability to modulate the activity of a histamine receptor, specifically the $H_3$ receptor. These heterocycles include N(1)-substituted imidazoles that contain both 2- and 5-substituents.

A number of compounds of the present invention that are methylated at the N(1) position of the imidazole ring have been found to have exceptional activity.

The present invention provides a method of treating disorders and conditions mediated by the $H_3$ receptor, particularly a method of treating attention deficit hyperactivity disorder (ADHD) (i.e., improving attention and/or memory retention), in a subject in need thereof that comprises administering one or more of the compounds according to this invention in a therapeutically effective amount. The compound may be administered to a subject by any conventional route of administration, including, but not limited to, intravenous, oral, subcutaneous, intramuscular, intradermal and parenteral. The quantity of the compound that is effective for treating ADHD is between 0.01 mg per kg and 20 mg per kg of subject body weight.

The present invention provides a method for treating dementia and/or Alzheimer's disease, wherein a compound according to this invention acts as a histamine $H_3$ antagonist (Panula, et al. 1995).

The present invention provides a method for treating epilepsy according to (Yokoyama, et al. 1993), wherein a compound of the present invention acts as a histamine $H_3$ antagonist.

The present invention provides a method for treating narcolepsy and/or eating disorders based on the reference, Machidori, et al. 1992, where a compound of the present invention acts as a histamine $H_3$ antagonist.

The present invention provides a method for treating one or more disorders or conditions selected from a group consisting of motion sickness, vertigo, attention deficit hyperactivity disorders (ADHD), and learning and memory disorders, wherein a compound of the present invention acts as a histamine $H_3$ antagonist, based on the reference, Barnes, et al. 1993.

The present invention provides a method for treating schizophrenia based on the reference, Schlicker, et al. 1996, wherein a compound of the present invention acts as a histamine $H_3$ antagonist.

The present invention provides a method of treating upper airway allergic response by administering a compound of the present invention alone, or in combination with a histamine $H_1$ antagonist. Such utility is reported in U.S. Pat. Nos. 5,217,986; 5,352,707; and 5,869,479.

The pharmaceutical compositions can be prepared using conventional pharmaceutical excipients and compounding techniques. Preferably these compositions are in unit dosage forms such as tablets, pills, capsules, powders, granules, sterile parenteral solutions or suspensions, metered aerosol or liquid sprays, drops, ampoules, autoinjector devices or suppositories; for oral, parenteral, intranasal, sublingual or rectal administration, or for administration by inhalation or insufflation. Alternatively, the composition may be presented in a form suitable for once-weekly or once-monthly administration; for example, an insoluble salt of the active compound, such as the decanoate salt, may be adapted to provide a depot preparation for intramuscular injection. For preparing solid compositions such as tablets, the principal active ingredient is mixed with a pharmaceutical carrier, e.g. conventional tableting ingredients such as corn starch, lactose, sucrose, sorbitol, talc, stearic acid, magnesium stearate, dicalcium phosphate or gums, and other pharmaceutical diluents, e.g. water, to form a solid preformulation composition containing a homogeneous mixture of a compound of the present invention, or a pharmaceutically acceptable salt thereof. When referring to these preformulation compositions as homogeneous, it is meant that the active ingredient is dispersed evenly throughout the composition so that the composition may be readily subdivided into equally effective dosage forms such as tablets, pills and capsules. This solid preformulation composition is then subdivided into unit dosage forms of the type described above containing from 1 to about 1000 mg of the active ingredient of the present invention. The tablets or pills of the novel composition can be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer, which serves to resist disintegration in the stomach and permits the inner component to pass intact into the duodenum or to be delayed in release. A variety of materials can be used for such enteric layers or coatings, such materials including a number of polymeric acids with such materials as shellac, cetyl alcohol and cellulose acetate.

The liquid forms in which the novel compositions of the present invention may be incorporated for administration orally or by injection include, aqueous solutions, suitably flavoured syrups, aqueous or oil suspensions, and flavoured emulsions with edible oils such as cottonseed oil, sesame oil, coconut oil or peanut oil, as well as elixirs and similar pharmaceutical vehicles. Suitable dispersing or suspending agents for aqueous suspensions, include synthetic and natural gums such as tragacanth, acacia, alginate, dextran, sodium carboxymethylcellulose, methylcellulose, polyvinyl-pyrrolidone or gelatin. For parenteral administration, sterile suspensions and solutions are desired. Isotonic preparations that generally contain suitable preservatives are employed when intravenous administration is desired.

Advantageously, compounds of the present invention may be administered in a single daily dose, or the total daily dosage may be administered in divided doses of two, three or four times daily. Furthermore, compounds for the present invention can be administered in intranasal form via topical use of suitable intranasal vehicles, or via transdermal skin patches well known to those of ordinary skill in that art. To be administered in the form of a transdermal delivery system, the dosage administration will, of course, be continuous rather than intermittent throughout the dosage regimen.

For instance, for oral administration in the form of a tablet or capsule, the active drug component can be combined with an oral, non-toxic pharmaceutically acceptable inert carrier such as ethanol, glycerol, water, and the like. Moreover, when desired or necessary, suitable binders, lubricants, disintegrating agents and coloring agents can also be incorporated into the mixture. Suitable binders include, without limitation, starch, gelatin, natural sugars such as glucose or beta-lactose, corn sweeteners, natural and synthetic gums such as acacia, tragacanth or sodium oleate, sodium stearate, magnesium stearate, sodium benzoate, sodium acetate, sodium chloride, and the like. Disintegrators include, without limitation, starch, methyl cellulose, agar, bentonite, xanthan gum, and the like.

The compounds of the present invention can also be administered in the form of liposome delivery systems, such as small unilamellar vesicles, large unilamellar vesicles, and multilamellar vesicles. Liposomes can be formed from a variety of phospholipids, such as cholesterol, stearylamine or phophatidylcholines.

Compounds of the present invention may also be delivered by the use of monoclonal antibodies as individual carriers to which the compound molecules are coupled. The compounds of the present invention may also be coupled with soluble polymers as targetable drug carriers. Such polymers can include polyvinylpyrrolidone, pyran copolymer, polyhydroxypropylmethacrylamidephenol, polyhydroxyethylaspartamidephenol, or polyethyl-eneoxidepolylysine substituted with palmitoyl residue. Further more, the compounds of the present invention may be coupled to a class of biodegradable polymers useful in achieving controlled release of a drug, for example, polylactic acid, polyepsilon caprolactone, polyhydroxy butyric acid, polyesters, polyacetals, polydihydropyrans, polycyanoacrylates and cross-linked or amphipathic block copolymers of hydrogels.

Compounds of this invention may be administered in any of the foregoing compositions and according to dosage regimens established in the art whenever treatment of disorders or conditions mediated by the histamine $H_3$ receptor (e.g. ADHD) is required.

The daily dosage of the products may be varied over a wide range from 1 to 1,000 mg per adult human per day. For oral administration, the compositions are preferably provided in the form of tablets containing, 1.0, 5.0, 10.0, 15.0, 25.0, 50.0, 100, 250 and 500 milligrams of the active ingredient for the symptomatic adjustment of the dosage to the subject to be treated. An effective amount of the drug is ordinarily supplied at a dosage level of from about 0.01 mg/kg to about 20 mg/kg of body weight per day. Preferably, the range is from about 0.02 mg/kg to about 10 mg/kg of body weight per day, and especially from about 0.05 mg/kg to about 10 mg/kg of body weight per day. The compounds may be administered on a regimen of 1 to 4 times per day.

Optimal dosages to be administered may be readily determined by those skilled in the art, and will vary with the particular compound used, the strength of the preparation, the mode of administration, and the advancement of the disease condition. In addition, factors associated with the particular subject being treated, including subject age, weight, diet and time of administration, will result in the need to adjust dosages.

The methods of treatment described in the present invention (e.g. that of ADHD) may also be carried out using a pharmaceutical composition comprising any of the compounds as defined herein and a pharmaceutically acceptable carrier. The pharmaceutical composition may contain between about 5 mg and 1000 mg, preferably about 10 to 500 mg, of the compound, and may be constituted into any form suitable for the mode of administration selected. Carriers include necessary and inert pharmaceutical excipients, including, but not limited to, binders, suspending agents, lubricants, flavorants, sweeteners, preservatives, dyes, and coatings. Compositions suitable for oral administration include solid forms, such as pills, tablets, caplets, capsules (each including immediate release, timed release and sustained release formulations), granules, and powders, and liquid forms, such as solutions, syrups, elixirs, emulsions, and suspensions. Forms useful for parenteral administration include sterile solutions, emulsions and suspensions.

References are cited throughout the specification. These references in their entirety are incorporated herein by reference.

EXAMPLES

The following examples are intended to illustrate but not limit the invention. See also, N. S. Mani, et al., J. Org. Chem. 2004, 69, 8115-17.

General Experimental Methods:

NMR spectra were obtained on either a Bruker model DPX400 (400 MHz) or DPX500 (500 MHz) spectrometer. The format of the $^1$H NMR data below is: chemical shift in ppm down field of the tetramethylsilane reference (multiplicity, coupling constant J in Hz, integration). Mass spectra were obtained on an Agilent series 1100 MSD using electrospray ionization (ESI) in either positive or negative mode as indicated. The "mass calculated" for a molecular formula is the monoisotopic mass of the compound.

Melting points were determined by an Electrothermal apparatus and are uncorrected. IR spectra were recorded on a FTIR spectrophotometer.

Example I

Preparation of (4-Chloro-phenyl)-[2-(2-dimethylamino-ethylsulfanyl)-3-methyl-3H-imidazol-4-yl]-methanone

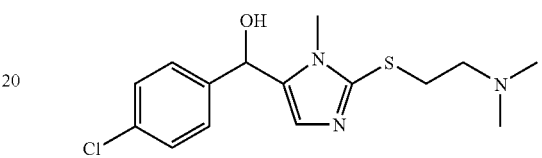

This example teaches the preparation of a compound of formula (I) following Scheme I, wherein M is —C(=O)R$^M$; R$^M$ is p-chlorophenyl; A$^3$ is sulfur; L$^3$ is ethyl; Q$^3$ is dimethylamino; and Q$^1$ is methyl.

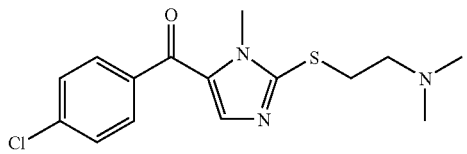

Step A: Preparation of (4-Chlorophenyl)-(2-mercapto-3-methyl-3H-imidazol-4-yl)-methanol. 2-Mercapto-1-methylimidazole (1.0 g) in THF (30 mL) under dry nitrogen at −78° C. was treated with t-BuLi (1.7 M in pentane, 11.3 mL). After stirring for 15 min, the reaction mixture was warmed to 0° C. After 30 min, the reaction was cooled to −78° C. and 4-chlorobenzaldehyde (1.5 g) in THF (20 mL) was added dropwise. After 1 h, the reaction was quenched with brine (100 mL) and slowly warmed to room temperature (rt). This mixture was partitioned between Et$_2$O (100 mL) and water (25 mL). The organic portion was separated, washed with brine (50 mL), dried over MgSO$_4$, filtered and evaporated. The residue was suspended in Et$_2$O and filtered off to provide as a white powder (4.4 g, 66%) the compound of formula (I) wherein M is —CHOHR$^M$; R$^M$ is p-chlorophenyl; Al is thiol (SH); L$^3$ is absent; Q$^3$ is absent; and Q$^1$ is methyl; also known as, (4-Chlorophenyl)-(2-mercapto-3-methyl-3H-imidazol-4-yl)-methanol. M calc=254; M+H found=255. Anal. Calcd for C$_{11}$H$_{11}$N$_2$OSCl: C, 51.87; H, 4.35; N, 11.00. Found: C, 51.97; H, 4.25; N, 10.81.

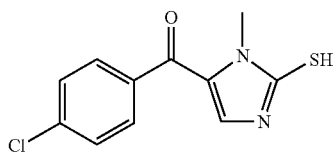

Step B: Preparation of (4-Chlorophenyl)-[2-(2-dimethylamino-ethylsulfanyl)-3-methyl-3H-imidazol-4-yl]-methanol. The product from Example I, Step A (0.1 g) in acetone (4 mL) was treated with K$_2$CO$_3$ (0.5 g) followed by dimethylaminoethyl chloride (0.2 g). The mixture was allowed to stir at rt for 16 h and was then partitioned between EtOAc (50 mL) and brine (50 mL). The organic layer was separated and washed with brine (2×200 mL), dried over Na$_2$SO$_4$, filtered, and concentrated to give the crude product. The crude product was purified by silica gel chromatography using 2% MeOH/CH$_2$Cl$_2$ as the eluent to provide 0.08 g (69% yield) of the compound of formula (I) wherein M is —CHOHR$^M$; R$^M$ is p-chlorophenyl; A$^3$ is sulfur; L$^3$ is ethyl; Q$^3$ is dimethylamino; and Q$^1$ is methyl; also known as (4-Chlorophenyl)-[2-(2-dimethylamino-ethylsulfanyl)-3-methyl-3H-imidazol-4-yl]-methanol. M calc=325; M+H found=326.

Step C: Preparation of (4-Chlorophenyl)-[2-(2-dimethylamino-ethylsulfanyl)-3-methyl-3H-imidazol-4-yl]methanone. The product of Example I, Step B (0.07 g) in CH$_2$Cl$_2$ (2 mL) was treated with MnO$_2$ (0.05 g). The reaction mixture was allowed to stir at rt for 1 h. The mixture was filtered through a pad of diatomaceous earth (5 g) and concentrated to provide (4-Chloro-phenyl)-[2-(2-dimethylamino-ethylsulfanyl)-3-methyl-3H-imidazol-4-yl]-methanone (0.06 g, 87%), M calc 323, M+H found=324; $^1$H NMR (400 MHz, CDCl$_3$): δ 7.78-7.66 (dm, J=8.5 Hz, 2H), 7.42 (s, 1H), 7.41-7.36 (dm, J=8.7 Hz, 2H), 3.82 (s, 3H), 3.38 (t, J=6.7 Hz, 2H), 2.64 (t, J=6.7 Hz, 2H), 2.25 (s, 6H). The compound demonstrated useful biological activity when assessed with a [$^3$H]—N-methylhistamine binding assay (see Table in Example XXV).

Step D: Additional compounds prepared following Scheme I and Example I, Steps A, B, and C. The following compounds of formula (I) were prepared following Scheme I and Example I, Steps A, B, and C; and substituting reagents, and adjusting reaction conditions as needed. The compounds were found to have useful biological activity based on the K$_i$ (nM) value from a [$^3$H]-N-methylhistamine binding assay.

The compounds of formula (I), wherein:

M is —CHOHR$^M$; R$^M$ is p-chlorophenyl; A$^3$ is sulfur; L$^3$ is n-propyl; Q$^3$ is dimethylamino; and Q$^1$ is methyl; also known as (4-Chlorophenyl)-[2-(3-dimethylamino-propylsulfanyl)-

3-methyl-3H-imidazol-4-yl]-methanol; M calc=339; M+H found=340; ¹H NMR (400 MHz, CDCl₃): δ 7.26-7.20 (m, 4H), 6.44 (s, 1H), 5.67 (s, 1H), 3.43 (s, 3H), 2.91 (t, J=7.2 Hz, 2H), 2.25-2.21 (t, J=7.4 Hz, 2H), 2.05 (s, 6H), 1.71-1.60 (m, 2H);

M is —CHOHR$^M$; R$^M$ is p-bromophenyl; A³ is thiol (SH); L³ is absent; Q³ is absent; and Q¹ is methyl; also known as (4-Bromophenyl)-(2-mercapto-3-methyl-3H-imidazol-4-yl)-methanol; M calc=298; M⁻ found=298;

M is —CHOHR$^M$; R$^M$ is p-chlorophenyl; A³ is sulfur; L³ is absent; Q³ is 4-methylpentyl; and Q¹ is methyl; also known as (4-Chlorophenyl)-[3-methyl-2-(4-methylpentylsulfanyl)-3H-imidazol-4-yl]-methanol; M calc=338; M+H found=339;

M is —C(=O)R$^M$; R$^M$ is p-chlorophenyl; A³ is sulfur; L³ is absent; Q³ is 4-methylpentyl; and Q¹ is methyl; also known as (4-Chlorophenyl)-[3-methyl-2-(4-methylpentylsulfanyl)-3H-imidazol-4-yl]-methanone; M calc=336; M+H found=337;

M is —CHOHR$^M$; R$^M$ is p-chlorophenyl; A³ is sulfur; L³ is n-propyl; Q³ is 1-piperidyl; and Q¹ is methyl; also known as (4-Chlorophenyl)-[3-methyl-2-(3-piperidin-1-yl-propylsulfanyl)-3H-imidazol-4-yl]-methanol; M calc=379; M+H found=380; ¹H NMR (400 MHz, CDCl₃): δ 7.32 (s, 4H), 6.55 (s, 1H), 5.77 (s, 1H), 3.57 (s, 3H), 3.00 (t, J=7.1 Hz, 2H), 2.34 (m, 6), 1.80 (m, 2H), 1.55 (m, 4H), 1.26 (br m, 2H);

M is —CHOHR$^M$; R$^M$ is p-chlorophenyl; A³ is sulfur; L³ is ethyl; Q³ is tetrahydropyran-2-yloxy; and Q¹ is methyl; also known as (4-Chloro-phenyl)-{3-methyl-2-[2-(tetrahydropyran-2-yloxy)-ethylsulfanyl]-3H-imidazol-4-yl}-methanol; M calc=382; M+H found=383; ¹H NMR (400 MHz, CDCl₃): δ 7.35-7.29 (m, 4H), 6.52 (s, 1H), 5.78 (s, 1H), 4.59-4.54 (m, 1H), 3.93-3.77 (m, 2H), 3.65-3.56 (m, 1H), 3.49-3.40 (m, 1H), 3.49 (s, 3H), 3.22 (t, J=6.6 Hz, 2H), 1.85-1.72 (m, 1H), 1.72-1.61 (m, 1H), 1.60-1.45 (m, 4H);

M is —CHOHR$^M$; R$^M$ is p-chlorophenyl; A³ is sulfur; L³ is absent; Q³ is 2-hydroxyethyl; and Q¹ is methyl; also known as, 2-{5-[(4-Chlorophenyl)-hydroxy-methyl]-1-methyl-1H-imidazol-2-ylsulfanyl}-ethanol; M calc=298; M+H found=299;

M is —CHOHR$^M$; R$^M$ is p-chlorophenyl; A³ is sulfur; L³ is ethyl; Q³ is cyclohexylsulfanyl; and Q¹ is methyl; also known as (4-Chloro-phenyl)-[2-(2-cyclohexylsulfanyl-ethylsulfanyl)-3-methyl-3H-imidazol-4-yl]-methanol; M calc=396; M+H found=397;

M is —C(=O)R$^M$; R$^M$ is prchlorophenyl; A³ is sulfur; L³ is ethyl; Q³ is tetrahydropyran-2-yloxy; and Q¹ is methyl; also known as (4-Chloro-phenyl)-{3-methyl-2-[2-(tetrahydropyran-2-yloxy)-ethylsulfanyl]-3H-imidazol-4-yl}-methanone; M calc=380; M+H found=381;

M is —C(=O)R$^M$; R$^M$ is p-chlorophenyl; A³ is sulfur; L³ is absent; Q³ is 2-hydroxyethyl; and Q¹ is methyl; also known as (4-Chlorophenyl)-[2-(2-hydroxyethylsulfanyl)-3-methyl-3H-imidazol-4-yl]-methanone; M calc=296; M+H found=297;

M is —C(=O)R$^M$; R$^M$ is p-chlorophenyl; A³ is sulfur; L³ is ethyl; Q³ is cyclohexylsulfanyl; and Q¹ is methyl; also known as (4-Chloro-phenyl)-[2-(2-cyclohexylsulfanyl-ethylsulfanyl)-3-methyl-3H-imidazol-4-yl]-methanone; ¹H NMR (400 MHz, CDCl₃): δ 7.70 (dm), 7.39 (dm), 3.82 (s), 3.41-3.38 (m), 2.90-2.81 (m); and M is hydrogen; A³ is sulfur; L³ is n-propyl; Q³ is dimethylamino; and Q¹ is methyl; also known as Dimethyl-[3-(1-methyl-1H-imidazol-2-ylsulfanyl)-propyl]-amine; M calc=199; M+H found=200.

Example II

Preparation of (4-Chlorophenyl)-[2-(3-dimethylamino-propylsulfanyl)-3-methyl-3H-imidazol-4-yl]-methanone

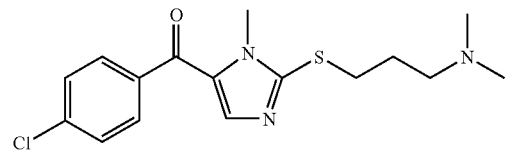

This example demonstrates the preparation of a compound of formula (I) following Scheme I, wherein M is —C(=O)R$^M$; R$^M$ is p-chlorophenyl; A³ is sulfur; L³ is n-propyl; Q³ is dimethylamino; and Q¹ is methyl. Alternatively, this compound can be prepared following Schemes II, IX, X, and XIV.

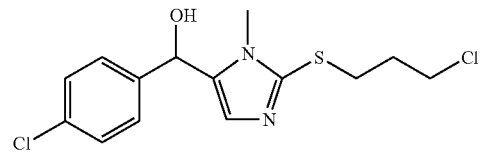

Step A: Preparation of (4-Chlorophenyl)-[2-(3-chloro-propylsulfanyl)-3-methyl-3H-imidazol-4-yl]-methanol. The product of Example I, Step A (0.09 g) in acetone (2 mL) and DMF (2 mL) was treated with K₂CO₃ (0.2 g) followed by 1-bromo-3-chloropropane (0.11 g). The mixture was allowed to stir at rt for 16 h and was then partitioned between EtOAc (50 mL) and brine (50 mL). The organic layer was separated and washed with brine (2×200 mL), dried over Na₂SO₄, filtered, and evaporated to give the crude product. The crude product was purified by silica gel chromatography using 2-5% MeOH/CH₂Cl₂ as the eluent to provide (4-Chloro-phenyl)-[2-(3-chloro-propylsulfanyl)-3-methyl-3H-imidazol-4-yl]-methanol (0.08 g, 69%); M calc=330; M+H found=331.

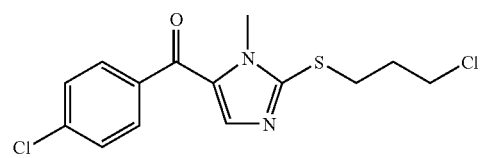

Step B: Preparation of (4-Chloro-phenyl)-[2-(3-chloro-propylsulfanyl)-3-methyl-3H-imidazol-4-yl]-methanone. The product of Example II, Step A (2.1 g) was subjected to the same conditions as described in Example I, Step C (MnO₂, 0.3 g) to provide (4-Chloro-phenyl)-[2-(3-chloro-propylsulfanyl)-3-methyl-3H-imidazol-4-yl]-methanone (1.7 g, 81%).

Step C: Preparation of (4-Chloro-phenyl)-[2-(3-dimethylamino-propylsulfanyl)-3-methyl-3H-imidazol-4-yl]methanone. The product from Example II, Step B (0.42 g) in acetone (25 mL) was treated with K₂CO₃ followed by dimethylamine hydrochloride (0.42 g). The mixture was allowed to stir at 60° C. overnight. The reaction mixture was cooled to rt and diluted with EtOAc (75 mL) and washed with brine (2×70 mL). The organic portion was dried over MgSO₄, filtered, and concentrated to give the crude product. The crude was purified by silica gel chromatography (1-10% 2 M NH₃ in MeOH/CH₂Cl₂) to provide (4-Chlorophenyl)-[2-(3-dimethylamino-propylsulfanyl)-3-methyl-3H-imidazol-4-yl]-methanone (25 mg, 6%), M calc=337, M+H found=338; $^1$H NMR (400 MHz, CDCl₃): δ 7.81-7.73 (dm, J=8.5 Hz, 2H), 7.50 (s, 1H), 7.48-7.44 (dm, J=8.6 Hz, 2H), 3.91 (s, 3H), 3.33 (t, J=7.1 Hz, 2H), 2.45 (t, J=7.1 Hz, 2H), 2.27 (s, 6H), 2.0-1.91 (m, 2H). The compound demonstrated useful biological activity when assessed with a [³H]-N-methylhistamine binding assay (see Table in Example XXV).

Step D: Additional compounds prepared following Scheme I and Example II, Steps A, B, and C. The following compounds of formula (I) were prepared following Scheme I and Example II, Steps A, B, and C; and substituting reagents, and adjusting reaction conditions as needed. The compounds were found to have useful biological activity based on the $K_i$ (nM) value from a [³H]-N-methylhistamine binding assay.

The compounds of formula (I) wherein:

M is —CHOHR$^M$; R$^M$ is p-bromophenyl; A³ is sulfur; L³ is absent; Q³ is 3-chloropropyl; and Q¹ is methyl; also known as (4-Bromophenyl)-[2-(3-chloro-propylsulfanyl)-3-methyl-3H-imidazol-4-yl]-methanol; M calc=374; M+H found=375;

M is —CHOHR$^M$; R$^M$ is p-bromophenyl; A³ is sulfur; L³ is n-propyl; Q³ is 1-piperidyl; and Q¹ is methyl; also known as (4-Bromophenyl)-[3-methyl-2-(3-piperidin-1-yl-propylsulfanyl)-3H-imidazol-4-yl]-methanol; M calc=423; M+H found=424; $^1$H NMR (400 MHz, CDCl₃): δ 7.41 (dd, J=8.6, 2.0 Hz, 2H), 7.2 (d, J=8.3 Hz, 2H), 6.5 (s, 1H), 5.69 (s, 1H), 3.39 (s, 3H), 2.94 (t, J=7.1Hz, 2H), 2.26 (m, 6H), 1.72 (m, 2H), 1.47 (m, 4H), 1.34 (br m, 2H);

M is —CHOHR$^M$; R$^M$ is p-chlorophenyl; A³ is sulfur; L³ is n-propyl; Q³ is 4-morpholinyl; and Q¹ is methyl; also known as, (4-Chlorophenyl)-[3-methyl-2-(3-morpholin-4-yl-propylsulfanyl)-3H-imidazol-4-yl]-methanol; M calc=381; M+H found=382;

M is —C(═O)R$^M$; R$^M$ is p-chlorophenyl; A³ is sulfur; L³ is n-propyl; Q³ is 4-morpholinyl; and Q¹ is methyl; also known as (4-Chlorophenyl)-[3-methyl-2-(3-morpholin-4-yl-propylsulfanyl)-3H-imidazol-4-yl]-methanone; M calc=379; M+H found=380;

M is —C(═O)R$^M$; R$^M$ is p-bromophenyl; A³ is sulfur; L³ is n-propyl; Q³ is cyclohexylamino; and Q¹ is methyl; also known as (4-Bromophenyl)-[2-(3-cyclohexylamino-propylsulfanyl)-3-methyl-3H-imidazol-4-yl]-methanone; M calc=435; M+H found=436;

M is —C(═O)R$^M$; R$^M$ is p-bromophenyl; A³ is sulfur; L³ is n-propyl; Q³ is benzylamino; and Q¹ is methyl; also known as [2-(3-Benzylamino-propylsulfanyl)-3-methyl-3H-imidazol-4-yl]-(4-bromo-phenyl)-methanone; M calc=443; M+H found=444;

M is —C(═O)R$^M$; R$^M$ is p-bromophenyl; A³ is sulfur; L³ is n-propyl; Q³ is 4-thiomorpholinyl; and Q¹ is methyl; also known as (4-Bromophenyl)-[3-methyl-2-(3-thiomorpholin-4-yl-propylsulfanyl)-3H-imidazol-4-yl]-methanone; M calc=439; M+H found=440; and M is —C(═O)R$^M$; R$^M$ is p-chlorophenyl; A³ is sulfur; L³ is n-propyl; Q³ is 1-piperidyl; and Q¹ is methyl; also known as (4-Chlorophenyl)-[3-methyl-2-(3-piperidin-1-yl-propylsulfanyl)-3H-imidazol-4-yl]-methanone; M calc=377; M+H found=378; $^1$H NMR (400 MHz, CDCl₃): δ 7.69 (dd, J=9.0, 2.3 Hz, 2H), 7.43 (s, 1H), 7.39 (dd, J=9.0, 2.3 Hz, 2H), 3.82 (s, 3H), 3.25 (t, J=7.1 Hz, 2H), 2.41 (br m, 4H), 1.95 (br m, 2H), 1.55 (br m, 4H), 1.36 (br m, 2H).

Example III

Preparation of (4-Bromophenyl)-[3-methyl-2-(3-piperidin-1-yl-propylsulfanyl)-3H-imidazol-4-yl methanone

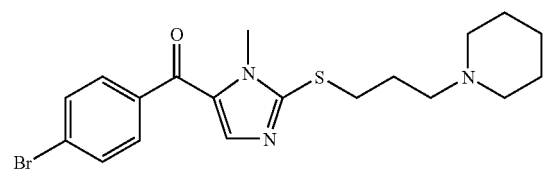

This example demonstrates the preparation of a compound of formula (I) following Scheme I, wherein M is —C(═O)R$^M$; R$^M$ is p-bromophenyl; A³ is sulfur; L³ is n-propyl; Q³ is 1-piperidyl; and Q¹ is methyl.

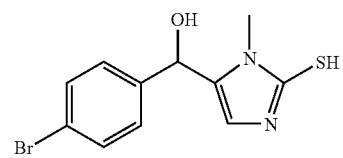

Step A: Preparation of (4-Bromophenyl)-(2-mercapto-3-3-methyl-3H-imidazol-4-yl)-methanol. The preparation of Example I, Step A was performed employing 2-Mercapto-1-methylimidazole (5.0 g) and 4-bromobenzaldehyde (9.7 g) to provide the above-identified compound as a white solid (3.0 g, 23%). M calc=298; M+H found=299.

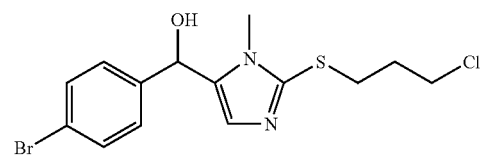

Step B: (4-Bromophenyl)-[2-(3-chloro-propylsulfanyl)-3-methyl-3H-imidazol-4-yl]-methanol. The product from Example III, Step A (3.0 g) was subjected to the same conditions as described in Example II, Step A employing 1-bromo-3-chloropropane (3.1 g) to provide the title compound (2.9 g, 77%) as a colorless oil. M calc=374; M+H found=375.

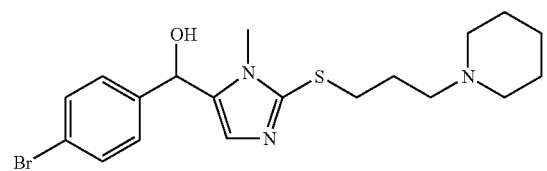

Step C: (4-Bromophenyl)-[3-methyl-2-(3-piperidin-1-yl-propylsulfanyl)-3H-imidazol-4-yl]-methanol. The product of Example III, Step B (0.11 g) in acetone (5 mL) and DMF (5 mL) was treated with piperidine (0.22 g) and K$_2$CO$_3$ (1.8 g). The reaction mixture was allowed to stir for 16 h and then partitioned between EtOAc (75 mL) and aqueous (aq.) saturated (satd.) NaHCO$_3$ (50 mL). The organic portion was washed with brine (50 mL), dried over MgSO$_4$, filtered and concentrated under reduced pressure. The residue was purified by column chromatography on silica gel using 2-5% MeOH/CH$_2$Cl$_2$ as the eluent to provide the title compound (0.27 g, 55%). M calc=423; M+H found=424.

Step D: (4-Bromophenyl)-[3-methyl-2-(3-piperidin-1-yl-propylsulfanyl)-3H-imidazol-4-yl]-methanone. The product from Example III, Step C (0.05 g) was subjected to the same conditions described in Example I, Step C (MnO$_2$, 0.05g) to provide the title compound (0.01 g, 20%). M calc=421; M+H found=422. $^1$H NMR (400 MHz, CDCl$_3$): δ 7.65 (dd, J=8.6, 2.0 Hz, 2H), 7.55 (dd, J=8.6, 2.0 Hz, 2H), 7.46 (s, 1H), 3.86 (s, 3H), 3.28 (t, J=7.1 Hz, 2H), 2.36 (tm, J=7.0 Hz, 6H), 1.91 (m, 2H), 1.55 (m, 4H), 1.40 (br m, 2H). The compound demonstrated useful biological activity when assessed with a [$^3$H]—N-methylhistamine binding assay (see Table in Example XXV).

Step E: Additional compounds prepared following Scheme I, and Example III, Steps A, B, C, and D. The following compounds of formula (I) were prepared following Scheme I and Example III, Steps A, B, C, and D; and substituting reagents, and adjusting reaction conditions as needed. The compounds were found to have useful biological activity based on the K$_i$ (nM) value from a [$^3$H]-N-methylhistamine binding assay.

The compounds of formula (I), wherein:

M is —CHOHR$^M$; R$^M$ is p-chlorophenyl; A$^3$ is sulfur; L$^3$ is absent; Q$^3$ is 3-chloropropyl; and Q$^1$ is methyl; also known as (4-Chlorophenyl)-[2-(3-chloro-propylsulfanyl)-3-methyl-3H-imidazol-4-yl]-methanol; M calc=330; M+H found=331;

M is —C(=O)R$^M$; R$^M$ is p-bromophenyl; A$^3$ is sulfur; L$^3$ is n-propyl; Q$^3$ is dimethylamino; and Q$^1$ is methyl; also known as (4-Bromophenyl)-[2-(3-dimethylamino-propylsulfanyl)-3-methyl-3H-imidazol-4-yl]-methanone; M calc=381; M+H found=382; $^1$H NMR (400 MHz, CDCl$_3$): δ 7.63 (dd, J=25.8, 8.7 Hz, 4H), 7.42 (s, 1H), 3.82 (s, 3H), 3.25 (t, J=14.3 Hz, 2H), 2.43 (t, J=17.1 Hz, 2H), 2.24 (s, 6H), 1.91 (m, 2H);

M is —C(=O)R$^M$; R$^M$ is p-chlorophenyl; A$^3$ is sulfur; L$^3$ is n-propyl; Q$^3$ is 1-(3,4-didehydropiperidyl); and Q$^1$ is methyl; also known as (4-Chloro-phenyl)-{2-[3-(3,4-didehydropiperidin-1-yl)-propylsulfanyl]-3-methyl-3H-imidazol-4-yl}-methanone; M calc=375; M+H found=376; $^1$H NMR (400 MHz, CDCl$_3$): δ 7.63 (d, J=8.1 Hz, 2H), 7.5 (d, J=8.1 Hz, 2H), 6.19 (s, 1H), 5.67 (s, 1H), 4.22 (s, 7H), 3.50 (s, 3H);

M is —C(=O)R$^M$; R$^M$ is p-chlorophenyl; A$^3$ is sulfur; L$^3$ is n-propyl; Q$^3$ is 4-thiomorpholinyl; and Q$^1$ is methyl; also known as (4-chloro-phenyl)-[3-methyl-2-(3-thiomorpholin-4-yl-propylsulfanyl)-3H-imidazol-4-yl]-methanone; M calc=395; M+H found=396;

M is —C(=O)R$^M$; R$^M$ is p-chlorophenyl; A$^3$ is sulfur; L$^3$ is n-propyl; Q$^3$ is 1-[1,4']Bipiperidyl; and Q$^1$ is methyl; also known as [2-(3-[1,4']Bipiperidinyl-1'-yl-propylsulfanyl)-3-methyl-3H-imidazol-4-yl]-(4-chloro-phenyl)-methanone; M calc=460; M+H found=461; and M is —C(=O)R$^M$; R$^M$ is p-bromophenyl; A$^3$ is sulfur; L$^3$ is absent; Q$^3$ is 3-chloropropyl; and Q$^1$ is methyl; also known as (4-Bromophenyl)-[2-(3-chloro-propylsulfanyl)-3-methyl-3H-imidazol-4-yl]-methanone; M calc=372; M+H found=373.

Example IV

Preparation of (4-Chloro-phenyl)-{3-methyl-2-[2-(1-methyl-pyrrolidin-2-yl)-ethylsulfanyl]-3H-imidazol-4-yl}-methanone

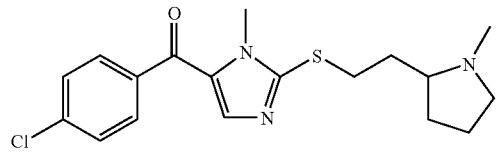

This example teaches the preparation of a compound of formula (I) following Scheme II, wherein M is —C(=O)R$^M$; R$^M$ is p-chlorophenyl; A$^3$ is sulfur; L$^3$ is ethyl; Q$^3$ is 2-(1-methyl-pyrrolidyl); and Q$^1$ is methyl.

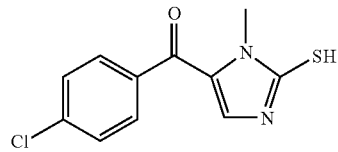

Step A: (4-Chlorophenyl)-(2-mercapto-3-methyl-3H-imidazol-4-yl)-methanone. To a −5° C. solution of monomethylamine (186 g, 6 mol) in 2 L of Et$_2$O was added a solution of p-chlorophenacylbromide (466 g, 2 mol) in 6 L of Et$_2$O. The temperature was maintained at 0° C. during the addition and stirring was continued for 2 h. The Et$_2$O and excess amine were distilled in vacuo leaving a slurry (3 L). The slurry was added to cold formyl acetic anhydride, which was prepared by heating a solution of acetic anhydride (816 mL) and formic acid (98%, 354 mL). The mixture was stored in the refrigerator overnight. The solids were then filtered and extracted with benzene. The ether was distilled in vacuo and the residue was dissolved in benzene and washed thoroughly with water and brine. The solution was dried over MgSO$_4$ and charcoal. After filtration and evaporation of the solvent, the oil was dissolved in Et$_2$O and seeded. The product precipitated and was filtered, and washed with Et$_2$O to produce adduct 8 (155 g). This compound was carried on without further purification. To a solution of dry benzene (25 mL) was added NaH (54.4%, 1.06 g), followed by absolute EtOH (1.15 g). After H$_2$ evolution ceased, ethyl formate (5.92 g) was added followed by adduct 8 (4.23 g). The mixture was allowed to stir for 72 h. The solvent was then evaporated and the residue was treated with water and benzene/Et$_2$O (1:1). The aqueous layer was acidified and the organic layer was extracted twice with 1 N NaOH. The combined aqueous extracts were acidified, EtOH (95%) was added with warming until the solution was homogeneous. Potassium thiocyanate (4.0 g) was added and after 2.5 h of heating on a steam bath, the crystals were collected to provide imidazole 9 (4-Chlorophenyl)-(2-mercapto-3-methyl-3H-imidazol-4-yl)-methanone (0.7 g). M calc=252; M+H found=253.

Step B: Preparation of (4-Chlorophenyl)-{3-methyl-2-[2-(1-methylpyrrolidin-2-yl)-ethylsulfanyl]-3H-imidazol-4-yl}-methanone. The product from Example IV, Step A (0.15 g) was subjected to the same conditions as described in Example II, Step C, using 2-(2-chloroethyl-1-methyl-pyrrolidine hydrochloride (0.16 g) to provide (4-Chlorophenyl)-{3-methyl-2-[2-( 1-methylpyrrolidin-2-yl)-ethylsulfanyl]-3H-imidazol-4-yl}-methanone (0.025 g, 11%). M calc=363; M+H found 364. $^1$H NMR (400 MHz, CDCl$_3$): δ7.68 (dd, J=8.9, 2.2 Hz, 2H), 7.43 (s, 1H), 7.38 (dd, J=9.0, 2.3 Hz, 2H), 3.82 (s, 3H), 3.28 (m, 1H), 3.15 (m, 1H), 3.04 (m, 1H), 2.28 (s, 3H), 2.15 (br m, 1H), 2.05 (br m, 1H), 1.95 (br m, 1H), 1.65 (br m, 3H), 1.48 (br m, 1H). The compound demonstrated useful biological activity when assessed with a [$^3$H]-N-methylhistamine binding assay (see Table in Example XXV).

Step C: Additional compounds prepared following Scheme II, and Example IV, Steps A, and B. The following compounds of formula (I) were prepared following Scheme II and Example IV, Steps A and B; and substituting reagents, and adjusting reaction conditions as needed. The compounds were found to have useful biological activity based on the $K_i$ (nM) value from a [$^3$H]—N-methylhistamine binding assay.

The compounds of formula (I), wherein:

M is —C(=O)R$^M$; R$^M$ is p-chlorophenyl; A$^3$ is sulfur; L$^3$ is 2-methylpropyl; Q$^3$ is dimethylamino; and Q$^1$ is methyl; also known as (4-Chloro-phenyl)-[2-(3-dimethylamino-2-methyl-propylsulfanyl)-3-methyl-3H-imidazol-4-yl]-methanone; M calc=351; M+H found=352; $^1$H NMR (400 MHz, CDCl$_3$): δ7.69 (dd, J=9.1, 2.5 Hz, 2H), 7.42 (s, 1H), 7.39 (dd, J=9.1, 2.3 Hz, 2H), 3.84 (s, 3H), 3.46 (dd, J=12.9, 5.3 Hz, 1H), 3.05 (m, 1H), 2.20 (br m, 9H), 1.0 (d, J=7.1 Hz, 3H);

M is —C(=O)R$^M$; R$^M$ is p-chlorophenyl; A$^3$ is sulfur; L$^3$ is absent; Q$^3$ is 4-(1-methyl-piperidyl); and Q$^1$ is methyl; also known as (4-Chloro-phenyl)-[3-methyl-2-(1-methyl-piperidin-4-ylsulfanyl)-3H-imidazol-4-yl]-methanone; M calc=349; M+H found=350; $^1$H NMR (400 MHz, CDCl$_3$): δ7.72 (dd, J=8.9, 2.3 Hz, 2H), 7.47 (s, 1H), 7.41 (dd, J=9.0,2.3 Hz, 2H), 3.86 (s, 3H), 3.75 (br s, 1H), 2.77 (br m, 2H), 2.28 (s, 3H), 2.15 (br m, 2H), 1.90 (br m, 2H);

M is —C(=O)R$^M$; R$^M$ is p-chlorophenyl; A$^3$ is sulfur; L$^3$ is n-propyl; Q$^3$ is 1-(4-methyl-piperazyl); and Q$^1$ is methyl; also known as (4-Chloro-phenyl)-{3-methyl-2-[3-(4-methyl-piperazin-1-yl)-propylsulfanyl]-3H-imidazol-4-yl}-methanone; M calc=392; M+H found 393; $^1$H NMR (400 MHz, CDCl$_3$): δ7.77-7.72 (dm, J=8.5 Hz, 2H), 7.47 (s,1H), 7.46-7.42 (dm, J=8.5 Hz, 2H), 3.87 (s, 3H), 3.30 (t, J=7.1 Hz, 2H), 2.63-2.32 (m, 8H), 2.28 (s, 3H), 1.97-1.89 (m, 2H); and M is —C(=O)R$^M$; R$^M$ is phenyl; A$^3$ is sulfur; L$^3$ is n-propyl; Q$^3$ is dimethylamino; and Q$^1$ is methyl; also known as [2-(3-Dimethylamino-propylsulfanyl)-3-methyl-3H-imidazol-4-yl]-phenyl-methanone; M calc=303; M+H found=304; $^1$H NMR (400 MHz, CDCl$_3$): δ7.63 (d, J=7.7 Hz, 2H), 7.41 (m, 1H), 7.30 (m, 3H), 3.73 (s, 3H), 3.15 (t, J=7.14 Hz, 2H), 2.1 (br m, 6H), 1.85 (br m, 2H), 1.1 (br m, 2H).

Example V

Preparation of (4-Chlorophenyl)-[2-(1-isopropylpiperidin-4-ylmethoxy)-3-methyl-3H-imidazol-4-yl]-methanone

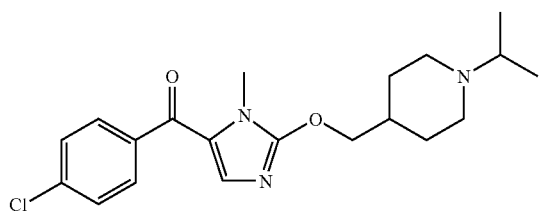

This example teaches the preparation of a compound of formula (I) following Scheme III, wherein M is —C(=O)R$^M$; R$^M$ is p-chlorophenyl; A$^3$ is oxygen; L$^3$ is methyl, Q$^3$ is 4-(1-isopropyl-piperidyl); and Q$^1$ is methyl.

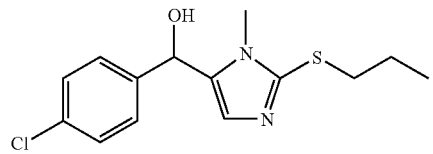

Step A: Preparation of (4-Chlorophenyl)-(3-methyl-2-propylsulfanyl-3H-imidazol-4-yl)-methanol. The product of Example I, Step A (3.35 g) was subjected to the same conditions as described in Example I, Step B except that bromopropane (1.4 mL) was employed as the alkylating agent to provide (4-Chlorophenyl)-(3-methyl-2-propylsulfanyl-3H-imidazol-4-yl)-methanol (2.69 g, 71%). M calc=296; M+H found=297. Calculated for C$_{14}$H$_{17}$N$_2$OSCl: C 56.65, H 5.77, 9.44; found C 55.88, H 5.88, N 9.84.

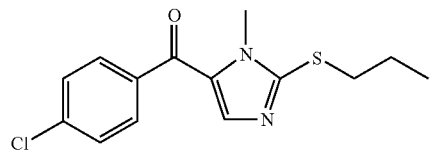

Step B: Preparation of (4-Chlorophenyl)-(3-methyl-2-propylsulfanyl-3H-imidazol-4-yl)-methanone. The product of Example V, Step A (2.69 g) was subjected to the same conditions as described in Example I, Step C (MnO$_2$, 3.39 g) to provide (4-Chlorophenyl)-(3-methyl-2-propylsulfanyl-3H-imidazol-4-yl)-methanone (2.67 g, 85%). M calc=294; M+H found=295. Anal. Calcd for C$_{14}$H$_{15}$N$_2$OSCl: C, 57.04; H, 5.13; N, 9.50. Found: C, 57.23; H, 4.99; N, 9.43.

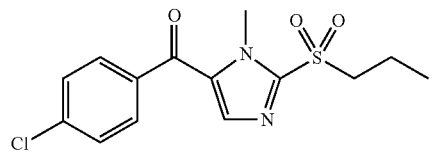

Step C: Preparation of (4-Chlorophenyl)-[3-methyl-2-(propane-1-sulfonyl)-3H-imidazol-4-yl]-methanone. The product of Example V, Step B (2.26 g) in CH$_2$Cl$_2$ (300 mL) at 0° C. was treated with mCPBA, (57%, 2.58 g). After 2 h, the reaction mixture was warmed to rt. After stirring overnight, additional mCPBA (57%, 1.6 g) was added. After 4 h, the mixture was partitioned between CH$_2$Cl$_2$ and aq. satd. NaHCO$_3$. The organic portion was separated, washed three times with aq. satd. NaHCO$_3$, dried over Na$_2$SO$_4$, filtered and concentrated to provide (4-chloro-phenyl)-[3-methyl-2-(propane-1-sulfonyl)-3H-imidazol-4-yl]-methanone (2.3 g, 93%). M calc=326; M+H found=327. Anal. Calcd for C$_{14}$H$_{15}$N$_2$O$_3$SCl: C, 51.45; H, 4.63; N, 8.57. Found: C, 51.73; H, 4.55; N, 8.56. $^1$H NMR (400 MHz, CDCl$_3$): δ7.98 (d, 2H), 7.68 (d, 2H), 7.44 (s, 1H), 4.46 (s, 3H), 3.76-3.70 (m, 2H), 1.95-1.83 (m, 2H), 1.29 (t, 3H).

Step D: Preparation of (4-Chlorophenyl)-[2-(1-isopropyl-piperidin-4-ylmethoxy)-3-methyl-3H-imidazol-4-yl]-methanone. (1-Isopropyl-piperidin-4-yl)-methanol (0.08 g) in THF (10 mL) was treated with NaH (60% in mineral oil, 0.02 g). After 30 min, the reaction mixture was cooled to 0° C. and the product of Example V, Step C (0.125 g) in THF (5 mL) was added. After stirring overnight, the reaction mixture was partitioned between brine and EtOAc. The organic portion was separated, washed twice with brine, dried over Na$_2$SO$_4$, filtered and concentrated. The residue was purified by column chromatography with silica gel using a gradient elution of 1-4% MeOH in CH$_2$Cl$_2$ to provide (4-Chloro-phenyl)-[2-(1-isopropyl-piperidin-4-ylmethoxy)-3-methyl-3H-imidazol-4-yl]-methanone (0.07, 51 %) as a white solid. M calc=375; M+H found=376. $^1$H NMR (400 MHz, CDCl$_3$): δ7.66 (d, J=8.3 Hz, 2H), 7.37 (d, J=8.6 Hz, 2H), 7.13 (s, 1H), 4.24 (d, J=6.1Hz, 2H), 3.69 (s, 3H), 2.88 (br d, J=11.0 Hz, 2H), 2.69 (m, 1H), 2.12 (br dd, J=12.6, 9.6 Hz, 2H), 1.88-1.69 (br m, 1H), 1.37 (br dd (J=23.2, 9.3 Hz, 2H), 0.99 (d, J=6.6 Hz, 6H). The compound demonstrated useful biological activity when assessed with a [$^3$H]—N-methylhistamine binding assay (see Table in Example XXV).

Step E: Additional compounds prepared following Scheme III, and Example V, Steps A, B, C, and D. The following compounds of formula (I) were prepared following Scheme III and Example V, Steps A, B, C, and D; and substituting reagents, and adjusting reaction conditions as needed. The compounds were found to have useful biological activity based on the K$_i$ (nM) value from a [$^3$H]—N-methylhistamine binding assay.

The compounds of formula (I), wherein:

M is —C(=O)R$^M$; R$^M$ is p-chlorophenyl; A$^3$ is sulfoxide (S=O); L$^3$ is absent; Q$^3$ is methyl; and Q$^1$ is methyl; also known as (4-Chloro-phenyl)-(2-methanesulfinyl-3-methyl-3H-imidazol-4-yl)-methanone; M calc=282; M+H found=283;

M is —C(=O)R$^M$; R$^M$ is pchlorophenyl; A$^3$ is oxygen; L$^3$ is ethyl; Q$^3$ is 1-piperidyl; and Q$^1$ is methyl; also known as (4-Chlorophenyl)-[3-methyl-2-(2-piperidin-1-yl-ethoxy)-3H-imidazol-4-yl]-methanone; M calc=347; M+H found=348; $^1$H NMR (400 MHz, CDCl$_3$): δ7.67 (dm, J=8.6 Hz, 2H), 7.37 (dm, J=8.6 Hz, 2H), 7.14 (s, 1H), 4.52 (t, J=5.8 Hz, 2H), 3.69 (s, 3H), 2.74 (t, J=5.8 Hz, 2H), 2.49-2.40 (m, 4H), 1.57-1.48 (m, 4H), 1.42-1.32 (m, 2H);

M is —C(=O)R$^M$; R$^M$ is pchlorophenyl; A$^3$ is oxygen; L$^3$ is n-propyl; Q$^3$ is 1-piperidyl; and Q$^1$ is methyl; also known as (4-Chlorophenyl)-[3-methyl-2-(3-piperidin-1-yl-propoxy)-3H-imidazol-4-yl]-methanone; M calc=361; M+H found=362; $^1$H NMR (400 MHz, CDCl$_3$): δ7.67 (d, J=8.6 Hz, 2H), 7.38 (d, J=8.6 Hz, 2H), 7.14 (s, 1H), 4.44 (t, J=7.0 Hz, 2H), 3.67 (s, 3H), 2.40 (t, J=7.3 Hz, 2H), 2.37-2.29 (br m, 2H), 2.00-1.91 (m, 2H), 1.57-1.48 (m, 4H), 1.41-1.33 (m, 2H);

M is —C(=O)R$^M$; R$^M$ is p-chlorophenyl; A$^3$ is NH; L$^3$ is n-propyl; Q$^3$ is 1-piperidyl; and Q$^1$ is methyl; also known as (4-Chlorophenyl)-[3-methyl-2-(3-piperidin-1-yl-propylamino)-3H-imidazol-4-yl]-methanone; $^1$H NMR (400 MHz, CDCl$_3$): δ7.75 (d, J=8.3 Hz, 2H), 7.46 (d, J=8.1Hz, 2H), 7.21 (s, 1H), 4.51 (t, J=6.3 Hz, 2H), 3.76 (s, 3H), 2.47-2.32 (tm, J=6.8 Hz, 6H), 2.10-1.95 (m, 2H), 1.66-1.53 (m, 4H), 1.49-1.37 (m, 2H);

M is —C(=O)R$^M$; R$^M$ is p-bromophenyl; A$^3$ is oxygen; L3 is n-propyl; Q$^3$ is 1-piperidyl; and Q$^1$ is methyl; also known as (4-Bromophenyl)-[3-methyl-2-(3-piperidin-1-yl-propoxy)-3H-imidazol-4-yl]-methanone; M calc=405; M+H found=406;

M is —C(=O)R$^M$; R$^M$ is p-bromophenyl; A$^3$ is oxygen; L$^3$ is absent; Q$^3$ is 4-(1-isopropyl-piperidyl); and Q$^1$ is methyl; also known as (4-Bromo-phenyl)-[2-(1-isopropyl-piperidin-4-yloxy)-3-methyl-3H-imidazol-4-yl]-methanone; M calc=405; M+H found=406; $^1$H NMR (400 MHz, CDCl$_3$): δ7.60 (dd, J=8.3, 2.0 Hz, 2H), 7.54 (dd, J=8.6, 2.0 Hz, 2H), 7.14 (s, 1H), 4.93 (m, 1H), 3.68 (s, 3H), 2.78-2.62 (m, 3H), 2.38 (br t, J=8.6 Hz, 2H), 2.13-1.99 (m, 2H), 1.88-1.75 (m, 2H), 0.99 (d, J=6.6 Hz, 6H);

M is —C(=O)R$^M$; R$^M$ is p-bromophenyl; A$^3$ is oxygen; L$^3$ is methyl; Q$^3$ is 4-(1-isopropyl-piperidyl); and Q$^1$ is methyl; also known as (4-Bromophenyl)-[2-(1-isopropyl-piperidin-4-ylmethoxy)-3-methyl-3H-imidazol-4-yl]-methanone; M calc=419; M+H found=420; $^1$H NMR (400 MHz, CDCl$_3$): δ7.59 (dd, J=8.1, 2.0 Hz, 2H), 7.54 (dd, J=8.6, 1.8 Hz, 2H), 7.13 (s, 1H), 4.24 (d, J=6.0 Hz, 2H), 3.68 (s, 3H), 2.88 (br d, J=11.9 Hz, 2H), 2.74-2.62 (m, 1H), 2.11 (td, J=11.9, 2.5 Hz, 2H), 1.85-1.71 (br m, 3H), 1.37 (br dd, J=12.4, 3.5 Hz, 2H), 0.99 (d, J=6.8 Hz, 6H);

M is —C(=O)R$^M$; R$^M$ is p-chlorophenyl; A$^3$ is oxygen; L$^3$ is n-propyl; Q$^3$ is dimethylamino; and Q$^1$ is methyl; also known as (4-Chlorophenyl)-[2-(3-dimethylamino-propoxy)-3-methyl-3H-imidazol-4-yl]-methanone; M calc=321; M+H found=322; $^1$H NMR (400 MHz, CD$_3$OD): δ7.78-7.72 (dm, J=8.4 Hz, 2H), 7.48-7.43 (dm, J=6.7 Hz, 2H), 7.22 (s, 1H), 4.53 (t, J=6.2 Hz, 2H), 3.75 (s, 3H), 2.46 (t, J=7.1 Hz, 2H), 2.27 (s, 6H), 2.08-1.73 (m, 2H);

M is —C(=O)R$^M$; R$^M$ is p-bromophenyl; A$^3$ is oxygen; L$^3$ is methyl; Q$^3$ is 1-tert-butoxycarbonyl-piperidin-4-yl; and Q$^1$ is methyl; also known as 4-[5[(4-bromobenzoyl)-1-methyl-1H-imidazol-2-yloxymethyl]-piperidine-1-carboxylic acid tert-butyl ester; M calc=477; M+H found=478;

M is —C(=O)R$^M$; R$^M$ is p-bromophenyl; A$^3$ is oxygen; L$^3$ is ethyl; Q$^3$ is 1-(4-isopropylpiperazyl); and Q$^1$ is methyl; also known as (4-Bromophenyl)-{2-[2-(4-isopropyl-piperazin-1-yl)-ethoxy]-3-methyl-3H-imidazol-4-yl}-methanone; M calc=434; M+H found=435; $^1$H NMR (400 MHz, CDCl$_3$): δ7.62-7.57 (dm, J=8.4 Hz, 2H), 7.57-7.52 (dm, J=8.3 Hz, 2H), 7.14 (s, 1H), 4.52 (t, J=5.7 Hz, 2H), 3.68 (s, 3H), 2.77 (t, J=5.7 Hz, 2H), 2.64-2.40 (m, 8H), 1.85 (br s, 1H), 0.98 (d, J=6.5 Hz, 6H);

M is —C(=O)R$^M$; R$^M$ is phenyl; A$^3$ is oxygen; L$^3$ is n-propyl; Q$^3$ is 1-piperidyl; and Q$^1$ is methyl; also known as [3-Methyl-2-(3-piperidin-1-yl-propoxy)-3H-imidazol-4-yl]-phenyl-methanone; M calc=327; M+H found=328; and M is —C(=O)R$^M$; R$^M$ is p-bromophenyl; A$^3$ is oxygen; L$^3$ is ethan-1-yl-2-ylidene; Q$^3$ is 4-(1-isopropyl-piperidyl); and Q$^1$ is methyl; also known as (4-Bromophenyl)-{2-[2-(1-isopropyl-piperidin-4-ylidene)-ethoxy]-3-methyl-3H-imidazol-4-yl}-methanone; $^1$H NMR (400 MHz, CDCl$_3$): δ7.57 (dd, J=22.4, 8.4 Hz, 4H), 7.14 (s, 1H), 5.43 (t, J=7.2 Hz, 1H), 4.90 (d, J=7.1 Hz, 1H), 3.68 (s, 3H), 2.74-2.65 (m, 1H), 2.46 (ddd, J=11.2, 5.5, 5.5 Hz, 4H), 2.32 (t, J=5.5 Hz, 2H), 2.23 (t, J=5.5 Hz, 2H), 0.97 (d, J=6.6 Hz, 6H).

Step F: Additional compounds that can be prepared following Scheme III and Example V, Steps A, B, C, and D, and E. The following compound of formula (I) was prepared by first following Scheme III and Example V, Steps A, B, C, D, and E to prepare 4-[5[(4-bromobenzoyl)-1-methyl-1H-imidazol-2-yloxymethyl]-piperidine-1-carboxylic acid tert-butyl ester (see Step E above). This intermediate was then treated with trifluoroacetic acid in CH$_2$Cl$_2$ under standard tert-butoxycarbonyl removal conditions to yield the compound of formula (I) wherein:

M is —C(=O)R$^M$; R$^M$ is p-bromophenyl; A$^3$ is oxygen; L$^3$ is methyl; Q$^3$ is 4-piperidyl; and Q$^1$ is methyl; also known as (4-Bromophenyl)-[3-methyl-2-(piperidin-4-ylmethoxy)-3H-imidazol-4-yl]-methanone; $^1$H NMR (400 MHz, CDCl$_3$/CD$_3$OD (~1:1)): 67.57 (m, 4H), 7.13 (s, 1H), 4.27 (d, 2H), 3.69 (s, 3H), 3.40 (m, 2H), 2.86 (m, 2H), 2.10 (brs, 1H), 1.96 (m, 2H), 1.59 (m, 2H).

Step G: Additional compounds that can be prepared following Scheme III and Example V, Steps A, B, C, D, E and F. The following compounds of formula (I) were prepared by first following Scheme III and Example V, Steps A, B, C, D, E, and F to prepare (4-Bromophenyl)-[3-methyl-2-(piperidin-4-ylmethoxy)-3H-imidazol-4-yl]-methanone (see Step F above). This intermediate was then subjected to the reductive amination procedure outlined in Example XV, using the appropriate aldehydes to yield the compounds of formula (I) wherein:

M is —C(=O)R$^M$; R$^M$ is p-bromophenyl; A$^3$ is oxygen; L$^3$ is ethyl; Q$^3$ is 4-(1-isopropylpiperidyl); and Q$^1$ is methyl; also known as (4-Bromophenyl)-{2-[2-(1-isopropyl-piperidin-4-yl)-ethoxy]-3-methyl-3H-imidazol-4-yl}-methanone; M calc=433; M+H found=434; $^1$H, (500 MHz, CDCl$_3$): δ7.62-7.57 (dm, J=8.5 Hz, 2H), 7.56-7.53 (dm, J=8.5 Hz, 2H), 7.12 (s, 1H), 4.44 (t, J=6.6 Hz, 2H), 3.68 (s, 3H), 3.12-2.72 (m, 3H), 2.36-2.10 (m, 2H), 1.88-1.64 (m, 3H), 1.18-0.97 (m, 6H);

M is —C(=O)R$^M$; R$^M$ is p-bromophenyl; A$^3$ is oxygen; L$^3$ is methyl; Q$^3$ is 4-(1-ethyl-piperidyl); and Q$^1$ is methyl; also known as (4-Bromophenyl)-[2-(1-ethyl-piperidin-4-ylmethoxy)-3-methyl-3H-imidazol-4-yl]-methanone; $^1$H NMR (400 MHz, CDCl$_3$): δ7.35 (s, 4H), 6.69 (s, 1H), 5.83 (s, 1H), 3.49 (s, 3H), 3.08 (m, 2H), 1.65 (m, 3H), 1.53 (m, 2H), 1.27 (m, 3H), 0.86 (d, J=6.6 Hz, 6H);

M is —C(=O)R$^M$; R$^M$ is p-bromophenyl; A$^3$ is oxygen; L$^3$ is methyl; Q$^3$ is 4-(1-sec-butyl-piperidyl); and Q$^1$ is methyl; also known as (4-Bromophenyl)-[2-(1-sec-butyl-piperidin-4-ylmethoxy)-3-methyl-3H-imidazol-4-yl]-methanone; $^1$H NMR (400 MHz, CDCl$_3$): δ7.70 (dd, J=8.3, 2.3 Hz, 2H), 7.65 (dd, J=8.6, 2.0 Hz, 2H), 7.30 (s, 1H), 4.35 (d, J=6.3 Hz, 2H), 3.8 (s, 3H), 2.9 (br m, 1H), 2.85 (br m, 2H), 0.9 (m, 3H), 0.8 (m, 3H);

M is —C(=O)R$^M$; R$^M$ is p-bromophenyl; A$^3$ is oxygen; L$^3$ is methyl; Q$^3$ is 4-(1-methyl-piperidyl); and Q$^1$ is methyl; also known as (4-Bromophenyl)-[3-methyl-2-(1-methyl-piperidin-4-ylmethoxy)-3H-imidazol-4-yl]-methanone; $^1$H NMR (400 MHz, CDCl$_3$): δ7.58 (dd, J=20.9, 8.8 Hz, 4H), 7.14 (s, 1H), 4.26 (d, J=6.1 Hz, 2H), 3.69 (s, 3H), 2.85 (d, J=11.4 Hz, 2H), 1.58 (br s, 5H), 1.40 (m, 3H);

M is —C(=O)R$^M$; R$^M$ is p-bromophenyl; A$^3$ is oxygen; L$^3$ is methyl; Q$^3$ is 4-[1-(3-methylbutyl)-piperidyl]; and 01 is methyl; also known as (4-Bromophenyl)-{3-methyl-2-[1-(3-methyl-butyl)-piperidin-4-ylmethoxy]-3H-imidazol-4-yl}-methanone; M calc=447; M+H found=448;

M is —C(=O)R$^M$; R$^M$ is p-bromophenyl; A$^3$ is oxygen; L$^3$ is methyl; Q$^3$ is 4-(1'-isopropyl-[1,4']bipiperidyl); and Q$^1$ is methyl; also known as (4-Bromophenyl)-[2-(1'-isopropyl-[1,4']bipiperidinyl-4-ylmethoxy)-3-methyl-3H-imidazol-4-yl]-methanone; M calc=502; M+H found=503; and M is —C(=O)R$^M$; R$^M$ is p-bromophenyl; A$^3$ is oxygen; L$^3$ is methyl; Q$^3$ is 4-(1-cyclohexyl-piperidyl); and Q$^1$ is methyl; also known as (4-Bromophenyl)-[2-(1-cyclohexyl-piperidin-4-ylmethoxy)-3-methyl-3H-imidazol-4-yl]-nethanone; M calc=459; M+H found=460; $^1$H NMR (400 MHz, CDCl$_3$): δ7.62-7.57 (m, 2H), 7.56-7.51 (m, 2H), 7.14-7.11 (m, 1H), 4.32-4.21 (m, 2H), 3.71-3.66 (m, 3H), 3.20-3.03 (m, 1H), 3.00-2.87 (m, 1H), 2.57-2.46 (m, 1H), 2.46-2.25 (m, 1H), 2.05-1.88 (m, 2H), 1.88-1.69 (m, 4H), 1.69-1.42 (m, 6H), 1.32-1.13 (m, 3H), 1.13-1.10 (m,1H).

Example XI

Preparation of (4-Chlorophenyl)-[2-(1-isopropyl-piperidin-4-yloxy)-3-methyl-3H-imidazol-4-yl]-methanone

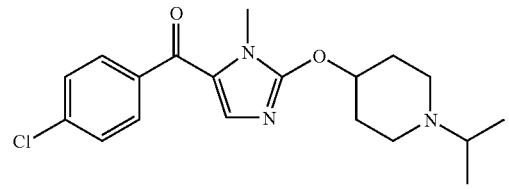

This example teaches the preparation of a compound of formula (I) following Scheme IX, wherein M is —C(=O)R$^M$; R$^M$ is p-chlorophenyl; A$^3$ is oxygen; L$^3$ is absent; Q$^3$ is 1-isopropyl-piperidin-4-yl; and Q$^1$ is methyl.

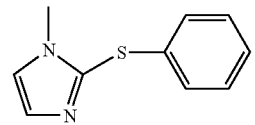

Step A: Preparation of 1-Methyl-2-phenylsulfanyl-1H-imidazole. To a stirred –78° C. solution of 1-Methyl-1H-imidazole (3.00 mL) in dry THF (120 mL) was added n-BuLi (15.0 mL, 2.50 M in hexanes). The reaction solution was stirred for 20 min at –78° C. and diphenyldisulfide (8.21 g) was added. The reaction mixture was stirred for 15 min at –78° C. and was allowed to warm to rt over 45 min. Water (25.0 mL) was added and the solvent was removed in vacuo. The residue was dissolved in CH$_2$Cl$_2$ (500 mL) and the organic layer was washed with water (2×50.0 mL). The organic layer was dried over MgSO$_4$ and the solvent was removed in vacuo. The residue was purified by flash chromatography on silica gel (hexanes/acetone) to give the title compound (5.85 g).

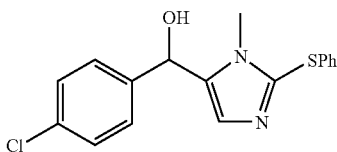

Step B: Preparation of (4-Chlorophenyl)-(3-methyl-2-phenylsulfanyl-3H-imidazol-4-yl)-methanol. To a stirred −78° C. solution of 2,2,6,6-tetramethylpiperidine (3.54 mL) in dry THF (50.0 mL) and 1,2-dimethoxyethane (DME, 20.0 mL) was added n-BuLi (8.00 mL, 2.50 M in hexanes). The solution was stirred for 15 min at −78° C. and a solution of the product of Example XI, Step A (3.81 g) in dry THF (5.00 mL) was added at −78° C. The reaction mixture was allowed to warm to rt and was stirred for 12 h at rt. Water (10.0 mL) was added and the solvent was removed in vacuo. The residue was dissolved in $CH_2Cl_2$ (650 mL) and the organic layer was washed with water (2×150 mL). The organic layer was dried over $MgSO_4$ and the solvent was removed in vacuo. The residue was purified by flash chromatography on silica gel (hexanes/acetone) to give the title compound (4.60 g).

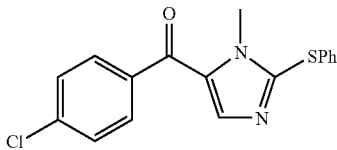

Step C: Preparation of (4-Chlorophenyl)-(3-methyl-2-phenylsulfanyl-3H-imidazol-4-yl)-methanone. To a stirred solution of the product of Example XI, Step B (1.00 g) in dry $CH_2Cl_2$ (250.0 mL) at rt was added $MnO_2$ (3.02 g). The reaction mixture was stirred for 24 h at rt and was filtered through diatomaceous earth. The solvent was removed in vacuo and the residue was purified by flash chromatography (hexanes/acetone) to give the title compound (620 mg).

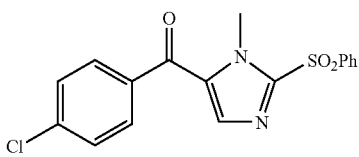

Step D: Preparation of (2-Benzenesulfonyl-3-methyl-3H-imidazol-4-yl)-(4-chlorophenyl)-methanone. To a stirred solution of the product of Example XI, Step C (620 mg) in $Et_2O$ (100 mL) at rt was added 3-chloroperoxybenzoic acid (57%, 2.86 g). The reaction solution was stirred for 6 h at rt and $Et_2O$ (650 mL) was added. The organic layer was washed with satd. $NaHCO_3$ (3×150 mL), water (150 mL) and brine (150 mL) and was dried over $MgSO_4$. The solvent was removed in vacuo and the residue was purified by flash chromatography on silica gel (hexanes/acetone) to give the material (802 mg) containing the title compound, which was used without additional purification.

Step E: Preparation of (4-Chlorophenyl)-[2-(1-isopropyl-piperidin-4-yloxy)-3-methyl-3H-imidazol-4-yl]-methanone. To a stirred solution of 1-isopropyl-piperidin-4-ol (301 mg) in dry THF (10.0 mL) at rt was added NaH (60% dispersion in mineral oil, 76.0 mg). The reaction mixture was stirred for 30 min at rt and a solution of the product of Example XI, Step D (150 mg) in dry THF (1.00 mL) was added. The reaction mixture was stirred for 18 h at rt and water (1.00 mL) was added. The solvent was removed in vacuo and the residue was dissolved in $CH_2Cl_2$ (300 mL). The organic layer was washed with satd. $NaHCO_3$ (2×50.0 mL) and water (50.0 mL) and was dried over $MgSO_4$. The solvent was removed in vacuo and the residue was purified by flash chromatography on silica gel ($CHCl_3/NH_3$, 2 M in MeOH) to give the title compound (82.0 mg). M calc=361, M+H found=362; $^1$H NMR (400 MHz, $CD_3OD$): δ7.83-7.76 (dm, J=8.4 Hz, 2H), 7.57-7.50 (dm, J=9.0 Hz, 2H), 7.26 (s,1H), 4.50-4.92 (m,1H), 3.75 (s, 3H), 2.92-2.70 (m, 3H), 2.59-2.45 (m, 2H), 2.20-2.04 (m, 2H), 2.00-1.80 (m, 2H), 1.11 (d, J=6.5 Hz, 6H). The compound demonstrated useful biological activity when assessed with a [$^3$H]—N-methylhistamine binding assay (see Table in Example XXV).

Step F: Additional compounds prepared following Scheme IX, and Example XI, Steps A, B, C, D, and E. The following compounds of formula (I) were prepared following Scheme IX and Example XI, Steps A, B, C, D, and E; and substituting reagents, and adjusting reaction conditions as needed. The compounds were found to have useful biological activity based on the $K_i$ (nM) value from a [$^3$H]—N-methylhistamine binding assay.

The compounds of formula (I), wherein:

M is —C(=O)$R^M$; $R^M$ is methyl; $A^3$ is sulfur; $L^3$ is n-propyl; $Q^3$ is dimethylamino; and $Q^1$ is methyl; also known as 1-[2-(3-Dimethylamino-propylsulfanyl)-3-methyl-3H-imidazol-4-yl]-ethanone; M calc=241; M+H found=242; $^1$H NMR (400 MHz, $CDCl_3$): δ7.76 (s, 1H), 3.83 (s, 3H), 3.39 (t, J=6.4 Hz, 2H), 2.43-2.38 (m, 5H), 2.23 (s, 6H), 1.95-1.88 (m, 2H);

M is —C(=O)$R^M$; $R^M$ is p-chlorophenyl; $A^3$ is sulfur; $L^3$ is n-propyl; $Q^3$ is dimethylamino; and $Q^1$ is methyl; also known as (4-Chlorophenyl)-[2-(3-dimethylamino-propylsulfanyl)-3-methyl-3H-imidazol-4-yl]-methanone; M calc=337; M+H found=338; $^1$H NMR (400 MHz, $CDCl_3$): δ7.81-7.73 (dm, J=8.5 Hz, 2H), 7.50 (s,1H), 7.48-7.44 (dm, J=8.6 Hz, 2H), 3.91 (s, 3H), 3.33 (t, J=7.1 Hz, 2H), 2.45 (t, J=7.1 Hz, 2H), 2.27 (s, 6H), 2.0-1.91 (m, 2H);

M is —C(=O)$R^M$; $R^M$ is p-chlorophenyl; $A^3$ is oxygen; $L^3$ is absent; $Q^3$ is 4-(piperidin-1-ylmethyl)phenyl; and $Q^1$ is methyl; also known as (4-Chlorophenyl)-[3-methyl-2-(4-piperidin-1-ylmethyl-phenoxy)-3H-imidazol-4-yl]-methanone; M calc=409; M+H found=410;

M is —C(=O)$R^M$; $R^M$ is methyl; $A^3$ is oxygen; $L^3$ is propyl; $Q^3$ is 1-piperidyl; and $Q^1$ is methyl; also known as 1-[3-Methyl-2-(3-piperidin-1-yl-propoxy)-3H-imidazol-4-yl]-ethanone; M calc=265; M+H found=266; and M is —C(=O)$R^M$; $R^M$ is p-chlorophenyl; $A^3$ is sulfur; $L^3$ is absent; $Q^3$ is 4-(1-isopropyl-piperidyl); and $Q^1$ is methyl; also known as (4-Chlorophenyl)-[2-(1-isopropyl-piperidin-4-ylsulfanyl)-3-methyl-3H-imidazol-4-yl]-methanone; M calc=377; M+H found=378; $^1$H NMR (400 MHz, $CD_3OD$): δ7.85-7.79 (dm, J=8.4 Hz, 2H), 7.58-7.51 (m, 3H), 3.94 (s, 3H), 3.68-3.63 (m, 1H), 2.97-2.86 (m, 2H), 2.80-2.72 (m, 1H), 2.38 (t, J=10.9 Hz, 2H), 2.17-2.05 (m, 2H), 1.82-1.68 (m, 2H), 1.09 (d, J=6.6 Hz, 6H).

Step G: Additional compounds that can be prepared following Scheme IX and Example XI, Steps A, B, C, D, and E. The following compound of formula (I) was prepared by first following Scheme IX and Example XI, Steps A, B, C, D, and E to prepare the compound wherein M is —C(=O)R$^M$; R$^M$ is p-chlorophenyl; A$^3$ is sulfur; L$^3$ is n-propyl; Q$^3$ is 2-(1,3-dioxolanyl); and Q$^1$ is methyl (that is, (4-Chlorophenyl-[2-(3-[1,3]dioxolan-2-yl-propylsulfanyl)-3-methyl-3H-imidazol-4-yl]-methanone). M calc=366; M+H found=367. The dioxolane of the intermediate was then removed under the standard mild conditions of pyridinium p-toluenesulfonate (PPTS). Subsequent reductive amination conditions as described in Example XV using piperidine as the basic component provided the compound of formula (I) wherein:

M is —C(=O)R$^M$; R$^M$ is p-chlorophenyl; A$^3$ is sulfur; L$^3$ is n butyl; Q$^3$ is 1-piperidyl; and Q$^1$ is methyl; also known as (4-Chlorophenyl)-[3-methyl-2-(4-piperidin-1-yl-butylsulfanyl)-3H-imidazol-4-yl]-methanone; M calc=391; M+H found=392; $^1$H NMR (400 MHz, CD$_3$OD): δ7.81 (d, J=8.4 Hz, 2H), 7.53 (d, J=8.4 Hz, 3H), 7.54 (s,1H), 3.90 (s, 3H), 3.31-3.25 (m, 2H), 2.66-2.50 (m, 4H), 2.48-2.44 (m, 2H), 1.80-1.68 (m, 4H), 1.68-1.58 (m, 4H), 1.54-1.44 (m, 2H).

Example XII

Preparation of [3-Methyl-2-(3-piperidin-1-yl-propoxy)-3H-imidazol-4-yl]-naphthalen-1-yl-methanone

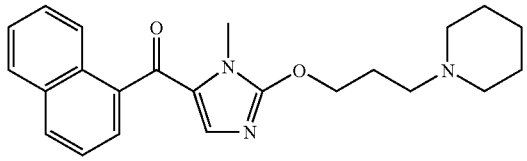

This example teaches the preparation of a compound of formula (I) following Scheme X, wherein M is —C(=O)R$^M$; R$^M$ is 1-naphthalenyl; A$^3$ is oxygen; L$^3$ is propyl; Q$^3$ is 1-piperidyl; and Q$^1$ is methyl.

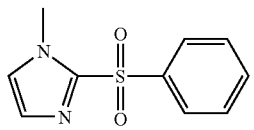

Step A: Preparation of 2-Benzenesulfonyl-1-methyl-1H-imidazole. To a stirred solution of 1-methyl-2-phenylsulfanyl-1H-imidazole (the product of Step A in Example XI) (3.00 g) in Et$_2$O (150 mL) at rt was added 3-chloroperoxybenzoic acid (57%, 22.7 g). The reaction solution was stirred for 18 h at rt and Et$_2$O (750 mL) was added. The organic layer was washed with satd. NaHCO$_3$ (3×200 mL), water (200 mL), and brine (200 mL) and was dried over MgSO$_4$. The solvent was removed in vacuo and the residue was purified by flash chromatography on silica gel (hexanes/acetone) to give the title compound (2.21 g).

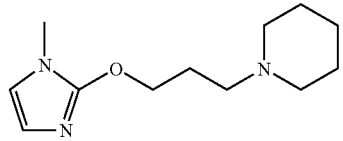

Step B: Preparation of 1-[3-(1-Methyl-1H-imidazol-2-yloxy)-propyl]-piperidine. To a stirred solution of 3-piperidin-1-yl-propan-1-ol (3.19 g) in dry THF (50.0 mL) at rt was added NaH (60% dispersion in mineral oil, 800 mg). The reaction mixture was stirred for 30 min at rt and a solution of the product of Example XII, Step A (990 mg) in dry THF (20.0 mL) was added. The reaction mixture was heated at reflux for 20 h and was allowed to cool to rt. Water (10.0 mL) was added and the solvent was removed in vacuo. The residue was dissolved in CH$_2$Cl$_2$ (400 mL) and the organic layer was washed with water (2×100 mL). The organic layer was dried over MgSO$_4$ and the solvent was removed in vacuo. The residue was purified by flash chromatography on silica gel (CHCl$_3$/NH$_3$, 2 M in MeOH) to give 778 mg of the compound of formula (I) wherein M is hydrogen; A$^3$ is oxygen; L$^3$ is n-propyl; Q$^3$ is 1-piperidyl; and Q$^1$ is methyl; also known as 1-[3-(1-Methyl-1H-imidazol-2-yloxy)-propyl]-piperidine. M calc=223; M+H found=224.

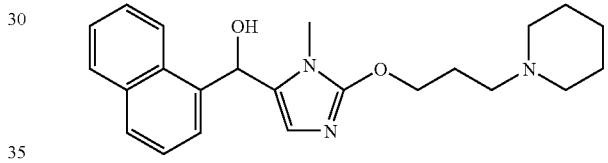

Step C: Preparation of [3-Methyl-2-(3-piperidin-1-yl-propoxy)-3H-imidazol-4-yl]-naphthalen-1-yl-methanol. To a stirred solution of 2,2,6,6-tetramethylpiperidine (140 mg) in dry THF (5.00 mL) and 1,2-dimethoxyethane (DME, 2.50 mL) at −78° C. was added n-BuLi (467 μL, 1.92 M in hexanes). The solution was stirred for 15 min at −78° C. and a solution of the product of Example XII, Step B (100 mg) in dry THF (1.00 mL) was added at −78° C. The reaction mixture was stirred for 45 min at −78° C. and a solution of 1-naphthaldehyde (106 mg) in dry THF (1.00 mL) was added at −78° C. The reaction mixture was allowed to warm to rt and was stirred for 18 h at rt. Water (1.00 mL) was added and the solvent was removed in vacuo. The residue was dissolved in CH$_2$Cl$_2$ (20.0 mL) and the organic layer was washed with water utilizing a Varian chem elute 1005 cartridge. The organic layer was dried over MgSO$_4$ and the solvent was removed in vacuo. The residue was purified by flash chromatography on silica gel (CHCl$_3$/NH$_3$, 2 M in MeOH) to give the material (35.0 mg) containing the title compound, which was used without additional purification.

Step D: Preparation of [3-Methyl-2-(3-piperidin-1-yl-propoxy)-3H-imidazol-4-yl]-naphthalen-1-yl-methanone. To a stirred solution of the product of Example XII, Step C (35.0 mg) in dry CH$_2$Cl$_2$ (5.00 mL) at rt was added MnO$_2$ (85%, activated, 47.0 mg). The reaction mixture was stirred for 18 h at rt and was filtrated over diatomaceous earth. The solvent was removed in vacuo and the residue was purified by flash chromatography (CHCl$_3$/NH$_3$, 2 M in MeOH) to give the title compound (8.00 mg). M calc=377, M+H found=378. $^1$H NMR (400 MHz, CD$_3$OD): δ8.09-8.04 (m, 2H), 7.98-7.95

(m, 1H), 7.69-7.67 (m, 1H), 7.57-7.50 (m, 3H), 6.98 (s, 1H), 4.48 (t, J=6.3 Hz, 2H), 3.87 (s, 3H), 2.56-2.45 (m, 6H), 2.09-2.02 (m, 2H), 1.66-1.60 (m, 4H), 1.51-1.48 (m, 2H). The compound demonstrated useful biological activity when assessed with a [$^3$H]—N-methylhistamine binding assay (see Table in Example XXV).

Step E: Additional compounds prepared following Scheme X, and Example XII, Steps A, B. C, and D. The following compounds of formula (I) were prepared following Scheme X and Example XII, Steps A, B, C, and D; and substituting reagents, and adjusting reaction conditions as needed. The compounds were found to have useful biological activity based on the $K_i$ (nM) value from a [$^3$H]-N-methylhistamine binding assay.

The compounds of formula (I), wherein:

M is —C(=O)$R^M$; $R^M$ is methyl; $A^3$ is oxygen; $L^3$ is propyl; $Q^3$ is 1-piperidyl; and $Q^1$ is methyl; also known as 1-[3-Methyl-2-(3-piperidin-1-yl-propoxy)-3H-imidazol-4-yl]-ethanone; M calc=265; M+H found=266;

M is —CHOH$R^M$; $R^M$ is methyl; $A^3$ is oxygen; $L^3$ is propyl; $Q^3$ is 1-piperidyl; and $Q^1$ is methyl; also known as 1-[3-Methyl-2-(3-piperidin-1-yl-propoxy)-3H-imidazol-4-yl]-ethanol; M calc=267; M+H found=268; $^1$H NMR (400 MHz, CDCl$_3$): δ6.47 (s, 1H), 4.73 (m, 1H), 4.34 (m, 2H), 3.43 (s, 3H), 2.48-2.36 (m, 6H), 2.02-1.94 (m, 2H), 1.63-1.54 (m, 7H), 1.47-1.41 (m, 2H);

M is —C(=O)$R^M$; $R^M$ is 4-methoxyphenyl; $A^3$ is oxygen; $L^3$ is n-propyl; $Q^3$ is 1-piperidyl; and $Q^1$ is methyl; also known as (4-Methoxyphenyl)-[3-methyl-2-(3-piperidin-1-yl-propoxy)-3H-imidazol-4-yl]-methanone; M calc=357; M+H found=358;

M is —C(=O)$R^M$; $R^M$ is 4-pyridyl; $A^3$ is oxygen; $L^3$ is n-propyl; $Q^3$ is 1-piperidyl; and $Q^1$ is methyl; also known as [3-Methyl-2-(3-piperidin-1-yl-propoxy)-3H-imidazol-4-yl]-pyridin-4-yl-methanone; M calc=328; M+H found=329;

M is —C(=O)$R^M$; $R^M$ is 3-pyridyl; $A^3$ is oxygen; $L^3$ is n-propyl; $Q^3$ is 1-piperidyl; and $Q^1$ is methyl; also known as [3-Methyl-2-(3-piperidin-1-yl-propoxy)-3H-imidazol-4-yl]-pyridin-3-yl-methanone; M calc=328; M+H found=329;

M is —C(=O)$R^M$; $R^M$ is 2-pyridyl; $A^3$ is oxygen; $L^3$ is n-propyl; $Q^3$ is 1-piperidyl; and $Q^1$ is methyl; also known as [3-Methyl-2-(3-piperidin-1-yl-propoxy)-3H-imidazol-4-yl]-pyridin-2-yl-methanone; M calc=328; M+H found=329; $^1$H NMR (400 MHz, CD$_3$OD): δ8.69-8.68 (m, 1H), 8.02-7.97 (m, 3H), 7.62-7.56 (m, 1H), 4.50 (t, J=6.2 Hz, 2H), 3.79 (s, 3H), 2.60-2.48 (m, 6H), 2.12-2.04 (m, 2H), 1.67-1.61 (m, 4H), 1.54-1.46 (m, 2H);

M is —C(=O)$R^M$; $R^M$ is cyclohexyl; $A^3$ is oxygen; $L^3$ is n-propyl; $Q^3$ is 1-piperidyl; and $Q^1$ is methyl; also known as Cyclohexyl-[3-methyl-2-(3-piperidin-1-yl-propoxy)-3H-imidazol-4-yl]-methanone; M calc=333; M+H found=334;

M is —C(=O)$R^M$; $R^M$ is 4-biphenyl; $A^3$ is oxygen; $L^3$ is n-propyl; $Q^3$ is 1-piperidyl; and $Q^1$ is methyl; also known as Biphenyl-4-yl-[3-methyl-2-(3-piperidin-1-yl-propoxy)-3H-imidazol-4-yl]-methanone; M calc=403; M+H found=404; $^1$H NMR (400 MHz, CD$_3$OD): δ7.90-7.86 (m, 2H), 7.80-7.77 (m, 2H), 7.72-7.70 (m, 2H), 7.53-7.47 (m, 2H), 7.42-7.38 (m, 1H), 7.31 (s, 1H), 4.50 (t, J=6.2 Hz, 2H), 3.77 (s, 3H), 2.59-2.48 (m, 6H), 2.11-2.05 (m, 2H), 1.67-1.61 (m, 4H), 1.54-1.48 (m, 2H);

M is —C(=O)$R^M$; $R^M$ is hydrogen; $A^3$ is oxygen; $L^3$ is n-propyl; $Q^3$ is 1-piperidyl; and $Q^1$ is methyl; also known as 3-Methyl-2-(3-piperidin-1-yl-propoxy)-3H-imidazol-4-yl-carbaldehyde; M calc=251; M+H found=252;

M is —CHOH$R^M$; $R^M$ is 3,5-dichlorophenyl; $A^3$ is oxygen; $L^3$ is methyl; $Q^3$ is 4-(1-isopropylpiperidyl); and $Q^1$ is methyl; also known as (3,5-Dichlorophenyl)-[2-(1-isopropyl-piperidin-4-ylmethoxy)-3-methyl-3H-imidazol-4-yl]-methanol; M calc=411; M+H found=412;

M is —CHOH$R^M$; $R^M$ is 4-cyanophenyl; $A^3$ is oxygen; $L^3$ is methyl; $Q^3$ is 4-(1-isopropylpiperidyl); and $Q^1$ is methyl; also known as 4-{(Hydroxy-[2-(1-isopropyl-piperidin-4-ylmethoxy)-3-methyl-3H-imidazol-4-yl]-methyl}-benzonitrile; $^1$H NMR (400 MHz, CDCl$_3$): δ7.57 (d), 7.48 (d), 6.20 (s), 5.72 (s), 3.13 (s), 0.96 (d);

M is —C(=O)$R^M$; $R^M$ is 3,5-dichlorophenyl; $A^3$ is oxygen; $L^3$ is methyl; $Q^3$ is 4-(1-isopropylpiperidyl); and $Q^1$ is methyl; also known as (3,5-Dichlorophenyl)-[2-(1-isopropyl-piperidin-4-ylmethoxy)-3-methyl-3H-imidazol-4-yl]-methanone; M calc=409; M+H found=410; $^1$H NMR (400 MHz, CDCl$_3$): δ7.65 (d, J=1.9 Hz, 2H), 7.54 (t, J=1.9 Hz, 1H), 7.25 (s, 1H), 4.33 (d, J=6.2 Hz, 2H), 3.76 (s, 3H), 3.00-2.85 (m, 2H), 2.80-2.69 (m, 1H), 2.22-2.21 (m, 2H), 1.92-1.83 (m, 2H), 1.49-1.39 (m, 2H), 1.07 (d, J=6.6 Hz, 6H).

M is —C(=O)$R^M$; $R^M$ is 2-chlorophenyl; $A^3$ is oxygen; $L^3$ is methyl; $Q^3$ is 4-(1-isopropylpiperidyl); and $Q^1$ is methyl; also known as (2-Chlorophenyl)-[2-(1-isopropyl-piperidin-4-ylmethoxy)-3-methyl-3H-imidazol-4-yl]-methanone; M calc=375; M+H found=376; $^1$H NMR (400 MHz, CDCl$_3$): δ7.40-7.29 (m, 2H), 7.28-7.22 (m, 2H), 6.89 (s, 1H), 4.24 (d, J=6.2 Hz, 2H), 3.75 (s, 3H), 2.91 (br d, J=11.3 Hz, 2H), 2.75-2.70 (m, 1H), 2.24-2.09 (m, 2H), 1.78 (br d, J=10.9 Hz, 2H), 1.47-1.38 (m, 2H), 1.03 (d, J=7.6 Hz, 6H);

M is —C(=O)$R^M$; $R^M$ is 4-cyanophenyl; $A^3$ is oxygen; $L^3$ is methyl; $Q^3$ is 4-(1-isopropylpiperidyl); and $Q^1$ is methyl; also known as 4-[2-(1-Isopropyl-piperidin-4-ylmethoxy)-3-methyl-3H-imidazole-4-carbonyl]-benzonitrile; M calc=366; M+H found=367; $^1$H NMR (400 MHz, CDCl$_3$): δ7.81-7.75 (dm, J=8.2 Hz, 2H), 7.72-7.68 (dm, J=11.1Hz, 2H), 7.12 (s, 1H), 4.25 (d, J=6.2 Hz, 2H), 3.70 (s, 3H), 2.87 (d, J=11.4 Hz, 2H), 2.73-2.60 (m, 1H), 2.11 (t, J=11.7 Hz, 2H), 1.85-1.72 (m, 3H), 1.44-1.27 (m, 2H), 0.98 (d, J=8.8 Hz, 6H);

M is —C(=O)$R^M$; $R^M$ is 3-chlorophenyl; $A^3$ is oxygen; $L^3$ is methyl; $Q^3$ is 4-(1-isopropylpiperidyl); and $Q^1$ is methyl; also known as (3-Chlorophenyl)-[2-(1-isopropyl-piperidin-4-ylmethoxy)-3-methyl-3H-imidazol-4-yl]-methanone; M calc=375; M+H found=376; $^1$H NMR (400 MHz, CDCl$_3$): δ7.69 (t, J=1.7 Hz, 1H), 7.61-7.51 (dm, J=7.6 Hz, 1H), 7.48-7.44 (m, 1H), 7.34 (t, J=7.9 Hz, 1H), 7.16 (s, 1H), 4.25 (d, J=6.2 Hz, 2H), 3.69 (s, 3H), 2.94-2.83 (m, 2H), 2.74-2.64 (m, 1H), 2.18-2.07 (m, 1H), 1.84-1.72 (m, 2H), 1.70-1.32 (m, 4H), 1.00 (d, J=6.5 Hz, 6H);

M is —C(=O)$R^M$; $R^M$ is 4-trifluoromethylphenyl; $A^3$ is oxygen; $L^3$ is methyl; $Q^3$ is 4-(1-isopropylpiperidyl); and $Q^1$ is methyl; also known as [2-(1-Isopropyl-piperidin-4-ylmethoxy)-3-methyl-3H-imidazol-4-yl]-(4-trifluoromethyl-phenyl)-methanone; M calc=409; M+H found=410; $^1$H NMR (400 MHz, CDCl$_3$): δ7.83-7.77 (dm, J=8.0 Hz, 2H), 7.74 (d, J=7.6 Hz, 2H), 7.22 (s, 1H), 4.33 (d, J=6.3 Hz, 2H), 3.72 (s, 3H), 2.98-2.82 (m, 2H), 2.85-2.66 (m, 1H), 2.25-2.14 (m, 2H), 1.90-1.73 (m, 2H), 1.56-1.41 (m, 2H), 1.07 (d, J=6.6 Hz, 6H);

M is —C(=O)$R^M$; $R^M$ is 4-nitrophenyl; $A^3$ is oxygen; $L^3$ is methyl; $Q^3$ is 4-(1-isopropylpiperidyl); and $Q^1$ is methyl; also known as [2-(1-Isopropyl-piperidin-4-yl-methoxy)-3-methyl-3H-imidazol-4-yl]-(4-nitro-phenyl)-methanone; M calc=386; M+H found=387; $^1$H NMR (400 MHz, CDCl$_3$): δ8.27-8.23 (dm, J=8.7 Hz, 2H), 7.88-7.81 (dm, J=8.7 Hz, 2H), 7.14 (s, 1H), 4.26 (d, J=6.2 Hz, 2H), 3.72 (s, 3H),.2.91-2.81 (d, J=11.5 Hz, 2H), 2.15-2.05 (m, 2H), 1.84-1.72 (m, 3H), 1.43-1.27 (m, 2H), 0.99 (d, J=6.6 Hz, 6H);

M is —C(=O)R$^M$; R$^M$ is 4-fluorophenyl; A$^3$ is oxygen; L$^3$ is methyl; Q$^3$ is 4-(1-isopropylpiperidyl); and Q$^1$ is methyl; also known as (4-Fluorophenyl)-[2-(1-isopropyl-piperidin-4-ylmethoxy)-3-methyl-3H-imidazol-4-yl]-methanone; M calc=359; M+H found=360; $^1$H NMR (400 MHz, CDCl$_3$): δ7.78-7.69 (m, 2H), 7.12 (s, 1H), 7.11-7.03 (m, 2H), 4.24 (d, J=6.6 Hz, 2H), 3.69 (s, 3H), 2.93-2.82 (m, 2H), 2.74-2.61 (m, 1H), 2.11 (t, J=11.4 Hz, 2H), 1.77 (d, J=12.6 Hz, 2H), 1.46-1.29 (m, 2H), 1.23-1.12 (m, 1H), 0.99 (d, J=6.4 Hz, 6H); and M is —C(=O)R$^M$; R$^M$ is 4-isopropylphenyl; A$^3$ is oxygen; L$^3$ is methyl; Q$^3$ is 4-(1-isopropylpiperidyl); and Q$^1$ is methyl; also known as (4-Isopropylphenyl)-[2-(1-isopropyl-piperidin-4-ylmethoxy)-3-methyl-3H-imidazol-4-yl]-methanone; M calc=383; M+H found=384; $^1$H NMR (400 MHz, CDCl$_3$): δ7.70-7.55 (m, 2H), 7.27-7.22 (m, 2H), 7.17 (s, 1H), 4.28-4.15 (m, 2H), 3.69 (s, 3H), 2.98-2.82 (m, 2H), 2.81-2.65 (m, 1H), 2.25-2.05 (m, 3H), 1.85-1.25 (m, 5H), 1.23-1.10 (m, 6H), 1.03 (dm, J=6.2 Hz, 6H).

Example XIII

Preparation of {3-[5-(4-Chlorobenzyl)-1-methyl-1H-imidazol-2-ylsulfanyl]-propyl}-dimethyl-amine

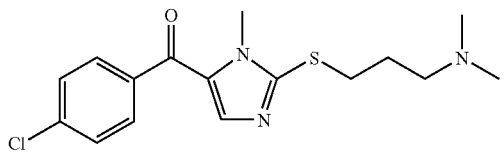

This example teaches the preparation of a compound of formula (I) following Scheme VII, wherein M is —CH$_2$R$^M$; R$^M$ is p-chlorophenyl; A$^3$ is sulfur; L$^3$ is n-propyl; Q$^3$ is dimethylamino; and Q$^1$ is methyl.

The product from Example II, Step C (0.04 g) in n-butanol (1 mL) was treated with potassium t-butoxide (0.03 g), followed by hydrazine (0.011 mL). After heating to 120° C. for 16 h, the mixture was cooled to rt and partitioned between brine (75 mL) and EtOAc (100 mL). The layers were separated and the organic portion was washed with brine (100 mL), dried over Na$_2$SO$_4$, and concentrated to give the crude product. The crude material was purified by silica gel chromatography (1-5% MeOH/CH$_2$Cl$_2$ to provide the title compound (0.017 g, 45%). M calc=323; M+H found 324; $^1$H NMR (400 MHz, CDCl$_3$): δ7.19 (d, J=8.3 Hz, 2H), 7.01 (d, J=8.3 Hz, 2H), 6.78 (s, 1H), 3.81 (s, 2H), 3.29 (s, 3H), 2.98 (t, J=7.3 Hz, 2H), 2.29 (t, J=7.0 Hz, 2H), 2.12 (s, 6H), 1.74 (m, 2H). The compound demonstrated useful biological activity when assessed with a [$^3$H]—N-methylhistamine binding assay (see Table in Example XXV).

Example XIV

Preparation of (4-Chlorophenyl)-[2-(3-dimethylamino-propylsulfanyl)-3-methyl-3H-imidazol-4-yl]-methanone oxime

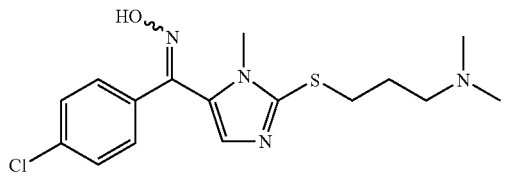

This example teaches the preparation of a compound of formula (I) following Scheme VIII, wherein M is —C(=N—OH)R$^M$; R$^M$ is p-chlorophenyl; A$^3$ is sulfur; L$^3$ is n-propyl; Q$^3$ is dimethylamino; and Q$^1$ is methyl.

The product from Example II, Step C (0.07 g) in EtOH (2 mL) was treated with hydroxylamine hydrochloride (0.07 g) followed by pyridine (0.08 mL). After stirring for 16 h at 80° C., the solvent was removed under reduced pressure. The residue was then partitioned between water (75 mL) and EtOAc (100 mL). The layers were separated and the organic portion was washed with brine (100 mL). The aqueous portion was treated with solid NaHCO$_3$ until the solution reached pH=7. The aqueous portion was extracted with EtOAc (4×50 mL) and CH$_2$Cl$_2$ (2×50 mL). The combined organic extracts were dried over Na$_2$SO$_4$, and concentrated to provide the crude product. The crude material was purified by silica gel chromatography (1-5% 2 M NH$_3$ in MeOH/CH$_2$Cl$_2$ to provide the title compound as a mixture of oxime isomers (0.01 g, 14%). M calc=352, M+H found=353; $^1$H NMR (400 MHz, CDCl$_3$): δ7.43-7.37 (m, 1.4H), 7.32-7.28 (m, 1.3H), 7.25-7.20 (m, 1.3H), 6.99 (s, 0.6H), 6.62 (s, 0.4H), 3.66 (s, 1H), 3.26 (s, 2H), 3.12-3.04 (m, 2H), 2.47-2.36 (m, 2H), 2.23 (s, 6H), 1.94-1.82 (m, 2H). The compound demonstrated useful biological activity when assessed with a [$^3$H]—N-methylhistamine binding assay (see Table in Example XXV).

Example XV

Preparation of [3-Methyl-2-(3-piperidin-1-yl-propoxy)-3H-imidazol-4-yl]-piperidin-1-yl-methane

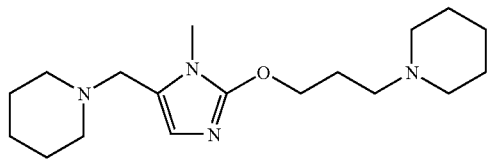

This example teaches the preparation of a compound of formula (I) following Scheme XII, wherein M is —CH$_2$R$^M$; R$^M$ is 1-piperidyl; A$^3$ is oxygen; L$^3$ is n-propyl; Q$^3$ is 1-piperidyl; and Q$^1$ is methyl.

To a stirred solution of 3-methyl-2-(3-piperidin-1-yl-propoxy)-3H-imidazole-4-carbaldehyde (10.0 mg) and piperidine (3.41 mg) in 1,2-dichloroethane at rt was added sodium triacetoxyborohydride (12.7 mg). The reaction mixture was stirred for 18 h at rt and CH$_2$Cl$_2$ (5.00 mL) and satd. NaHCO$_3$ (2.00 mL) were added. The mixture was stirred for 1 h at rt and additional CH$_2$Cl$_2$ (100 mL) was added. The organic layer was washed with satd. NaHCO$_3$ (20.0 mL) and water (2×20.0 mL) and was dried over MgSO$_4$. The solvent was removed in vacuo and the residue was purified by flash chromatography on silica gel (CHCl$_3$/2 M NH$_3$ in MeOH) to give the title compound (1.00 mg). M calc=320; M+H found=321; $^1$H NMR (400 MHz, CD$_3$OD): δ6.42 (s, 1H), 4.30 (t, J=6.2 Hz, 2H), 3.40 (s, 3H), 3.34 (s, 2H), 2.57-2.38 (m, 10H), 2.04-1.96 (m, 2H), 1.67-1.41 (m, 12H). The compound demonstrated useful biological activity when assessed with a [$^3$H]—N-methylhistamine binding assay (see Table in Example XXV).

Example XVI

Preparation of (4-Chloro-phenyl)-[2-(3-dimethylamino-propane-1-sulfinyl)-3-methyl-3H-imidazol-4-yl]-methanone

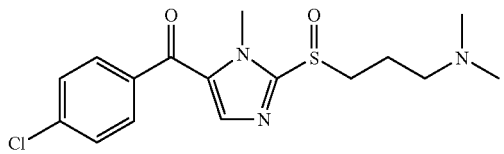

This example teaches the preparation of a compound of formula (I) following Scheme XI, wherein M is —C(=O)R$^M$; R$^M$ is p-chlorophenyl; A$^3$ is S(O); L$^3$ is n-propyl; Q$^3$ is dimethylamino; and Q$^1$ is methyl.

Step A: Preparation of (4-Chloro-phenyl)-[2-(3-dimethylamino-propane-1-sulfinyl)-3-methyl-3H-imidazol-4-yl]-methanone. To a stirred solution of (4-Chloro-phenyl)-[2-(3-dimethylamino-propylsulfanyl)-3-methyl-3H-imidazol-4-yl]-methanone (135 mg) in glacial acetic acid (4.00 mL) was added at rt H$_2$O$_2$ (82.0 μL; 30 wt. % in water). The reaction solution was stirred for 48 h at rt, and water (10.0 mL) was added. The solution was brought to pH=12 using NaOH (25% in water) and extracted with CH$_2$Cl$_2$ (250 mL, 2×50.0 mL). The combined organic layers were washed with water (3×20.0 mL) and were dried over MgSO$_4$. The solvent was removed in vacuo, and the residue was purified by flash chromatography on silica gel (CHCl$_3$/2 M NH$_3$ in MeOH) to give the title compound (121 mg). M calc=353; M+H found=354; $^1$H NMR (400 MHz, CD$_3$OD): δ7.91-7.87 (m, 2H), 7.70 (s, 1H), 7.60-7.55 (m, 2H), 4.21 (s, 3H), 3.61-3.48 (m, 2H), 2.54-2.43 (m, 2H), 2.21 (s, 6H), 2.04-1.94 (m, 2H). The compound demonstrated useful biological activity when assessed with a [$^3$H]—N-methylhistamine binding assay (see Table in Example XXV).

Step B: Additional compounds prepared following Scheme XI, and Example XVI. Step A. The following compounds of formula (I) were prepared following Scheme XI and Example XVI, Step A; and substituting reagents, and adjusting reaction conditions as needed.

The compounds of formula (I), wherein:
M is —C(=O)R$^M$; R$^M$ is p-chlorophenyl; A$^3$ is S(O$_2$); L$^3$ is n-propyl; Q$^3$ is dimethylamino; and Q$^1$ is methyl; also known as (4-Chlorophenyl)-[2-(3dimethylamino-propane-1-sulfonyl)-3-methyl-3H-imidazol-4-yl]-methanone; M calc=369; M+H found=370; K$_i$=10000; and
M is —C(=O)R$^M$; R$^M$ is p-chlorophenyl; A$^3$ is S(O$_2$); L$^3$ is n-propyl; Q$^3$ is dimethylazinoyl; and Q$^1$ is methyl; also known as (4-Chlorophenyl)-[2-(3-dimethylamino-propane-1-sulfonyl)-3-methyl-3H-imidazol-4-yl]-methanone oxide; M calc=385; M+H found=386; K$_i$=10000.

Example XVII

Preparation of (4-Chloro-phenyl)-[2-(1-isopropyl-piperidin-4-ylmethoxy)-3-methyl-3H-imidazol-4-yl]-methanone maleate salt

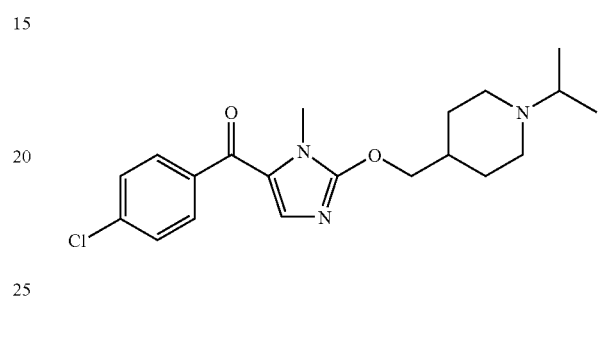

This example teaches the preparation of a compound of formula (I) following Schemes XIIIa-b, and XIV, wherein M is —C(=O)R$^M$; R$^M$ is p-chlorophenyl; A$^3$ is oxygen; L$^3$ is methyl, Q$^3$ is 4-(1-isopropyl-piperidyl); and Q$^1$ is methyl.

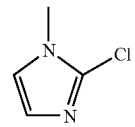

Step A: Preparation of 2-Chloro-1-methyl-1H-imidazole. To a 300-mL, three-necked, round-bottomed flask equipped with a magnetic stirrer, and nitrogen inlet was added N-methylimidazole (4.1 g, 0.05 mol) and anhydrous THF (25 mL). The stirrer was started and the solution was cooled to −78° C. n-BuLi (2.5 M in hexanes, 22 mL, 0.055 mol) was added via syringe resulting in a golden yellow solution. This solution was stirred for 30 min whereupon a solution of hexachloroethane (13 g, 0.055 mol) in THF (25 mL) was slowly added via syringe. The reaction mixture was stirred for 1 h and then was quenched with satd. aq. NH$_4$Cl (25 mL). The cooling bath was removed and when the reaction flask reached rt the contents were transferred to a 500 mL separatory funnel, washing with EtOAc (150 mL). The organic layer was separated, washed with water, brine, and dried over anhydrous Na$_2$SO$_4$. After filtration, the solvents were evaporated under reduced pressure resulting in an oily residue. This crude product was distilled under reduced pressure to afford 2-chloro-1-methyl-1H-imdazole (4.75 g, 80%) as a colorless liquid. bp 54° C./2 Torr. IR (film): 1515, 1420, 1367, 1277,1127, 912, 740, 689, 665 cm$^{-1}$. $^1$H NMR (400 MHz, CDCl$_3$): δ6.92 (d, J=1.5 Hz, 1H), 6.85 (d, J=1.5 Hz, 1H), 3.55 (s, 3H). $^{13}$C NMR (100 MHz, CDCl$_3$): δ132.4, 128.0, 122.3, 33.5. HRMS (EI): m/z calcd for C$_4$H$_6$ClN$_2$ [M+H]$^+$, 117.0223; found, 117.0220.

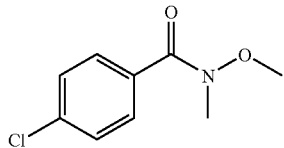

Step B: Preparation of 4-Chloro-N-methoxy-N-methyl-benzamide. A 1-L, three-necked, round-bottomed flask equipped with a magnetic stirrer, nitrogen inlet and an addition funnel was charged with N,O-dimethylhydroxylamine hydrochloride (20 g, 0.20 mol) and CH$_2$Cl$_2$ (250 mL). The mixture was cooled to 0° C. and triethylamine (24 g, 0.20 mol) was added, followed by a solution of 4-chlorobenzoyl chloride (35.8 g, 0.2 mol) in CH$_2$Cl$_2$ (100 mL). After the addition was complete, the cooling bath was removed, and the reaction was allowed to warm to rt and was stirred overnight. The reaction mixture was quenched with satd. aq. NH$_4$Cl (200 mL). The mixture was transferred to a separatory funnel, the layers were separated and the aqueous layer was extracted with CH$_2$Cl$_2$ (200 mL). The combined organic layers were washed with aq. NaHCO$_3$, brine, and then dried over anhydrous MgSO$_4$. After filtration, the solvents were evaporated under reduced pressure to afford the benzamide (37 g, 92%) as a colorless oil. IR (film): 2935, 1639, 1593, 1460, 1415, 1212, 1090, 1015, 887, 838, 747, 730 cm$^{-1}$. $^1$H NMR (400 MHz, CDCl$_3$): δ7.58 (d, J=8.6 Hz, 2H), 7.32 (d, J=8.6 Hz, 2H), 3.55 (s, 3H), 3.11 (s, 3H). $^{13}$C NMR (100 MHz, CDCl$_3$): δ169.2, 137.3, 132.9, 130.5, 128.8, 61.7, 34.1. HRMS (EI): m/z calcd for C$_9$H$_{11}$ClNO$_2$ [M+H]$^+$, 200.0478; found, 200.0484.

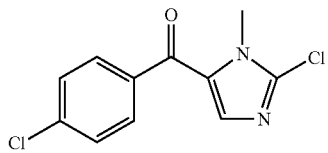

Step C: (2-Chloro-3-methyl-3H-imidazol-4-yl)-(4-chlorophenyl)-methanone. To a 1-L, three-necked, round-bottomed flask equipped with a magnetic stirrer, nitrogen inlet and an addition funnel was added 2-chloro-1-methyl-1H-imidazole (15 g, 0.128 mol) and THF (250 mL). The reaction mixture was cooled to −78° C. and n-BuLi (2.5 M in hexanes, 54 mL, 0.135 mol) was added. The pale yellow suspension that formed was stirred for 1 h and a solution of 4-chloro-N-methoxy-N-methyl-benzamide (27 g, 0.135 mol) in THF (50 mL) was then added dropwise. After the addition was complete, the cooling bath was removed and the reaction was allowed to warm to rt. The reaction mixture was quenched with satd. aq. NH$_4$Cl (150 mL), transferred to a separatory funnel, and extracted with EtOAc (1.5 L). The organic layer was washed with water, brine and dried over anhydrous Na$_2$SO$_4$. After filtration, the solvents were evaporated under reduced pressure to yield the product as a crystalline solid. Recrystallization from EtOAc-hexanes afforded the desired ketone (31.2 g, 97%) as a white crystalline solid. mp 173-174° C. IR (film): 1639, 1589, 1517, 1395, 1377, 1253, 1186, 902, 841, 756, 738, 695, 676 cm$^{-1}$. $^1$H NMR (400 MHz, CDCl$_3$): δ7.78 (d, J=8.6 Hz, 2H), 7.44 (s, 1H), 7.44 (d, J=8.6 Hz, 2H), 3.97 (s, 3H). $^{13}$C NMR (100 MHz, CDCl$_3$): δ183.3, 140.3, 139.5, 139.2, 136.3, 131.2, 130.4, 128.9, 33.5. HRMS (EI): m/z calcd for C$_{11}$H$_9$Cl$_2$N$_2$O [M+H]$^+$, 255.0092; found, 255.0104. Anal. Calcd for C$_{11}$H$_8$Cl$_2$N$_2$O: C, 51.8; H, 3.06; N, 10.93. Found: C, 52.08; H, 3.16; N, 10.90.

This step is alternatively performed using 4-chlorobenzoyl chloride-in place of 4-chloro-N-methoxy-N-methyl-benzamide.

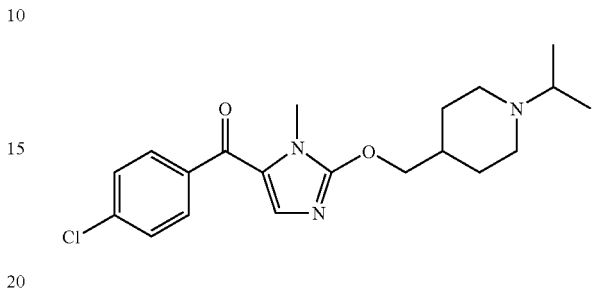

Step D: (4-Chloro-phenyl)-[2-(1-isopropyl-piperidin-4-ylmethoxy)-3-methyl-3H-imidazol-4-yl]-methanone. To a 1-L, three-necked, round-bottomed flask equipped with a magnetic stirrer, nitrogen inlet and an addition funnel was added NaH (1.45 g, 0.061 mol) and THF (300 mL). The stirred suspension was cooled to 0° C. and (1-isopropyl-piperidin-4-yl)-methanol (9.5 g, 0.06 mol) was added. The cooling bath was removed, and the reaction warmed to rt. After 2 h, a solution of (2-chloro-3-methyl-3H-imidazol-4-yl)-(4-chloro-phenyl)-methanone (15.56 g, 0.061 mol) in dry THF (100 mL) was added. The reaction mixture was stirred at 60° C. and monitored by HPLC every 4-8 h. After 36 h, the reaction was judged complete. The reaction mixture was cooled to rt, poured into ice-cold water, and extracted with EtOAc (2×250 mL). The combined organic extracts were dried over anhydrous Na$_2$SO$_4$, filtered, and evaporated under reduced pressure to provide the crude material as a brown solid. Recrystallization from EtOAc afforded the desired product (17.5 g, 78%) as a white crystalline solid. mp 126-127° C. IR (film): 2963, 1615, 1585, 1529, 1481, 1362, 1287, 1213, 1173, 1104, 1020, 897, 846, 727, 698 cm$^{-1}$. $^1$H NMR (400 MHz, CDCl$_3$): δ7.67 (d, J=8.6 Hz, 2H), 7.38 (d, J=8.6 Hz, 2H), 7.13 (s, 1H), 4.22 (d, J=6.0 Hz, 2H), 3.68 (s, 3H), 2.84 (m, 2H), 2.61 (m, 1H), 2.09 (m, 2H), 1.74 (m, 3H), 1.30 (m, 2H), 0.97 (d, J=6.5 Hz, 6H). $^{13}$C NMR (100 MHz, CDCl$_3$): δ183.4, 157.0, 138.3, 138.2, 137.3, 130.2, 128.7, 127.1, 74.9, 54.6, 48.4, 35.9, 30.7, 29.1, 18.3. HRMS (EI): m/z calcd for C$_{20}$H$_{27}$ClN$_3$O$_2$ [M+H]$^+$, 376.1792; found, 376.1801. Anal. Calcd for C$_{20}$H$_{26}$ClN$_3$O$_2$: C, 63.91; H, 6.97; N, 11.17. Found: C, 63.55; H, 6.77; N, 11.05.

Step E: (4-Chloro-phenyl)-[2-(1-isopropyl-piperidin-4-ylmethoxy)-3-methyl-3H-imidazol-4-yl]-methanone maleate salt. A 500-mL, 3-necked, round-bottomed flask equipped with a magnetic stirrer, nitrogen inlet, reflux condenser and an addition funnel was charged with (4-chloro-phenyl)-[2-(1-isopropyl-piperidin-4-ylmethoxy)-3-methyl-3H-imidazol-4-yl]-methanone (15.4 g, 40.96 mol), EtOH (170 mL), and maleic acid (4.75 g, 40.96 mol). The mixture was heated on a heating mantle at 70-75° C. until a clear solution was obtained. The heat source was removed and the reaction mixture was cooled to rt. The solution was transferred to a 2-L beaker, washing with 25 mL of EtOH. The solution was diluted with 750 mL of Et$_2$O with vigorous stirring. The white precipitate that formed was filtered and dried in vacuo to afford the maleate salt as a white powder. Recrystallization from water afforded the maleate salt (18.8 g, 93%) as colorless needles. mp 161-162° C. IR (film): 2963, 1625, 1586, 1532, 1466, 1361, 1257, 1172, 1087, 1025, 956, 757, 698 cm$^{-1}$. $^1$H NMR (400 MHz, CDCl$_3$): δ7.71 (d, J=8.6 Hz, 2H), 7.43 (d, J=8.6 Hz, 2H), 7.17 (s, 1H), 6.27 (s, 2H), 4.36 (d, J=6.0 Hz, 2H), 3.73 (s, 3H), 3.53 (m, 3H), 2.74 (bt, J=11.6 Hz, 2H), 2.24-1.92 (m, 5H), 1.34 (d, J=6.8 Hz, 6H). $^{13}$C NMR (100 MHz, CDCl$_3$): δ183.9, 169.7, 156.6, 138.8, 138.2, 137.5, 136.0, 130.6, 129.1, 127.7, 73.2, 57.9, 48.3, 34.4, 31.1, 26.0, 17.0. Anal. Calcd for C$_{24}$H30ClN$_3$O$_6$: C, 58.21; H, 6.07; N, 8.35. Found: C, 58.6; H, 6.07; N, 8.35.

Example XVIII

Preparation of (4-Chloro-phenyl)-{2-[(1-isopropyl-piperidin-4-ylmethyl)-amino]-3-methyl-3H-imidazol-4-yl}-methanone

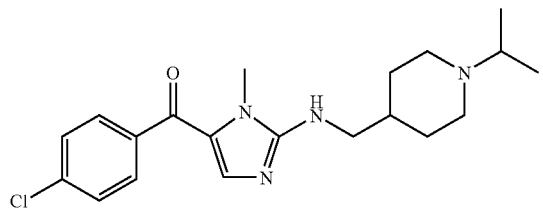

This example teaches the preparation of a compound of formula (I) following Schemes XIIIa-b and XIV, wherein M is —C(=O)R$^M$; R$^M$ is p-chlorophenyl; A$^3$ is NH; L$^3$ is methyl, Q$^3$ is 4-(1-isopropyl-piperidyl); and Q$^1$ is methyl.

To a solution of (2-chloro-3-methyl-3H-imidazol-4-yl)-(4-chloro-phenyl)-methanone (1 equivalent) in THF (0.2 M) is added C-(1-isopropyl-piperidin-4-yl)-methylamine (1.5 equivalents) and diisopropylethylamine (1.5 equivalents). The mixture is heated at reflux until HPLC analysis shows consumption of the starting material. The reaction mixture is cooled to rt, quenched with satd. aq. NH$_4$Cl, and extracted with EtOAc (2×). The combined organic extracts are washed with water and brine, dried over anhydrous Na$_2$SO$_4$, filtered and concentrated. The crude material is purified by chromatography or recrystallization to provide the desired product.

Example XIX

Alternative Preparation of (4-Bromophenyl)-[3-methyl-2-(3-piperidin-1-yl-propylsulfanyl)-3H-imidazol-4-yl methanone

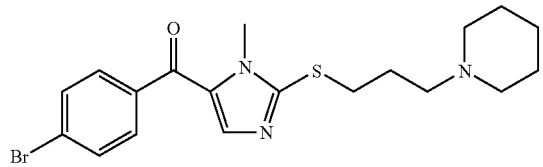

This example demonstrates the preparation of a compound of formula (I) following Schemes XIIIa-b and XIV, wherein M is —C(=O)R$^M$; R$^M$ is p-bromophenyl; A$^3$ is-sulfur; L$^3$ is n-propyl; Q$^3$ is 1-piperidyl; and Q$^1$ is methyl.

To a 0° C. solution of 3-piperidin-1-yl-propane-1-thiol (1.5 equivalents) in THF (0.2 M) is added NaH (60% dispersion in oil, 1.5 equivalents). After 30 min, (2-chloro-3-methyl-3H-imidazol-4-yl)-(4-chloro-phenyl)-methanone (1 equivalent) in THF (1 M) is added dropwise. The mixture is heated at reflux until HPLC analysis shows consumption of the starting material. The reaction mixture is cooled to rt, quenched with satd. aq. NH$_4$Cl, and extracted with EtOAc (2×). The combined organic extracts are washed with water and brine, dried over anhydrous Na$_2$SO$_4$, filtered and concentrated. The crude material is purified by chromatography or recrystallization to provide the desired product. This material can then be oxidized to form the corresponding sulfoxide (A$^3$ is S(O)), or sulfone (A$^3$ is S(O$_2$)) as described in Example XVI, Scheme XI.

Example XX

Preparation of (3-Fluoro-phenyl)-[3-methyl-2-(3-piperidin-1-yl-propylamino)-3H-imidazol-4-yl]-methanol

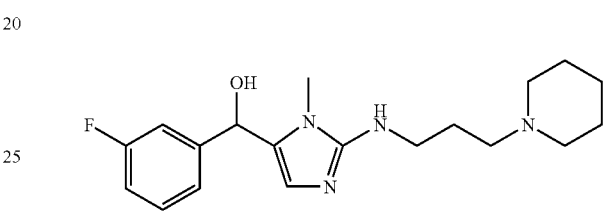

This example demonstrates the preparation of a compound of formula (I) following Scheme XV, wherein M is —CHOHR$^M$; R$^M$ is m-fluorophenyl; A$^3$ is NH; L$^3$ is n-propyl; Q$^3$ is 1-piperidyl; and Q$^1$ is methyl.

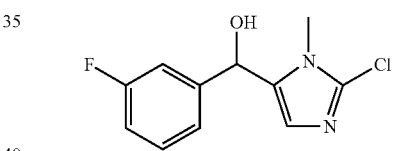

Step A: (3-Fluoro-phenyl)-(2-chloro-3-methyl-3H-imidazol-4-yl)-methanol. To a 1-L, three-necked, round-bottomed flask equipped with a magnetic stirrer, nitrogen inlet and an addition funnel is added 2-chloro-1-methyl-1H-imidazole (1 equiv.) and THF (0.5 M). The reaction mixture is cooled to −78° C. and n-BuLi (2.5 M in hexanes, 1.05 equiv.) is added. The resulting mixture is stirred for 1 h and a solution of 3-fluorobenzaldehyde (1.05 eq) in THF (2.5 M) is then added dropwise. After the addition is complete, the cooling bath is removed and the reaction is allowed to warm to rt. The reaction mixture is quenched with satd. aq. NH$_4$Cl, transferred to a separatory funnel, and extracted with EtOAc. The organic layer is washed with water, brine and dried over anhydrous Na$_2$SO$_4$. After filtration, the solvents are evaporated under reduced pressure to yield the product. The material is purified by recrystallization or column chromatography.

Step B: (3-Fluoro-phenyl)-[3-methyl-2-(3-piperidin-1-yl-propylamino)-3H-imidazol-4-yl]-methanol. To a solution of (3-fluoro-phenyl)-(2-chloro-3-methyl-3H-imidazol-4-yl)-methanol (1 equivalent) in THF (0.2 M) is added 3-piperidin-1-ylpropylamine (1.5 equivalents) and diisopropylethylamine (1.5 equivalents). The mixture is heated at reflux until HPLC analysis shows consumption of the starting material. The reaction mixture is cooled to rt, quenched with satd. aq. NH$_4$Cl, and extracted with EtOAc (2×). The combined organic extracts are washed with water and brine, dried over anhydrous Na$_2$SO$_4$, filtered and concentrated. The crude material is purified by chromatography or recrystallization to provide the desired product.

Alternative Embodiment

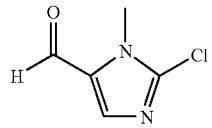

Step A': 2-Chloro-3-methyl-3H-imidazole-4-carbaldehyde. To a 1-L, three-necked, round-bottomed flask equipped with a magnetic stirrer, nitrogen inlet and an addition funnel is added 2-chloro-1-methyl-1H-imidazole (1 equiv.) and THF (0.5 M). The reaction mixture is cooled to –78° C. and n-BuLi (2.5 M in hexanes, 1.05 equiv.) is added. The resulting mixture is stirred for 1 h and a solution of DMF (1.05 eq) in THF (2.5 M) is then added dropwise. After the addition is complete, the cooling bath is removed and the reaction is allowed to warm to rt. The reaction mixture is quenched with satd. aq. NH$_4$Cl, transferred to a separatory funnel, and extracted with EtOAc. The organic layer is washed with water, brine and dried over anhydrous Na$_2$SO$_4$. After filtration, the solvents are evaporated under reduced pressure to yield the product. The material is purified by recrystallization or column chromatography.

Step B': (3-Fluoro-phenyl)-(2-chloro-3-methyl-3H-imidazol-4-yl)-methanol. To a –78° C. solution of 1-bromo-3-fluorobenzene (1 equiv.) in THF (0.2 M) was added n-BuLi (2.5 M in hexanes, 1.05 equiv.) is added. The resulting mixture is stirred for 1 h and a solution of 2-chloro-3-methyl-3H-imidazole-4-carbaldehyde (1.05 eq) in THF (2.5 M) is then added dropwise. After the addition is complete, the cooling bath is removed and the reaction is allowed to warm to rt. The reaction mixture is quenched with satd. aq. NH$_4$Cl, transferred to a separatory funnel, and extracted with EtOAc. The organic layer is washed with water, brine and dried over anhydrous Na$_2$SO$_4$. After filtration, the solvents are evaporated under reduced pressure to yield the product. The material is purified by recrystallization or column chromatography.

Step C': As described in Step B above.

Example XXI

Preparation of (3-Fluoro-phenyl)-[3-methyl-2-(1-methyl-piperidin-4-ylsulfanyl)-3H-imidazol-4-yl]-methanol

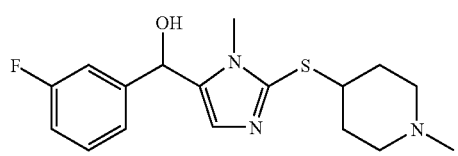

This example demonstrates the preparation of a compound of formula (I) following Scheme XV, wherein M is —CHOHR$^M$; R$^M$ is m-fluorophenyl; A$^3$ is sulfur; L$^3$ is absent; Q$^3$ is 4-(1-methyl-piperidyl); and Q$^1$ is methyl.

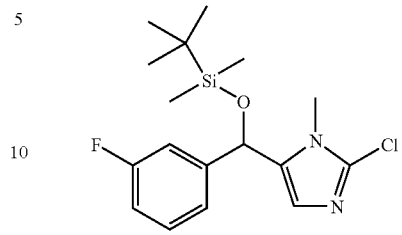

Step A. 5-[(3-Fluoro-phenyl)-(tert-butyl-dimethyl-silanyloxy)-methyl]-2-chloro-1-methyl-1H-imidazole. To a 0° C. solution of (3-fluoro-phenyl)-(2-chloro-3-methyl-3H-imidazol-4-yl)-methanol (1 equiv.) in CH$_2$Cl$_2$ (0.1 M) is added triethylamine (1.7 equiv.), t-butyldimethylsilyl chloride (1.5 equiv.), and 4-(dimethylamino)pyridine (0.05 equiv.). The resulting solution is warmed to rt and stirred overnight. The solution is diluted with satd. aq. NH$_4$Cl and extracted with EtOAc. The combined organic layers are dried over anhydrous Na$_2$SO$_4$, filtered, and concentrated. The crude material is purified by HPLC or flash column chromatography.

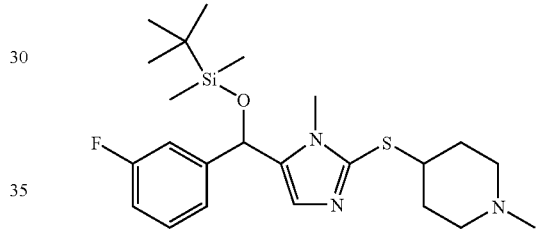

Step B. 4-{5-[(3-Fluoro-phenyl)-(tert-butyl-dimethyl-silanyloxy)-methyl]-1-methyl-1H-imidazol-2-ylsulfanyl}-1-methyl-piperidine. To a 0° C. solution of 1-methyl-piperidinethiol (1.5 equivalents) in THF (0.2 M) is added NaH (60% dispersion in oil, 1.5 equivalents). After 30 min, 5-[(3-fluoro-phenyl)-(tert-butyl-dimethyl-silanyloxy)-methyl]-2-chloro-1-methyl-1H-imidazole (1 equivalent) in THF (1 M) is added dropwise. The mixture is heated at reflux until HPLC analysis shows consumption of the starting material. The reaction mixture is cooled to rt, quenched with satd. aq. NH$_4$Cl, and extracted with EtOAc (2×). The combined organic extracts are washed with water and brine, dried over anhydrous Na$_2$SO$_4$, filtered and concentrated. The crude material is purified by HPLC or flash column chromatography to provide the desired product.

Step C. (3-Fluoro-phenyl)-[3-methyl-2-(1-methyl-piperidin-4-ylsulfanyl)-3H-imidazol-4-yl]-methanol. A solution of 4-{5-[(3-fluoro-phenyl)-(tert-butyl-dimethyl-silanyloxy)-methyl]-1-methyl-1H-imidazol-2-ylsulfanyl}-1-methyl-piperidine (1 equiv.) in THF (0.2 M) is treated with tetrabutylammonium fluoride (1.2 equiv.). When the reaction is complete, the solution is diluted with satd. aq. NaHCO$_3$ and extracted with EtOAc. The organic layer is dried over anhydrous Na$_2$SO$_4$. The crude material is purified by chromatography or recrystallization.

This material can then be oxidized to form the corresponding sulfoxide (A$^3$ is S(O)), or sulfone (A$^3$ is S(O$_2$)) as described in Example XVI, Scheme XI.

Example XXII

Preparation of (3-Fluoro-phenyl)-[2-(1-isopropyl-piperidin-4-ylmethoxy)-3-methyl-3H-imidazol-4-yl]-methanol

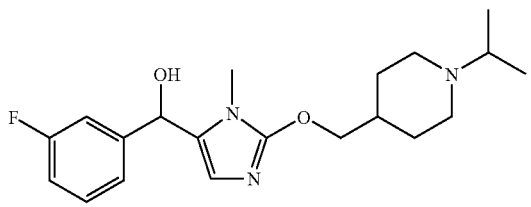

This example demonstrates the preparation of a compound of formula (I) following Scheme XV, wherein M is —CHOHR$^M$; R$^M$ is m-fluorophenyl; A$^3$ is oxygen; L$^3$ is methyl; Q$^3$ is 4-(1-isopropyl-piperidyl); and Q$^1$ is methyl.

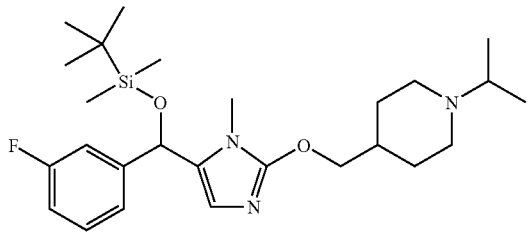

Step A. 4-{5-[(3-Fluoro-phenyl)-(tert-butyl-dimethyl-silanyloxy)-methyl]-1-methyl-1H-imidazol-2-yloxymethyl}-1-isopropyl-piperidine. To a 0° C. solution of (1-isopropyl-piperidin-4-yl)-methanol (1 equiv.) in THF (0.1 M) is added NaH (1.01 equiv.). The cooling bath is removed, and the reaction is warmed to rt. After 2 h, a solution of 5-[(3-fluoro-phenyl)-(tert-butyl-dimethyl-silanyloxy)-methyl]-2-chloro-1-methyl-1H-imidazole (1.01 equiv.) in dry THF (0.6 M) is added. The reaction mixture is then heated to 60° C. Upon completion of the reaction, mixture is cooled to rt, poured into ice-cold water, and extracted with EtOAc. The combined organic extracts are dried over anhydrous Na$_2$SO$_4$, filtered, and evaporated under reduced pressure to provide the crude material. The crude material is purified by chromatography or recrystallization.

Step B. (3-Fluoro-phenyl)-[3-methyl-2-(1-methyl-piperidin-4-ylsulfanyl)-3H-imidazol-4-yl]-methanol. A solution of 4-{5-[(3-fluoro-phenyl)-(tert-butyl-dimethyl-silanyloxy)-methyl]-1-methyl-1H-imidazol-2-yloxymethyl}-1-isopropyl-piperidine (1 equiv.) in THF (0.2 M) is treated with tetrabutylammonium fluoride (1.2 equiv.). When the reaction is complete, the solution is diluted with satd. aq. NaHCO$_3$ and extracted with EtOAc. The organic layer is dried over anhydrous Na$_2$SO$_4$. The crude material is purified by chromatography or recrystallization.

Example XXIII

Preparation of Derivatives of Compounds of Formula (I) With Quaternary Nitrogen Substituents Compounds of Formula:

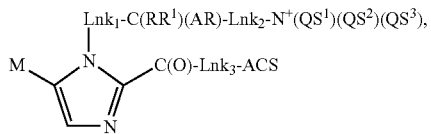

wherein the symbols for the substituents are as defined herein, are prepared with the 2- and 5-substitution regioselectivity as described herein in Schemes XIIIa-b, XIV, XV, the foregoing Examples, and equivalents thereof. The substituents -Lnk$_1$-C(RR$^1$)(AR)-Lnk$_2$-N$^+$(QS$^1$)(QS$^2$)(QS$^3$) and —C(O)-Lnk$_3$-ACS are prepared as described in, for example, U.S. Pat. Nos. 6,380,396 and 6,207,678, Schemes 1-5 therein, and illustrative examples thereof.

Example XXIV

Preparation of 2-Chloro-3-methyl-3H-imidazole-4-carboxylic acid

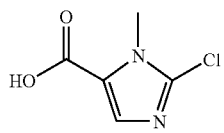

To a 1-L, three-necked, round-bottomed flask equipped with a magnetic stirrer, nitrogen inlet and an addition funnel is added 2-chloro-1-methyl-1H-imidazole (1 equiv.) and THF (0.5 M). The reaction mixture is cooled to −78° C. and n-BuLi (2.5 M in hexanes, 1.05 equiv.) is added. The resulting mixture is stirred for 1 h and a solution of CO$_2$ is bubbled into the solution. After the addition is complete, the cooling bath is removed and the reaction is allowed to warm to rt. The reaction mixture is quenched with satd. aq. NH$_4$Cl, transferred to a separatory funnel, and extracted with EtOAc. The organic layer is washed with water, brine and dried over anhydrous Na$_2$SO$_4$. After filtration, the solvents are evaporated under reduced pressure to yield the product. The material is purified by recrystallization or column chromatography.

Example XXV

The histamine H$_3$ receptor binding effectiveness of compounds of the present invention was determined using the human histamine H$_3$ receptor, Lovenberg, et al. *Mol. Pharmacol.* 1999, 1107. Screening using the human receptor is particularly important for the identification of new therapies for the treatment of human disease. Prior binding assays, for example, relied on rat synaptosomes (Garbarg, et al. *J. Pharmacol. Exp. Ther.* 1992, 263, 304), rat cortical membranes (West, et al. *Mol. Pharmacol.* 1990, 610), and guinea pig brain (Korte, et al. *Biochem. Biophys. Res. Commun.* 1990, 978). A recent comparative study comparing human H$_3$ receptor activity with H$_3$ receptors from rodent and primate have shown significant differences in the respective pharmacology of the rodent and primate receptors to the human receptor. (West, et al. *Eur. J. Pharmacol.* 1999, 233; Lovenberg, et al. *J. Pharmacol. Exp. Ther.* 2000, 293, 771-778.)

In Vitro

A. Transfection of Cells With Human Histamine Receptor

A 10 cm tissue culture dish with a confluent monolayer of SK-N-MC cells was split two days prior to transfection. Using sterile technique the media was removed and the cells were detached from the dish by the addition of trypsin. One fifth of the cells were then placed onto a new 10 cm dish. Cells were grown in a 37° C. incubator with 5% $CO_2$ in Minimal Essential Media Eagle with 10% Fetal Bovine Serum. After two days cells were approximately 80% confluent. These were removed from the dish with trypsin and pelleted in a clinical centrifuge. The pellet was then re-suspended in 400 μL complete media and transferred to an electroporation cuvette with a 0.4 cm gap between the electrodes (Bio-Rad #165-2088). One pg supercoiled $H_3$ receptor cDNA was added to the cells and mixed. The voltage for the electroporation was set at 0.25 kV, the capacitance is set at 960 μF. After electroporation the cells were diluted into 10 mL complete media and plated onto four 10 cm dishes. Because of the variability in the efficiency of electroporation four different concentrations of cells were plated. The ratios used were; 1:20, 1:10, 1:5, with the remainder of the cells being added to the fourth dish. The cells were allowed to recover for 24 h before adding the selection media (complete media with 600 μg/mL G418). After 10 days dishes were analyzed for surviving colonies of cells. Dishes with well-isolated colonies were used. Cells from individual colonies were isolated and tested. SK-N-MC cells were used because they give efficient coupling for inhibition of adenylate cyclase. The clones that gave the most robust inhibition of adenylate cyclase in response to histamine were used for further study.

B. [$^3$H]—N-methylhistamine Binding

Cell pellets from histamine $H_3$ receptor-expressing SK-N-MC cells were homogenized in 20 mM TrisHCl/0.5 mM EDTA. Supernatants from an 800 g spin were collected, recentrifuged at 30,000 g for 30 min. Pellets were re-homogenized in 50 mM Tris/5 mM EDTA (pH 7.4). Membranes were incubated with 0.8 nM [$^3$H]—N-methylhistamine plus/minus test compounds for 45 min at 25° C. and harvested by rapid filtration over GF/C glass fiber filters (pretreated with 0.3% polyethylenimine) followed by four washes with ice-cold buffer. Filters were dried, added to 4 mL scintillation cocktail and then counted on a liquid scintillation counter. Non-specific binding was defined with 10 μM histamine. P$K_i$ values were calculated based on a $K_D$ of 800 pM and a ligand concentration ([L]) of 800 pM according to the formula:

$$K_i=(IC_{50})/(1+([L]/(K_D)).$$

$K_i$ Values

| Example | Compound Name | $K_i$ (nM) |
|---|---|---|
| I | (4-Chloro-phenyl)-[2-(2-dimethylamino-ethyl-sulfanyl)-3-methyl-3H-imidazol-4-yl]-methanone | 98 |
| II | (4-Chlorophenyl)-[2-(3-dimethylamino-propylsulfanyl)-3-methyl-3H-imidazol-4-yl]-methanone | 2 |
| II | (4-Chlorophenyl)-[3-methyl-2-(3-piperidin-1-yl-propylsulfanyl)-3H-imidazol-4-yl]-methanone | 3.1 |
| III | (4-Bromophenyl)-[3-methyl-2-(3-piperidin-1-yl-propylsulfanyl)-3H-imidazol-4-yl]-methanone | 7.5 |
| III | (4-Bromophenyl)-[2-(3-dimethylamino-propylsulfanyl)-3-methyl-3H-imidazol-4-yl]-methanone | 1.6 |
| IV | (4-Chlorophenyl)-{3-methyl-2-[2-(1-methyl-pyrrolidin-2-yl)-ethylsulfanyl]-3H-imidazol-4-yl}-methanone | 2 |
| IV | [2-(3-Dimethylamino-propylsulfanyl)-3-methyl-3H-imidazol-4-yl]-phenyl-methanone | 4 |
| IV | (4-Chlorophenyl)-[3-methyl-2-(1-methyl-piperidin-4-ylsulfanyl)-3H-imidazol-4-yl]-methanone | 7 |
| V | (4-Chloro-phenyl)-[2-(1-isopropyl-piperidin-4-ylmethoxy)-3-methyl-3H-imidazol-4-yl]-methanone | 3.7 |
| V | (4-Chlorophenyl)-[3-methyl-2-(3-piperidin-1-yl-propylamino)-3H-imidazol-4-yl]-methanone | 32 |
| V | (4-Bromophenyl)-[2-(1-isopropyl-piperidin-4-ylmethoxy)-3-methyl-3H-imidazol-4-yl]-methanone | 5.3 |
| V | (4-Bromophenyl)-[2-(1-ethyl-piperidin-4-ylmethoxy)-3-methyl-3H-imidazol-4-yl]-methanone | 6.6 |
| V | (4-Bromophenyl)-[2-(1-sec-butyl-piperidin-4-ylmethoxy)-3-methyl-3H-imidazol-4-yl]-methanone | 9 |
| XI | (4-Chlorophenyl)-[2-(1-isopropyl-piperidin-4-yloxy)-3-methyl-3H-imidazol-4-yl]-methanone | 25 |
| XI | (4-Chlorophenyl)-[2-(1-isopropyl-piperidin-4-ylsulfanyl)-3-methyl-3H-imidazol-4-yl]-methanone | 3 |
| XII | [3-Methyl-2-(3-piperidin-1-yl-propoxy)-3H-imidazol-4-yl]-naphthalen-1-yl-methanone | 79 |
| XII | (2-Chlorophenyl)-[2-(1-isopropyl-piperidin-4-ylmethoxy)-3-methyl-3H-imidazol-4-yl]-methanone | 1.3 |
| XII | (4-Fluorophenyl)-[2-(1-isopropyl-piperidin-4-ylmethoxy)-3-methyl-3H-imidazol-4-yl]-methanone | 2.5 |
| XII | (3-Chlorophenyl)-[2-(1-isopropyl-piperidin-4-ylmethoxy)-3-methyl-3H-imidazol-4-yl]-methanone | 2.8 |
| XII | (3,5-Dichlorophenyl)-[2-(1-isopropyl-piperidin-4-ylmethoxy)-3-methyl-3H-imidazol-4-yl]-methanone | 4 |
| XII | [2-(1-Isopropyl-piperidin-4-ylmethoxy)-3-methyl-3H-imidazol-4-yl]-(4-trifluoromethyl-phenyl)-methanone | 4.1 |
| XII | [2-(1-Isopropyl-piperidin-4-ylmethoxy)-3-methyl-3H-imidazol-4-yl]-(4-nitro-phenyl)-methanone | 4.6 |
| XII | 4-{Hydroxy-[2-(1-isopropyl-piperidin-4-ylmethoxy)-3-methyl-3H-imidazol-4-yl]-methyl}-benzonitrile | 7.6 |
| XIII | {3-[5-(4-Chlorobenzyl)-1-methyl-1H-imidazol-2-ylsulfanyl]-propyl}-dimethyl-amine | 22 |
| XIV | (4-Chlorophenyl)-[2-(3-dimethylamino-propylsulfanyl)-3-methyl-3H-imidazol-4-yl]-methanone oxime | 3.2 |
| XV | [3-Methyl-2-(3-piperidin-1-yl-propoxy)-3H-imidazol-4-yl]-piperidin-1-yl-methane | 36.4 |
| XVI | (4-Chlorophenyl)-[2-(3-dimethylamino-propane-1-sulfinyl)-3-methyl-3H-imidazol-4-yl]-methanone | 315 |

References cited in the specification are incorporated herein by reference. Having described the invention in specific detail and exemplified the manner in which it may be carried into practice, it will be apparent to those skilled in the art that innumerable variations, applications, modifications, and extensions of the basic principles involved may be made without departing from its spirit or scope. It is to be understood that the foregoing is merely exemplary and the present invention is not to be limited to the specific form or arrangements of parts herein described and shown.

What is claimed is:

1. A method of making a compound of formula (I),

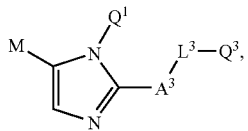

(I)

wherein:

$Q^1$ is selected from the group consisting of $C_{1-7}$alkyl and $C_{2-7}$alkenyl;

wherein $Q^1$ may be substituted with one or more substituents selected from the group consisting of halo, cyano, hydroxy, $OR^{11}$, $C_{1-5}$alkyl, $C_{1-5}$haloalkyl, $C_{2-5}$alkenyl, nitro, amino ($H_2N$—), $R^{11}HN$—, $R^{11}R^{12}N$—, amido ($H_2NC(O)$), $R^{11}HNC(O)$, $R^{11}R^{12}NC(O)$ and $R^{11}OC(O)$, and wherein $R^{11}$ and $R^{12}$ are independently $C_{1-6}$alkyl, $C_{1-6}$haloalkyl or $C_{2-6}$alkenyl; or $Q^1$ is -$Lnk_1$-$C(RR^1)(AR)$-$Lnk_2$-$N^+(QS^1)(QS^2)(QS^3)$, wherein $Lnk_1$ is a bond or $C_{2-4}$alkylene, optionally substituted with at least one of $C_{1-4}$alkyl, halo$C_{1-4}$alkyl, $C_{1-4}$alkoxy, halo$C_{1-4}$alkoxy, fluoro, chloro, bromo, iodo, and cyano;

$RR^1$ is H or $C_{1-6}$alkyl, optionally substituted with at least one of $C_{1-4}$alkyl, halo$C_{1-4}$alkyl, $C_{1-4}$alkoxy, halo$C_{1-4}$alkoxy, fluoro, chloro, bromo, iodo, and cyano;

AR is phenyl, naphthyl, benzyl, thienyl, benzo[b]thienyl, or indolyl, each of which is optionally substituted with 1 to 3 substituents, each of said substituents independently selected from $C_{1-4}$alkyl, halo$C_{1-4}$alkyl, $C_{1-4}$alkoxy, halo$C_{1-4}$alkoxy, fluoro, chloro, bromo, iodo, and cyano, or AR is 1,3-benzodioxolan-4 or 5-yl or 1,4-benzodioxan-5 or 6-yl;

$Lnk_2$ is a bond or $C_{2-4}$alkylene, optionally substituted with at least one of $C_{1-4}$alkyl, halo$C_{1-4}$alkyl, $C_{1-4}$alkoxy, halo$C_{1-4}$alkoxy, fluoro, chloro, bromo, iodo, and cyano; and each of $QS^1$, $QS^2$, and $QS^3$ is independently selected from H, $C_{1-6}$alkyl, optionally substituted with at least one of $C_{1-4}$alkyl, halo$C_{1-4}$alkyl, $C_{1-4}$alkoxy, halo$C_{1-4}$alkoxy, fluoro, chloro, bromo, iodo, and cyano, or any two of $QS^1$, $QS^2$, and $QS^3$ are taken together to form, together with the attachment quaternary nitrogen member, a heterocycle, while the third is selected from $C_{1-6}$alkyl, optionally substituted with at least one of $C_{1-4}$alkyl, $C_{1-4}$alkoxy, fluoro, chloro, bromo, iodo, and cyano, or the three $QS^1$, $QS^2$, and $QS^3$ are taken together to form, together with the attachment quaternary nitrogen member, optionally substituted quinuclidinium

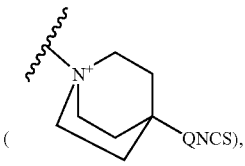

(QNCS), wherein QNCS is H or one of $C_{1-6}$alkyl, phenyl, naphthyl, benzyl, pyridyl, thienyl, $C_{3-7}$cycloalkyl, each of which being optionally substituted with at least one of $C_{1-4}$alkyl, halo$C_{1-4}$alkyl, $C_{1-4}$alkoxy, halo$C_{1-4}$alkoxy, fluoro, chloro, bromo, iodo, and cyano;

M is a moiety of the formula —$CH_2R^M$, —$CHOHR^M$, —$C(=O)R^M$ or —$C(=N-OH)R^M$, wherein $R^M$ is selected from the group consisting of H, hydroxy, $C_{1-7}$alkyl, $R^{M1}HN$—, $R^{M1}R^{M2}N$—, cycloalkyl, aryl, biaryl and heterocyclyl, where when M is —$CHOHR^M$, then $R^M$ is not $R^{M1}HN$— or $R^{M1}R^{M2}N$—, wherein $R^M$ may be substituted with one or more substituents independently selected from the group consisting of halo, cyano, hydroxy, $OR^{M1}$, $C_{1-6}$alkyl, $C_{1-6}$haloalkyl, $C_{2-6}$alkenyl, nitro, amino($H_2N$—), $R^{M1}HN$—, $R^{M1}R^{M2}N$—, amido ($H_2NC(O)$), $R^{M1}HNC(O)$ and $R^{M1}R^{M2}NC(O)$, and wherein $R^{M1}$ and $R^{M2}$ are either independently selected from H, $C_{1-6}$alkyl, $C_{1-6}$haloalkyl, and $C_{2-5}$alkenyl, or $R^{M1}$ and $R^{M2}$ are taken together to form $C_{4-7}$alkylene;

or M is hydrogen;

$A^3$ is NH, $NR^3$, sulfur, sulfoxide, sulfone or oxygen, wherein $R^3$ is $C_{1-6}$alkyl;

$L^3$ is $C_{1-7}$alkyl or $C_{2-7}$alkenyl;

wherein $L^3$ may be substituted with one or more substituents selected from the group consisting of halo, hydroxy, methoxy and amino ($H_2N$—);

or $L^3$ is absent; and $Q^3$ is selected from the group consisting of $C_{1-7}$alkyl, $C_{2-7}$alkenyl, $C_{3-7}$cycloalkyl, $C_{5-7}$cycloalkenyl, aryl, 4-7 membered heterocyclyl, ($C_{3-7}$cycloalkyl)-(4-7 membered heterocyclyl), (4-7 membered heterocyclyl)-($C_{3-7}$ cycloalkyl), and bi-(4-7 membered heterocyclyl), and when $L^3$ is not absent, then $Q^3$ is additionally selected from the group consisting of $R^{31}HN$—, $R^{31}R^{32}N$—, azinoyl ($R^{31}HN^+(O^-)$ or $R^{31}R^{32}N^+(O^-)$), $C_{3-7}$cycloalkylamino, 4-7 membered heterocyclylamino, aryl $C_{1-6}$alkylamino, $C_{3-7}$ cycloalkylsulfanyl, 4-7 membered heterocyclylsulfanyl, and 4-7 membered heterocycly-loxy;

wherein $Q^3$ may be substituted with one or more substituents selected from the group consisting of halo, cyano, hydroxy, $OR^{31}$, $C_{1-5}$alkyl, $C_{1-5}$haloalkyl, $C_{2-5}$alkenyl, nitro, amino ($H_2N$—), $R^{31}HN$—, $R^{31}R^{32}N$—, amido ($H_2NC(O)$), $R^{31}HNC(O)$, $R^{31}R^{32}NC(O)$, $R^{31}OC(O)$, $C_{3-7}$cycloalkyl, monocyclic 4-7 membered heterocyclyl, and (monocyclic 4-7 membered heterocyclyl)-($C_{1-6}$alkyl), and wherein $R^{31}$ and $R^{32}$ are independently $C_{1-5}$alkyl, $C_{1-5}$haloalkyl or $C_{2-5}$alkenyl;

or wherein the moiety -$A^3$-$L^3$-$Q^3$ is —$C(O)$-$Lnk_3$-ACS, wherein Lnk₃ is a bond or $C_{2-4}$alkylene, optionally substituted with at least one of $C_{1-4}$alkyl, halo$C_{1-4}$alkyl, $C_{1-4}$alkoxy, halo$C_{1-4}$alkoxy, fluoro, chloro, bromo, iodo, and cyano; and ACS is one of H; $C_{1-6}$alkyl, optionally substituted with at least one of $C_{1-4}$alkyl, halo$C_{1-4}$alkyl, $C_{1-4}$alkoxy, halo$C_{1-4}$alkoxy, fluoro, chloro, bromo, iodo, and cyano; and ACS1, wherein ACS1 is selected from phenyl, $C_{3-7}$cycloalkyl, and heteroaryl, each of said ACS1 being optionally benzo- or $C_{3-7}$cycloalkyl-fused, and optionally substituted, including any of the benzo- and $C_{3-7}$cycloalkyl-fused portions, by from 1 to 3 substituents, each independently selected from $C_{1-4}$alkyl, halo$C_{1-4}$alkyl, $C_{1-4}$alkoxy, halo$C_{1-4}$alkoxy, fluoro, chloro, bromo, iodo, cyano, phenoxy, $C_{2-4}$alkanoyl, $C_{,1-4}$alkoxycarbonyl, $C_{3-7}$cycloalkyl, —S(O)$_m$($C_{1-4}$alkyl), —NR$^{M1}$R$^{M2}$, —S(O)$_m$NR$^{M1}$R$^{M2}$, —N(R$^{M3}$)$C_{1-4}$alkanoyl, and —C(O)NR$^{M1}$R$^{M2}$, or ACS is 2,3-dihydrobenzo[b]furanyl or chromanyl, wherein R$^{M3}$ is one of H, and $C_{1-6}$alkyl, optionally substituted with at least one of $C_{1-4}$alkyl, halo$C_{1-4}$alkyl, $C_{1-4}$alkoxy, halo$C_{1-4}$alkoxy, fluoro, chloro, bromo, iodo, and cyano, where m=0, 1, or 2;

or a pharmaceutically acceptable salt, ester, ether, N-oxide, amide, hydrate, solvate or isotopically labeled form thereof, comprising: Reacting an imidazole compound of formula (A) with a base and at least one of a perhaloalkane (PHA) or an N-F electrophilic fluorinating agent (EFA), to form a 2-haloimidazole compound of formula (B), according to:

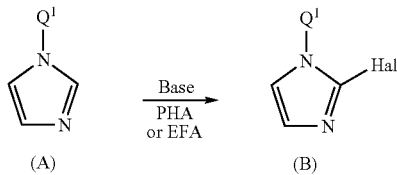

wherein Hal is F or Cl; and

Reacting compound of formula (B) with a base and performing an addition with an electrophile (D) to form a C-5 position substituted imidazole compound of formula (C), according to:

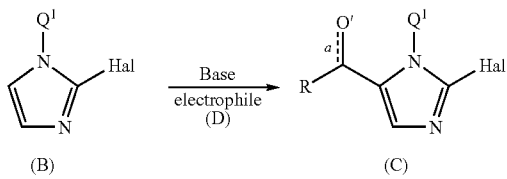

wherein the set of (D), a, X, O' and R is one of the following assignment sets (i)-(iv):
(i) electrophile (D) is O═C(X)R, a is a single bond, X is H, O' is OH, and R is R$^M$;
(ii) electrophile (D) is O═C(X)R, a is a double bond, X is —N(OMe)Me or —N(Me)$_2$, O' is O, and R is R$^M$;
(iii) electrophile (D) is CO$_2$, a is a double bond, R is hydroxy, and O' is O; and
(iv) electrophile (D) is O═C(X)R, a is a double bond, O' is O, R is R$^m$, and X is fluoro, chloro, bromo or iodo.

2. A method according to claim 1, wherein said at least one of a PHA and an EFA is a perhaloalkane.

3. A method according to claim 1, wherein said at least one of a PHA and an EFA is a perhalo$C_{2-6}$alkane.

4. A method according to claim 1, wherein said at least one of a PHA and an EFA is a perhalo$C_{2-4}$alkane.

5. A method according to claim 1, wherein said at least one of a PHA and an EFA is a perchloro$C_{2-6}$alkane.

6. A method according to claim 1, wherein said at least one of a PHA and an EFA is a perchloro$C_{2-4}$alkane.

7. A method according to claim 1, wherein said at least one of a PHA and an EFA is hexachloroethane.

8. A method according to claim 1, wherein said at least one of a PHA and an EFA is at least one of 1-chloromethyl-4-fluoro-1,4-diazoniabicyclo[2.2.2]octane bis-(tetrafluoroborate); N-fluorobenzenesulfonamide; N-fluoropyridinium triflate; N-fluoroquiniclidinium triflate and mixtures thereof.

9. A method according to claim 1, wherein said base is an organolithium compound.

10. A method according to claim 1, wherein said base is one of LDA, LiHMDS, t-BuLi, sec-BuLi, n-BuLi, and mixtures thereof.

11. A method according to claim 1, wherein said base is n-BuLi.

12. A method according to claim 1, wherein Q$^1$ is selected from the group consisting of $C_{1-7}$alkyl, $C_{1-7}$haloalkyl and $C_{2-7}$alkenyl;

wherein Q$^1$ may be substituted with one or more substituents selected from the group consisting of halo, cyano, hydroxy, OR$^{11}$, $C_{1-5}$alkyl, $C_{1-5}$haloalkyl, $C_{2-5}$alkenyl, nitro, amino (H$_2$N—), R$^{11}$HN—, R$^{11}$R$^{12}$N—, amido (H$_2$NC(O)), R$^{11}$HNC(O), R$^{11}$R$^{12}$NC(O) and R$^{11}$OC(O), and wherein R$^{11}$ and R$^{12}$ are independently $C_{1-6}$alkyl, $C_{1-6}$haloalkyl or $C_{2-6}$alkenyl.

13. A method according to claim 1, wherein Q$^1$ is methyl.

14. A method according to claim 1, wherein Hal is chloro.

15. A method according to claim 1, wherein said reacting compound of formula (A) with a base is performed at a temperature from about 0° C. to about −100° C.

16. A method according to claim 1, wherein said reacting compound of formula (A) with a base is performed at a temperature from about −20° C. to about −90° C.

17. A method according to claim 1, wherein said reacting compound of formula (A) with a base is performed at a temperature of about −78° C.

18. A method according to claim 1, wherein Q$^1$ is selected from the group consisting of $C_{1-7}$alkyl and $C_{2-7}$alkenyl;

wherein Q$^1$ may be substituted with one or more substituents selected from the group consisting of halo, cyano, hydroxy, OR$^{11}$, $C_{1-5}$alkyl, $C_{1-5}$haloalkyl, $C_{2-5}$alkenyl, nitro, amino (H$_2$N—), R$^{11}$HN—, R$^{11}$R$^{12}$N—, amido (H$_2$NC(O)), R$^{11}$HNC(O), R$^{11}$R$^{12}$NC(O) and R$^{11}$OC(O), and wherein R$^{11}$ and R$^{12}$ are independently $C_{1-6}$alkyl, $C_{1-6}$haloalkyl or $C_{2-6}$alkenyl.

19. A method according to claim 1, wherein Q$^1$ is methyl.

20. A method according to claim 1, wherein Hal is fluoro or chloro.

21. A method according to claim 1, wherein Hal is chloro.

22. A method according to claim 1, wherein a is a double bond.

23. A method according to claim 1, wherein O' is O.

24. A method according to claim 1, wherein a is a single bond.

25. A method according to claim 1, wherein a is a single bond and O' is OH.

26. A method according to claim 1, wherein said base is an organollithium compound.

27. A method according to claim 1, wherein said base is one of LDA, LiHMDS, t-BuLi, sec-BuLi, n-BuLi, and mixtures thereof.

28. A method according to claim 1, wherein said base is n-BuLi.

29. A method according to claim 1, wherein said reacting compound of formula (B) with a base is performed at a temperature from about 0° C. to about −100° C.

30. A method according to claim 1, wherein said reacting compound of formula (B) with a base is performed at a temperature from about −20° C. to about −90° C.

31. A method according to claim 1, wherein said reacting compound of formula (B) with a base is performed at a temperature of about −78° C.

32. A method according to claim 1, wherein said electrophile (D) satisfies one of:
(D) is O=C(X)R, with a being a single bond, X being H, O' being OH, and R being $R^M$;
(D) is O=C(X)R, with a being a double bond, X being —N(OMe)Me or —N(Me)$_2$, O' being O, and R being $R^M$;
(D) is $CO_2$, with a being a double bond, and O' being O, R being hydroxy; and
(D) is O=C(X)R, with a being a double bond, O' being O, R being $R^M$, X being fluoro, chloro, bromo or iodo.

33. A method according to claim 1, wherein R is one of phenyl or halophenyl.

34. A method according to claim 1, wherein R is benzyl substituted with one of cyano, nitro, and trifluoromethyl.

35. A method according to claim 1, wherein R is phenyl substituted with at least two halo groups.

36. A method according to claim 1, wherein a is a double bond and O' is N—OH.

37. A method according to claim 1, further comprising reacting compound (41) with a deprotonated nucleophile, wherein O' is O, a is a double bond, R is $R^M$, and said nucleophile is H-$A^3$-$L^3$-$Q^3$.

38. A method according to claim 1, further comprising reacting compound (41) with a deprotonated oxygen or sulfur nucleophile, wherein O' is O, a is a double bond, R is $R^M$, and said nucleophile is H-$A^3$-$L^3$-$Q^3$, with $A^3$ being O or S.

39. A method according to claim 1, further comprising reacting compound (41) with a deprotonated oxygen or sulfur nucleophile, wherein O' is O, a is a double bond, R is $R^M$, and said nucleophile is H-$A^3$-$L^3$-$Q^3$, with $A^3$-$L^3$-$Q^3$ being one of 1-isopropyl-piperidin-4-ylmethoxy, 3-dimethylamino-propylsulfanyl, 2-(1-methylpyrrolidin-2-yl)-ethylsulfanyl, 1-isopropyl-piperidin-4-ylsulfanyl, 3-piperidin-1-yl-propylsulfanyl, 3-dimethylamino-propylsulfanyl, 1-ethyl-piperidin-4-ylmethoxy, 1-methyl-piperidin-4-ylsulfanyl, and 1-sec-butyl-piperidin-4-ylmethoxy.

40. A method according to claim 1, further comprising treating compound (41) with a nucleophilic primary amine $H_2N$-$L^3$-$Q^3$ in the presence of a base, wherein O' is O, a is a double bond, and R is $R^M$.

41. A method according to claim 1, further comprising treating compound (41) with a nucleophilic secondary amine $HR^3N$-$L^3$-$Q^3$ in the presence of a base, wherein O' is O, a is a double bond, and R is $R^M$.

42. A method according to claim 1, further comprising performing hydroxy protection, where O' is OH and a is a single bond, to form a hydroxy-protected compound, reacting said hydroxy-protected compound with a deprotonated nucleophile, wherein R is $R^M$, and said nucleophile is H-$A^3$-$L^3$-$Q^3$, and optionally performing hydroxy deprotection.

43. A method according to claim 1, further comprising performing hydroxy protection, where O' is OH and a is a single bond to form a hydroxy-protected compound, reacting said hydroxy-protected compound with a deprotonated oxygen or sulfur nucleophile, wherein R is $R^M$, and said nucleophile is H-$A^3$-$L^3$-$Q^3$, with $A^3$ being O or S, and optionally performing hydroxy deprotection.

44. A method according to claim 1, further comprising treating compound (41) with a nucleophilic primary amine $H_2N$-$L^3$-$Q^3$ in the presence of a base, wherein O' is OH, a is a single bond, and R is $R^M$, and optionally further comprising at least one of hydroxy protection, and hydroxy protection with subsequent hydroxy deprotection.

45. A method according to claim 1, further comprising treating compound (41) with a nucleophilic secondary amine $HR^3N$-$L^3$-$Q^3$ in the presence of a base, wherein O' is OH, a is a single bond, and R is $R^M$, and optionally further comprising at least one of hydroxy protection, and hydroxy protection with subsequent hydroxy deprotection.

46. A method according to claim 1, further comprising treating compound (41')

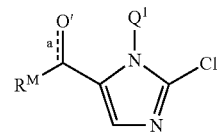

41' with a deprotonated sulfur nucleophile reagent H-$A^3$-$L^3$-$Q^4$, wherein $A^3$ is S, $Q^4$ is hydrogen, O' is O, and a is a double bond.

47. A method according to claim 1, wherein $Q^1$ is -Lnk$_1$-C(RR$^1$)(AR)-Lnk$_2$-N$^+$(QS$^1$)(QS$^2$)(QS$^3$), where Lnk$_1$ is a bond or $C_{2-4}$alkylene, optionally substituted with at least one of $C_{1-4}$alkyl, halo$C_{1-4}$alkyl, $C_{1-4}$alkoxy, halo$C_{1-4}$alkoxy, fluoro, chloro, bromo, iodo, and cyano;

RR$^1$ is H or $C_{1-6}$alkyl, optionally substituted with at least one of $C_{1-4}$alkyl, halo$C_{1-4}$alkyl, $C_{1-4}$alkoxy, halo$C_{1-4}$alkoxy, fluoro, chloro, bromo, iodo, and cyano;

AR is phenyl, naphthyl, benzyl, thienyl, benzo[b]thienyl, or indolyl, each of which is optionally substituted with 1 to 3 substituents, each of said substituents independently selected from $C_{1-4}$alkyl, halo$C_{1-4}$alkyl, $C_{1-4}$alkoxy, halo$C_{1-4}$alkoxy, fluoro, chloro, bromo, iodo, and cyano, or AR is 1,3-benzodioxolan-4 or 5-yl or 1,4-benzodioxan-5 or 6-yl;

Lnk$_2$ is a bond or $C_{2-4}$alkylene, optionally substituted with at least one of $C_{1-4}$alkyl, halo$C_{1-4}$alkyl, $C_{1-4}$alkoxy, halo$C_{1-4}$alkoxy, fluoro, chloro, bromo, iodo, and cyano; and each of QS$^1$, QS$^2$, and QS$^3$ is independently selected from H, $C_{1-6}$alkyl, optionally substituted with at least one of $C_{1-4}$alkyl, halo$C_{1-4}$alkyl, $C_{1-4}$alkoxy, halo$C_{1-4}$alkoxy, fluoro, chloro, bromo, iodo, and cyano, or any two of QS$^1$, QS$^2$, and QS$^3$ are taken together to form, together with the attachment quaternary nitrogen member, a heterocycle, while the third is selected from $C_{1-6}$alkyl, optionally substituted with at least one of $C_{1-4}$alkyl, $C_{1-4}$alkoxy, fluoro, chloro, bromo, iodo, and cyano, or the three QS¹, QS², and QS³ are taken together to form, together with the attachment quaternary nitrogen member, optionally substituted quinuclidinium

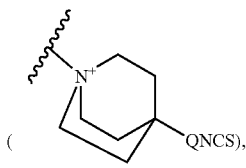

wherein QNCS is H or one of $C_{1-6}$alkyl, phenyl, naphthyl, benzyl, pyridyl, thienyl, $C_{3-7}$cycloalkyl, each of which being optionally substituted with at least one of $C_{1-4}$alkyl, halo$C_{1-4}$alkyl, $C_{1-4}$alkoxy, halo$C_{1-4}$alkoxy, fluoro, chloro, bromo, iodo, and cyano.

48. A method according to claim 1, wherein said compound of formula (I) is the compound of formula (11):

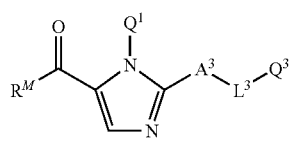

further comprising: treating a compound of formula (C) wherein a is a double bond, O' is O, and R is $R^M$, with a reagent $H-A^3-L^3-Q^3$, in the presence of a base yielding said compound of formula (11).

49. A method according to claim 1, wherein said compound of formula (I) is the compound of formula (11):

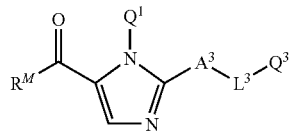

further comprising: treating a compound of formula (C) wherein a is a double bond, O' is O, and R is $R^M$, with a reagent $H-A^3-L^3-Q^4$, wherein $A^3$ is S and $Q^4$ is hydrogen, in the presence of a base yielding a compound of formula (5b)

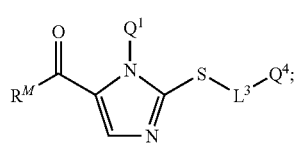

treating a compound of the formula (5b) with an oxidizing agent resulting in an intermediate compound of formula (10)

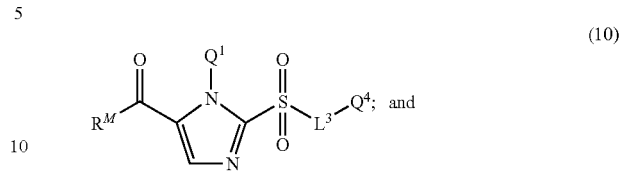

treating said intermediate compound of formula (10) with a reagent $H-A^3-L^3-Q^3$, wherein $L^3$ of the reagent $H-A^3-L^3-Q^3$ is independent of $L^3$ of formula (5b) and formula (10), in the presence of a base yielding said compound of formula (11).

50. A method according to claim 49, wherein said oxidizing agent is hydrogen peroxide in acetic acid, or 3-chloroperoxybenzoic acid in dichloromethane or diethyl ether.

51. A method according to claim 49, wherein said base is an alkali metal hydride.

52. A method according to claim 51, wherein said alkali metal hydride is sodium hydride.

53. A method according to claim 49, wherein said treating said intermediate in the presence of a base is performed in a solvent selected from the group consisting of DMF, benzene, 1,2-dimethoxyethane, tetrahydrofuran, and mixtures thereof.

54. A method according to claim 53, wherein said solvent is tetrahydrofuran.

55. A method according to claim 1, wherein:

$Q^1$ is $C_{1-3}$alkyl;

wherein $Q^1$ may be substituted with one substituent selected from the group consisting of amino, $R^{11}HN—$, $R^{11}R^{12}N—$, amido, $R^{11}HNC(O)$, $R^{11}R^{12}NC(O)$ and $R^{11}OC(O)$, and wherein $R^{11}$ and $R^{12}$ are independently $C_{1-5}$alkyl, $C_{1-5}$haloalkyl or $C_{2-5}$alkenyl;

M is a moiety of the formula $—CH_2R^M$, $—CHOHR^M$, or $—C(=O)R^M$, wherein $R^M$ is selected from the group consisting of $C_{1-3}$alkyl, $R^{M1}HN—$, $R^{M1}R^{M2}N—$, $C_{5-7}$cycloalkyl, aryl, biaryl and 4-7 membered heterocyclyl containing between 1 and 2 heteroatoms, where when M is $—CHOHR^M$, then $R^M$ is not $R^{M1}HN—$ or $R^{M1}R^{M2}N—$, wherein $R^M$ may be substituted with one or more substituents independently selected from the group consisting of halo, cyano, hydroxy, $OR^{M1}$, $C_{1-5}$alkyl, nitro, and amino; and $A^3$ is sulfur or oxygen;

$L^3$ is $C_{1-7}$alkyl or $C_{2-7}$alkenyl;

wherein $L^3$ may be substituted with one or more substituents selected from the group consisting of halo, hydroxy, methoxy and amino ($H_2N—$);

or $L^3$ is absent; and $Q^3$ is selected from the group consisting of $C_{1-7}$alkyl, $C_{2-7}$alkenyl, $C_{3-7}$cycloalkyl, $C_{5-7}$cycloalkenyl, aryl, 4-7 membered heterocyclyl, ($C_{3-7}$cycloalkyl)-(4-7 membered heterocyclyl), (4-7 membered heterocyclyl)-($C_{3-7}$cycloalkyl), bi-(4-7 membered heterocyclyl), and when $L^3$ is not absent, then $Q^3$ is additionally selected from the group consisting of $R^{31}HN—$, $R^{31}R^{32}N—$, azinoyl, $C_{3-7}$cycloalkylamino, 4-7 membered heterocyclylamino, aryl $C_{1-6}$alkylamino, $C_{3-7}$cycloalkylsulfanyl, 4-7 membered heterocyclylsulfanyl, and 4-7 membered heterocyclyloxy;

wherein $Q^3$ may be substituted with one or more substituents selected from the group consisting of halo, cyano, hydroxy, $OR^3$, $C_{1-5}$alkyl, $C_{1-5}$haloalkyl, $C_{2-5}$alkenyl, nitro, amino, $R^{31}HN-$, $R^{31}R^{32}N-$, amido, $R^{31}HNC(O)$, $R^{31}R^{32}NC(O)$, $R^{31}OC(O)$, $C_{3-7}$cycloalkyl, monocyclic 4-7 membered heterocyclyl, and (monocyclic 4-7 membered heterocyclyl)-alkyl, and wherein $R^{31}$ and $R^{32}$ are independently $C_{1-5}$alkyl, $C_{1-5}$haloalkyl or $C_{2-5}$alkenyl;

or a pharmaceutically acceptable ester, ether, N-oxide, amide, salt, hydrate, solvate or isotopically labeled form thereof.

56. A method according to claim 55, wherein the compound of formula (I) is selected from:
- (4-Chloro-phenyl)-[2-(2-dimethylamino-ethylsulfanyl)-3-methyl-3H-imidazol-4-yl]-methanone;
- (4-Chlorophenyl)-[2-(2-dimethylamino-ethylsulfanyl)-3-methyl-3H-imidazol-4-yl]-methanol;
- (4-Chlorophenyl)-[2-(3-dimethylamino-propylsulfanyl)-3-methyl-3H-imidazol-4-yl]-methanol;
- (4-Bromophenyl)-(2-mercapto-3-methyl-3H-imidazol-4-yl)-methanol;
- (4-Chlorophenyl)-[3-methyl-2-(4-methylpentylsulfanyl)-3H-imidazol-4-yl]-methanol;
- (4-Chlorophenyl)-[3-methyl-2-(4-methylpentylsulfanyl)-3H-imidazol-4-yl]-methanone;
- (4-Chlorophenyl)-[3-methyl-2-(3-piperidin-1-yl-propylsulfanyl)-3H-imidazol-4-yl]-methanol;
- (4-Chloro-phenyl)-{3-methyl-2-[2-(tetrahydropyran-2-yloxy)-ethylsulfanyl]-3H-imidazol-4-yl}-methanol;
- 2-{5-[(4-Chlorophenyl)-hydroxy-methyl]-1-methyl-1H-imidazol-2-ylsulfanyl}-ethanol;
- (4-Chloro-phenyl)-[2-(2-cyclohexylsulfanyl-ethylsulfanyl)-3-methyl-3H-imidazol-4-yl]-methanol;
- (4-Chloro-phenyl)-{3-methyl-2-[2-(tetrahydropyran-2-yloxy)-ethylsulfanyl]-3H-imidazol-4-yl}-methanone;
- (4-Chlorophenyl)-[2-(2-hydroxyethylsulfanyl)-3-methyl-3H-imidazol-4-yl]-methanone;
- (4-Chloro-phenyl)-[2-(2-cyclohexylsulfanyl-ethylsulfanyl)-3-methyl-3H-imidazol-4-yl]-methanone;
- Dimethyl-[3-(1-methyl-1H-imidazol-2-ylsulfanyl)-propyl]-amine;
- (4-Chlorophenyl)-[2-(3-dimethylamino-propylsulfanyl)-3-methyl-3H-imidazol-4-yl]-methanone;
- (4-Bromophenyl)-[2-(3-chloro-propylsulfanyl)-3-methyl-3H-imidazol-4-yl]-methanol;
- (4-Bromophenyl)-[3-methyl-2-(3-piperidin-1-yl-propylsulfanyl)-3H-imidazol-4-yl]-methanol;
- (4-Chlorophenyl)-[3-methyl-2-(3-morpholin-4-yl-propylsulfanyl)-3H-imidazol-4-yl]-methanol;
- (4-Chlorophenyl)-[3-methyl-2-(3-morpholin-4-yl-propylsulfanyl)-3H-imidazol-4-yl]-methanone;
- (4-Bromophenyl)-[2-(3-cyclohexylamino-propylsulfanyl)-3-methyl-3H-imidazol-4-yl]-methanone;
- [2-(3-Benzylamino-propylsulfanyl)-3-methyl-3H-imidazol-4-yl]-(4-bromo-phenyl)-methanone;
- (4-Bromophenyl)-[3-methyl-2-(3-thiomorpholin-4-yl-propylsulfanyl)-3H-imidazol-4-yl]-methanone;
- (4-Chlorophenyl)-[3-methyl-2-(3-piperidin-1-yl-propylsulfanyl)-3H-imidazol-4-yl]-methanone;
- (4-Bromophenyl)-[3-methyl-2-(3-piperidin-1-yl-propylsulfanyl)-3H-imidazol-4-yl methanone;
- (4-Chlorophenyl)-[2-(3-chloro-propylsulfanyl)-3-methyl-3H-imidazol-4-yl]-methanol;
- (4-Bromophenyl)-[2-(3-dimethylamino-propylsulfanyl)-3-methyl-3H-imidazol-4-yl]-methanone;
- (4-Chloro-phenyl)-{2-[3-(3,4-didehydropiperidin-1-yl)-propylsulfanyl]-3-methyl-3H-imidazol-4-yl}-methanone;
- (4-Chloro-phenyl)-[3-methyl-2-(3-thiomorpholin-4-yl-propylsulfanyl)-3H-imidazol-4-yl]-methanone;
- [2-(3-[1,4']Bipiperidinyl-1'-yl-propylsulfanyl)-3-methyl-3H-imidazol-4-yl]-(4-chloro-phenyl)-methanone;
- (4-Bromophenyl)-[2-(3-chloro-propylsulfanyl)-3-methyl-3H-imidazol-4-yl]-methanone;
- (4-Chloro-phenyl)-{3-methyl-2-[2-(1-methyl-pyrrolidin-2-yl)-ethylsulfanyl]-3H-imidazol-4-yl}-methanone;
- (4-Chloro-phenyl)-[2-(3-dimethylamino-2-methyl-propylsulfanyl)-3-methyl-3H-imidazol-4-yl]-methanone;
- (4-Chloro-phenyl)-[3-methyl-2-(1-methyl-piperidin-4-ylsulfanyl)-3H-imidazol-4-yl]-methanone;
- (4-Chloro-phenyl)-{3-methyl-2-[3-(4-methyl-piperazin-1-yl)-propylsulfanyl]-3H-imidazol-4-yl}-methanone;
- [2-(3-Dimethylamino-propylsulfanyl)-3-methyl-3H-imidazol-4-yl]-phenyl-methanone;
- (4-Chlorophenyl)-[2-(1-isopropylpiperidin-4-ylmethoxy)-3-methyl-3H-imidazol-4-yl]-methanone;
- (4-Chlorophenyl)-(3-methyl-2-propylsulfanyl-3H-imidazol-4-yl)-methanol;
- (4-Chlorophenyl)-(3-methyl-2-propylsulfanyl-3H-imidazol-4-yl)-methanone;
- (4-Chlorophenyl)-[3-methyl-2-(propane-1-sulfonyl)-3H-imidazol-4-yl]-methanone;
- (4-Chloro-phenyl)-(2-methanesulfinyl-3-methyl-3H-imidazol-4-yl)-methanone;
- (4-Chlorophenyl)-[3-methyl-2-(2-piperidin-1-yl-ethoxy)-3H-imidazol-4-yl]-methanone;
- (4-Chlorophenyl)-[3-methyl-2-(3-piperidin-1-yl-propoxy)-3H-imidazol-4-yl]-methanone;
- (4-Chlorophenyl)-[3-methyl-2-(3-piperidin-1-yl-propylamino)-3H-imidazol-4-yl]-methanone;
- (4-Bromophenyl)-[3-methyl-2-(3-piperidin-1-yl-propoxy)-3H-imidazol-4-yl]-methanone;
- (4-Bromo-phenyl)-[2-(1-isopropyl-piperidin-4-yloxy)-3-methyl-3H-imidazol-4-yl]-methanone;
- (4-Bromophenyl)-[2-(1-isopropyl-piperidin-4-ylmethoxy)-3-methyl-3H-imidazol-4-yl]-methanone;
- (4-Chlorophenyl)-[2-(3-dimethylamino-propoxy)-3-methyl-3H-imidazol-4-yl]-methanone;
- 4-[5[(4-bromobenzoyl)-1-methyl-1H-imidazol-2-yloxymethyl]-piperidine-1-carboxylic acid tert-butyl ester;
- (4-Bromophenyl)-{2-[2-(4-isopropyl-piperazin-1-yl)-ethoxy]-3-methyl-3H-imidazol-4-yl}-methanone;
- [3-Methyl-2-(3-piperidin-1-yl-propoxy)-3H-imidazol-4-yl]-phenyl-methanone;
- (4-Bromophenyl)-{2-[2-(1-isopropyl-piperidin-4-ylidene)-ethoxy]-3-methyl-3H-imidazol-4-yl}-methanone;
- (4-Bromophenyl)-[3-methyl-2-(piperidin-4-ylmethoxy)-3H-imidazol-4-yl]-methanone;
- (4-Bromophenyl)-{2-[2-(1-isopropyl-piperidin-4-yl)-ethoxy]-3-methyl-3H-imidazol-4-yl}-methanone;
- (4-Bromophenyl)-[2-(1-ethyl-piperidin-4-ylmethoxy)-3-methyl-3H-imidazol-4-yl]-methanone;
- (4-Bromophenyl)-[2-(1-sec-butyl-piperidin-4-ylmethoxy)-3-methyl-3H-imidazol-4-yl]-methanone;
- (4-Bromophenyl)-[3-methyl-2-(1-methyl-piperidin-4-ylmethoxy)-3H-imidazol-4-yl]-methanone;

(4-Bromophenyl)-{3-methyl-2-[1-(3-methyl-butyl)-piperidin-4-ylmethoxy]-3H-imidazol-4-yl}-methanone;
(4-Bromophenyl)-[2-(1'-isopropyl-[1,4']bipiperidinyl-4-ylmethoxy)-3-methyl-3H-imidazol-4-yl]-methanone;
(4-Bromophenyl)-[2-(1-cyclohexyl-piperidin-4-ylmethoxy)-3-methyl-3H-imidazol-4-yl]-methanone;
(4-Chlorophenyl)-[2-(1-isopropyl-piperidin-4-yloxy)-3-methyl-3H-imidazol-4-yl]-methanone;
(4-Chlorophenyl)-(3-methyl-2-phenylsulfanyl-3H-imidazol-4-yl)-methanol;
(4-Chlorophenyl)-(3-methyl-2-phenylsulfanyl-3H-imidazol-4-yl)-methanone;
(2-Benzenesulfonyl-3-methyl-3H-imidazol-4-yl)-(4-chlorophenyl)-methanone;
1-[2-(3-Dimethylamino-propylsulfanyl)-3-methyl-3H-imidazol-4-yl]-ethanone;
(4-Chlorophenyl)-[3-methyl-2-(4-piperidin-1-ylmethyl-phenoxy)-3H-imidazol-4-yl]-methanone;
1-[3-Methyl-2-(3-piperidin-1-yl-propoxy)-3H-imidazol-4-yl]-ethanone;
(4-Chlorophenyl)-[2-(1-isopropyl-piperidin-4-ylsulfanyl)-3-methyl-3H-imidazol-4-yl]-methanone;
(4-Chlorophenyl)-[3-methyl-2-(4-piperidin-1-yl-butylsulfanyl)-3H-imidazol-4-yl]-methanone;
[3-Methyl-2-(3-piperidin-1-yl-propoxy)-3H-imidazol-4-yl]-naphthalen-1-yl-methanone;
[3-Methyl-2-(3-piperidin-1-yl-propoxy)-3H-imidazol-4-yl]-naphthalen-1-yl-methanol;
1-[3-Methyl-2-(3-piperidin-1-yl-propoxy)-3H-imidazol-4-yl]-ethanol;
(4-Methoxyphenyl)-[3-methyl-2-(3-piperidin-1-yl-propoxy)-3H-imidazol-4-yl]-methanone;
[3-Methyl-2-(3-piperidin-1-yl-propoxy)-3H-imidazol-4-yl]-pyridin-4-yl-methanone;
[3-Methyl-2-(3-piperidin-1-yl-propoxy)-3H-imidazol-4-yl]-pyridin-3-yl-methanone;
[3-Methyl-2-(3-piperidin-1-yl-propoxy)-3H-imidazol-4-yl]-pyridin-2-yl-methanone;
Cyclohexyl-[3-methyl-2-(3-piperidin-1-yl-propoxy)-3H-imidazol-4-yl]-methanone;
Biphenyl-4-yl-[3-methyl-2-(3-piperidin-1-yl-propoxy)-3H-imidazol-4-yl]-methanone;
3-Methyl-2-(3-piperidin-1-yl-propoxy)-3H-imidazol-4-yl-carbaldehyde;
(3,5-Dichlorophenyl)-[2-(1-isopropyl-piperidin-4-ylmethoxy)-3-methyl-3H-imidazol-4-yl]-methanol;
4-{Hydroxy-[2-(1-isopropyl-piperidin-4-ylmethoxy)-3-methyl-3H-imidazol-4-yl]-methyl}-benzonitrile;
(3,5-Dichlorophenyl)-[2-(1-isopropyl-piperidin-4-ylmethoxy)-3-methyl-3H-imidazol-4-yl]-methanone;
(2-Chlorophenyl)-[2-(1-isopropyl-piperidin-4-ylmethoxy)-3-methyl-3H-imidazol-4-yl]-methanone;
4-[2-(1-Isopropyl-piperidin-4-ylmethoxy)-3-methyl-3H-imidazole-4-carbonyl]-benzonitrile;
(3-Chlorophenyl)-[2-(1-isopropyl-piperidin-4-ylmethoxy)-3-methyl-3H-imidazol-4-yl]-methanone;
[2-(1-Isopropyl-piperidin-4-ylmethoxy)-3-methyl-3H-imidazol-4-yl]-(4-trifluoromethyl-phenyl)-methanone;
[2-(1-Isopropyl-piperidin-4-ylmethoxy)-3-methyl-3H-imidazol-4-yl]-(4-nitro-phenyl)-methanone;
(4-Fluorophenyl)-[2-(1-isopropyl-piperidin-4-ylmethoxy)-3-methyl-3H-imidazol-4-yl]-methanone;
(4-Isopropylphenyl)-[2-(1-isopropyl-piperidin-4-ylmethoxy)-3-methyl-3H-imidazol-4-yl]-methanone;
{3-[5-(4-Chlorobenzyl)-1-methyl-1H-imidazol-2-ylsulfanyl]-propyl}-dimethyl-amine;
(4-Chlorophenyl)-[2-(3-dimethylamino-propylsulfanyl)-3-methyl-3H-imidazol-4-yl]-methanone oxime;
[3-Methyl-2-(3-piperidin-1-yl-propoxy)-3H-imidazol-4-yl]-piperidin-1-yl-methane;
(4-Chloro-phenyl)-[2-(3-dimethylamino-propane-1-sulfinyl)-3-methyl-3H-imidazol-4-yl]-methanone;
(4-Chlorophenyl)-[2-(3-dimethylamino-propane-1-sulfonyl)-3-methyl-3H-imidazol-4-yl]-methanone;
(4-Chlorophenyl)-[2-(3-dimethylamino-propane-1-sulfonyl)-3-methyl-3H-imidazol-4-yl]-methanone oxide;
(4-Chloro-phenyl)-[2-(1-isopropyl-piperidin-4-ylmethoxy)-3-methyl-3H-imidazol-4-yl]-methanone maleate salt;
(3-Fluoro-phenyl)-[3-methyl-2-(3-piperidin-1-yl-propylamino)-3H-imidazol-4-yl]-methanol;
(3-Fluoro-phenyl)-[3-methyl-2-(1-methyl-piperidin-4-ylsulfanyl)-3H-imidazol-4-yl]-methanol;
4-{5-[(3-Fluoro-phenyl)-(tert-butyl-dimethyl-silanyloxy)-methyl]-1-methyl-1H-imidazol-2-ylsulfanyl}-1-methyl-piperidine;
(3-Fluoro-phenyl)-[2-(1-isopropyl-piperidin-4-ylmethoxy)-3-methyl-3H-imidazol-4-yl]-methanol; and
4-{5-[(3-Fluoro-phenyl)-(tert-butyl-dimethyl-silanyloxy)-methyl]-1-methyl-1H-imidazol-2-yloxymethyl}-1-isopropyl-piperidine.

57. A method according to claim 1, wherein (B) is 2-Chloro-1-methyl-11H-imidazole.

58. A method according to claim 1, wherein (C) is 2-Chloro-3-methyl-3H-imidazole-4-carboxylic acid, or 2-Chloro-3-methyl-3H-imidazole-4-carbaldehyde.

59. A method according to claim 7, wherein said compound of formula (I) is (4-Chloro-phenyl)-[2-(1-isopropyl-piperidin-4-ylmethoxy)-3-methyl-3H-imidazol-4-yl]-methanone, said formula (A) is N-methylimidazole, said base is n-BuLi, and said formula (B) is 2-Chloro-1-methyl-1H-imidazole.

60. A method according to claim 59, wherein said formula (B) is 2-chloro-1-methyl-1H-imidazole, and further comprising reacting said 2-chloro-1-methyl-1H-imidazole with n-BuLi and performing an addition with 4-chloro-N-methoxy-N-methyl-benzamide.

61. A method according to claim 59, further comprising reacting (4-Chlorophenyl)-[2-(1-isopropyl-piperidin-4-ylmethoxy)-3-methyl-3H-imidazol-4-yl]-methanone with maleic acid.

62. A method according to claim 46, further comprising an oxidization step.

63. A method according to claim 62, further comprising performing a displacement with a nucleophile H-A$^3$-L$^3$-Q$^3$, wherein L$^3$ in said nucleophile H-A$^3$-L$^3$-Q$^3$ is chosen independently of L$^3$ in said H-A$^3$-L$^3$-Q$^4$, in the presence of a base.

* * * * *